US012789175B2

(12) United States Patent
Zhu et al.

(10) Patent No.: US 12,789,175 B2
(45) Date of Patent: Nov. 10, 2026

(54) PORPHYRIN PHOTOSENSITIZER AND COBALOXIME COCATALYST AND METHODS OF USE THEREOF

(71) Applicants: Hong Kong Baptist University, Hong Kong (CN); The Hong Kong Polytechnic University, Hong Kong (CN)

(72) Inventors: Xunjin Zhu, Hong Kong (CN); Govardhana Babu Bodedla, Hong Kong (CN); Wai-Kwok Wong, Hong Kong (CN); Wai-Yeung Wong, Hong Kong (CN)

(73) Assignees: Hong Kong Baptist University, Hong Kong (CN); The Hong Kong Polytechnic University, Hong Kong (CN)

( * ) Notice: Subject to any disclaimer, the term of this patent is extended or adjusted under 35 U.S.C. 154(b) by 1171 days.

(21) Appl. No.: 17/809,294

(22) Filed: Jun. 28, 2022

(65) Prior Publication Data

US 2023/0051807 A1 Feb. 16, 2023

Related U.S. Application Data

(60) Provisional application No. 63/202,983, filed on Jul. 2, 2021.

(51) Int. Cl.

| | |
|---|---|
| ***B01J 31/18*** | (2006.01) |
| ***B01J 35/39*** | (2024.01) |
| ***C01B 3/042*** | (2026.01) |
| ***C07D 487/22*** | (2006.01) |
| ***C07F 15/00*** | (2006.01) |

(52) U.S. Cl.

CPC .......... *B01J 31/1815* (2013.01); *B01J 35/39* (2024.01); *C01B 3/042* (2013.01); *C07D 487/22* (2013.01); *C07F 15/0013* (2013.01); *B01J 2231/005* (2013.01); *B01J 2531/26* (2013.01); *B01J 2531/845* (2013.01)

(58) Field of Classification Search

CPC .................... B01J 31/1815; B01J 35/39; B01J 2231/005; B01J 2531/26; B01J 2531/845; B01J 2540/12; B01J 2540/442; B01J 31/1691; B01J 31/1805; B01J 31/181; B01J 31/183; B01J 31/1835; C01B 3/042; C07F 15/0013; C07D 487/22; Y02E 60/36

See application file for complete search history.

(56) References Cited

PUBLICATIONS

Bodedla et al., Chemical Communications (Cambridge, United Kingdom), (2018), 54(82), 11614-11617. (Year: 2018).*

* cited by examiner

*Primary Examiner* — Laura L Stockton
(74) *Attorney, Agent, or Firm* — S&F/WEHRW

(57) ABSTRACT

Porphyrin photosensitizers including 5,15-di(naphthalimide) moieties useful for photocatalytic hydrogen evolution, compositions including the same, and methods of use thereof.

20 Claims, 33 Drawing Sheets

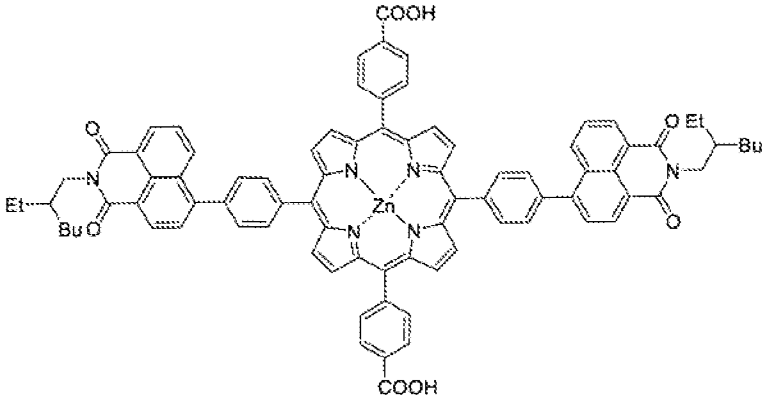
ZnDC(*p*-NI)PP
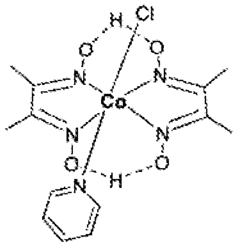
CoPyCl
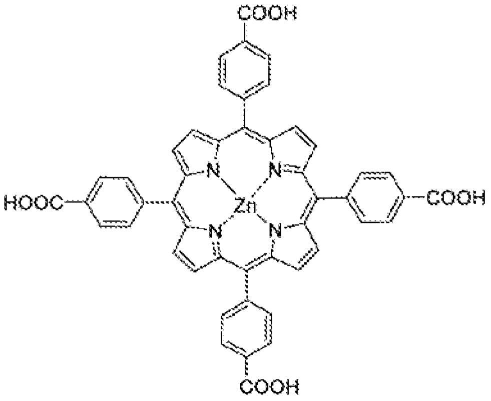
ZnTCPP
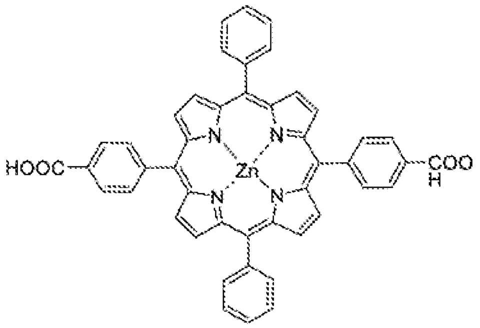
ZnDCPP
Fig. 1A

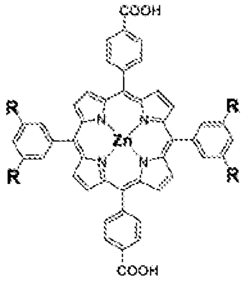
ZnDC(p-TNI)PP
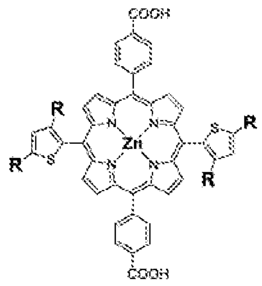
ZnDC(p-TNI)TP
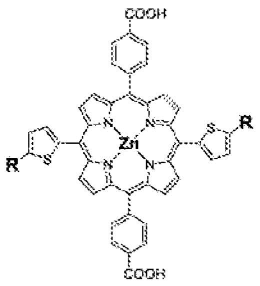
ZnDC(p-NI)TP
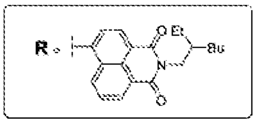
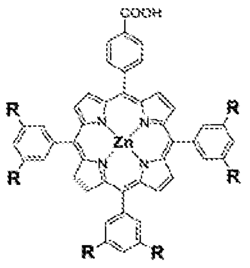
ZnMC(p-HNI)PP
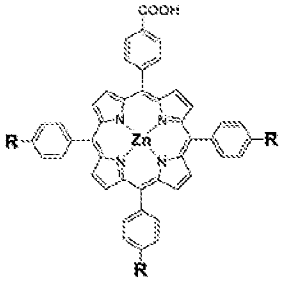
ZnMC(p-TriNI)PP
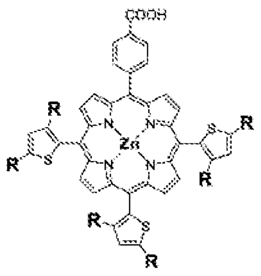
ZnMC(p-HNI)TP
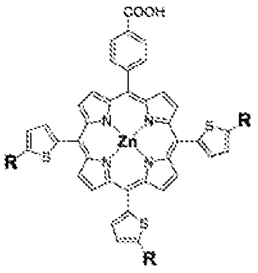
ZnMC(p-TriNI)TP
Fig. 1B

HONG KONG BAPTIST UNIVERSITY
DEPARTMENT OF CHEMISTRY (MALDI-TOF)

BRUKER

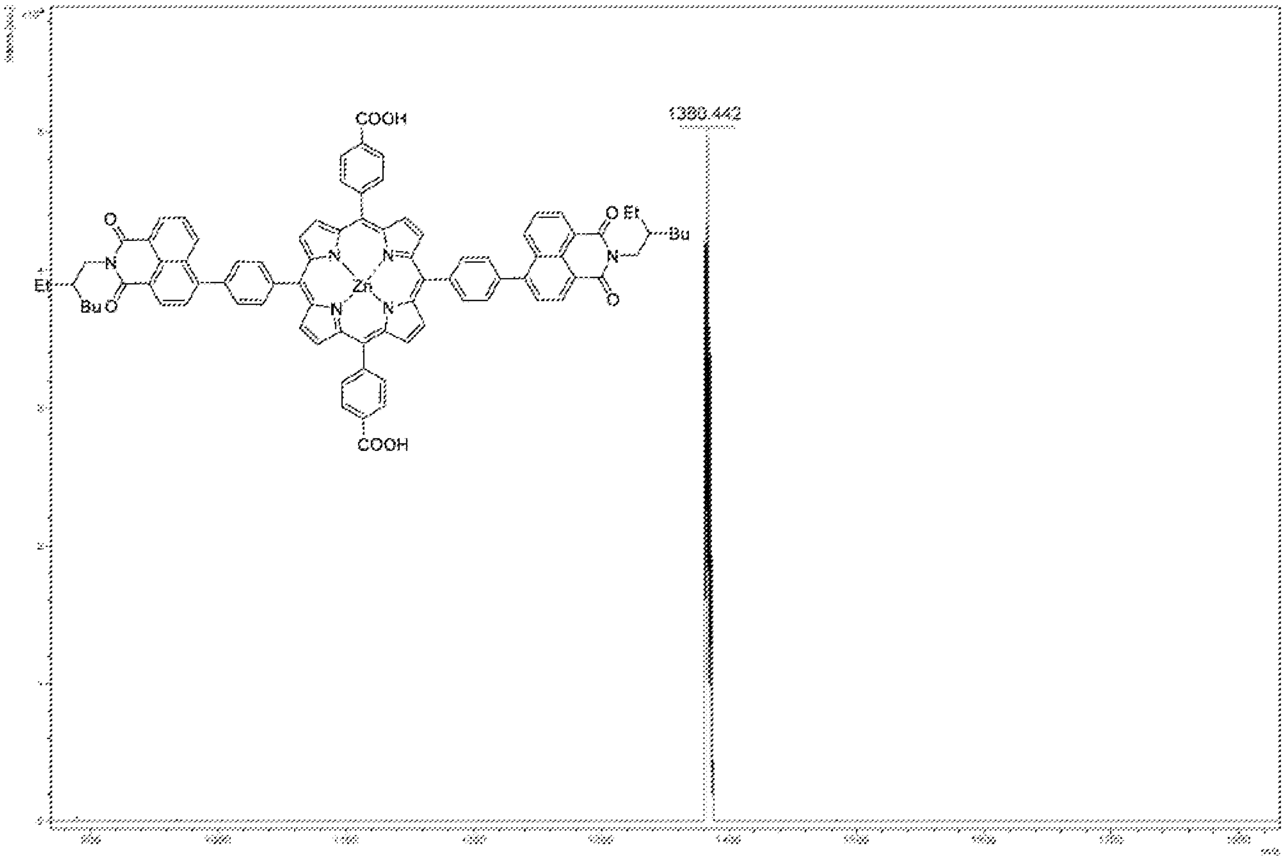

Target

| | |
|---|---|
| Target type | 0280781 |
| Target serial number | 1003444 |
| Position | K3 |

Laser

| | |
|---|---|
| Laser beam attenuation | 46 |
| Laser beam focus | 8 |
| Laser repetition rate | 2000 Hz |
| Number of shots | 500 |

Spectrometer

| | |
|---|---|
| positive voltage polarity | POS |
| PIE delay | 120 ns |
| Ion source voltage 1 | 19 kV |
| Ion source voltage 2 | 16.75 kV |
| Lens voltage | 8.3 kV |
| Linear detector voltage | 0 kV |
| Deflection on | |
| Deflection mass | |
| Reflector voltage 1 | 21 kV |
| Reflector voltage 2 | 9.6 kV |
| Reflector detector volt. | 1.887 kV |

Instrument

| | |
|---|---|
| Instrument type | autoflex |
| Instrument serial | 1857351.00824 |
| Name of computer | FLEX-PC |
| Operator ID or name | admin |
| flexControl version | flexControl 3.4.168.0 |
| flexAnalysis version | 3.4.79.0 |

RESULT

Theoretical Mass = [M]+ = 1380.455281
Experimental Mass = [M]+ = 1380.442
Error = -1.3281 PPM Bruker Daltonics

Fig. 30

PORPHYRIN PHOTOSENSITIZER AND COBALOXIME COCATALYST AND METHODS OF USE THEREOF

CROSS-REFERENCE TO RELATED APPLICATIONS

The present application claims priority from U.S. Provisional Patent Application No. 63/202,983, filed on Jul. 2, 2021, which is hereby incorporated by reference in its entirety.

TECHNICAL FIELD

The present disclosure relates to a new A-π-D-π-A based porphyrins useful for photocatalytic hydrogen evolution.

BACKGROUND

Solar light-driven splitting of water into hydrogen as carbon free fuel and environmentally friendly clean energy is a promising strategy for reducing consumption of natural fossil fuel resources and greenhouse effect. To produce photocatalytic hydrogen evolution (PHE), the photocatalytic systems (PSs) mainly contain three components such as photosensitizer, sacrificial electron donor and water reduction catalyst (WRC). Based on this multicomponent PS design, Lehn and co-workers first reported decent PHE results using $Ru(bpy)_3^{2+}$ as a photosensitizer, triethanolamine (TEOA) as a sacrificial donor and colloidal Pt as a WRC. After a huge number of multicomponent homogeneous/heterogeneous PSs have been developed by employing different combinations of photosensitizers such as Ru—, Ir— and Re-based complexes (noble metals), inorganic composites, porous materials, organic small molecules and polymers, graphitic carbon nitride ($g-C_3N_4$) polymeric materials, porphyrin derivatives and their hybrids with $g-C_3N_4$/graphene oxide and WRCs such as colloidal Pt, Ni—, Fe— and Co-based complexes with the use of sacrificial donors such as triethylamine (TEA), ascorbic acid (AA) and TEOA. Although the PSs comprising either noble metal-based photosensitizers or WRCs (e.g., platinum (Pt)) produced highly efficient PHE, they cannot be commercialized in the near future due to the high cost of noble metals. To tackle this problem, researchers are mainly devoted to use noble metal free photosensitizers and WRCs for the preparation of PSs. Among the noble metal free photosensitizers, recently, porphyrin derived materials have attracted enormous interest in the PHE owing to their strong solar light absorbing nature in the maximum UV-Vis region, long-lived photoexcited states and possession of suitable HOMO and LUMO energy levels for efficient photoinduced charge separation and their transfer to WRC.

On the other hand, cobalt complexes, especially, cobaloximes as WRC have received tremendous interest due to their easy synthesis, reasonable photostability and high PHE efficiencies due to low reduction potential. Importantly, understanding of electron transfer between the components of PSs is the main criteria to improve the PHE. For this, preparation of PSs in fully homogeneous condition is required. So, development of new PSs comprising of porphyrin photosensitizers and cobaloxime catalysts in homogenous condition for high performance PHE is not only prerequisite but also necessary to pave this research field towards our modern-day society. However, though a very few homogeneous PSs featuring porphyrin photosensitizers and cobaloxime WRCs for PHE have been reported so far, they are not much efficient and stable due to weak light absorbing nature of porphyrins and their photo instability.

SUMMARY

Provided herein are novel A-π-D-π-A based porphyrins, exemplified by ZnDC(p-NI)PP containing 5,15-di(naphthalimide) for PHE. The porphyrin photosensitizers described herein exhibit enhanced the light absorbing properties and photostability.

In a first aspect, provided herein is a porphyrin having the Formula 1:

1

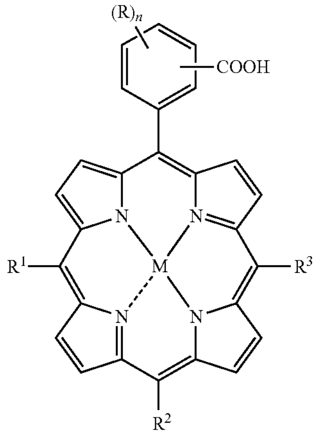

or a conjugate salt thereof, wherein

M is 2H, Zn, Fe, Ni, Co, V, Mn, Mg, Cu, Pt, Pd, or Sn;

n for each instance is a whole number selected from 0-3;

p for each instance is a whole number selected from 0-3;

q for each instance is 1 or 2;

r for each instance is a whole number selected from 0-2;

t for each instance is a whole number selected from 0-2;

R for each instance is alkyl, OH, cycloalkyl, aryl, heteroaryl, heterocycloalkyl, or COOH;

$R^1$ and $R^3$ are independently selected from the group consisting of:

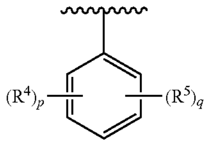 and 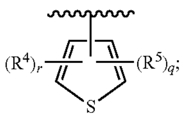

$R^2$ is selected from the group consisting of:

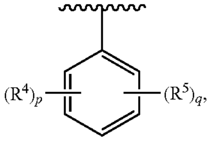, 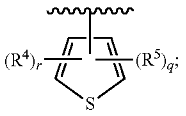 and

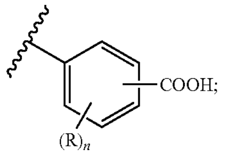

$R^4$ for each instance is independently selected from the group consisting of halide, nitro, nitrile, alkyl, perhaloalkyl, aryl, and heteroaryl;

$R^5$ is a moiety having the structure:

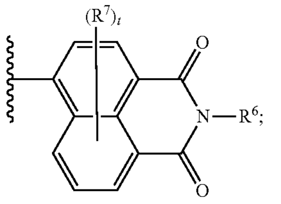

$R^6$ is alkyl, cycloalkyl, aryl or heteroaryl; and $R^7$ for each instance is independently selected from the group consisting of halide, nitro, nitrile, alkyl, perhaloalkyl, aryl, and heteroaryl.

In certain embodiments, each of $R^1$ and $R^3$ is:

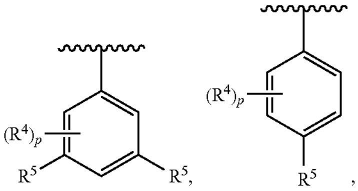

, or

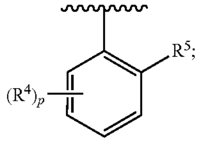

or each of $R^1$ and $R^3$ is:

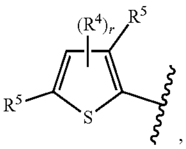

,

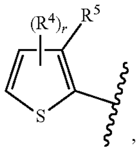

, or

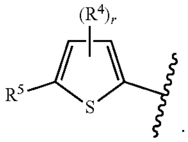

.

In certain embodiments, $R^2$ is:

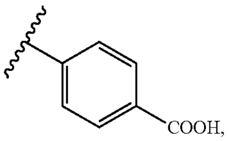

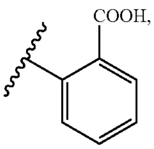

or

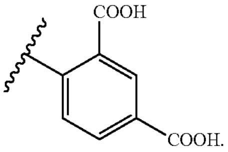

In certain embodiments, p is 0 and r is 0.

In certain embodiments, each of R', $R^2$, and $R^3$ is:

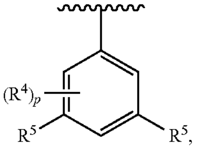

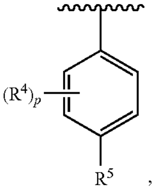

, or

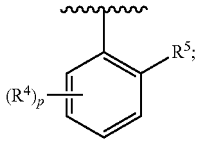

or each of R', $R^2$, and $R^3$ is:

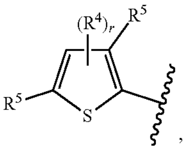

,

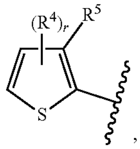

, or

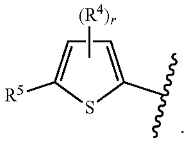

.

In certain embodiments, p is 0 and r is 0.

In certain embodiments, $R^6$ is alkyl.

In certain embodiments, the porphyrin is selected from the group consisting of:

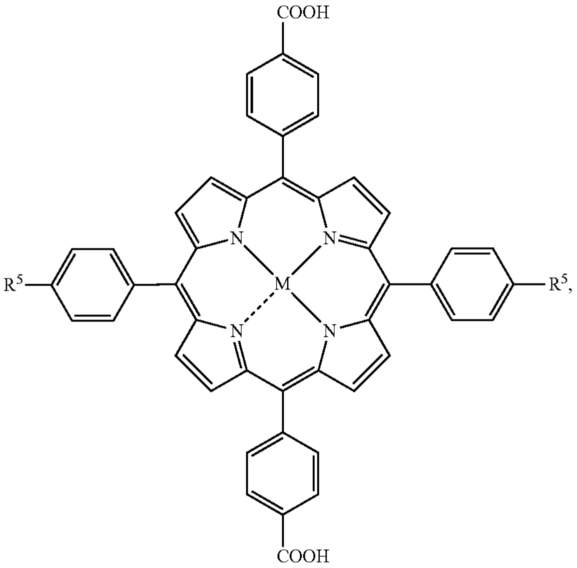

-continued
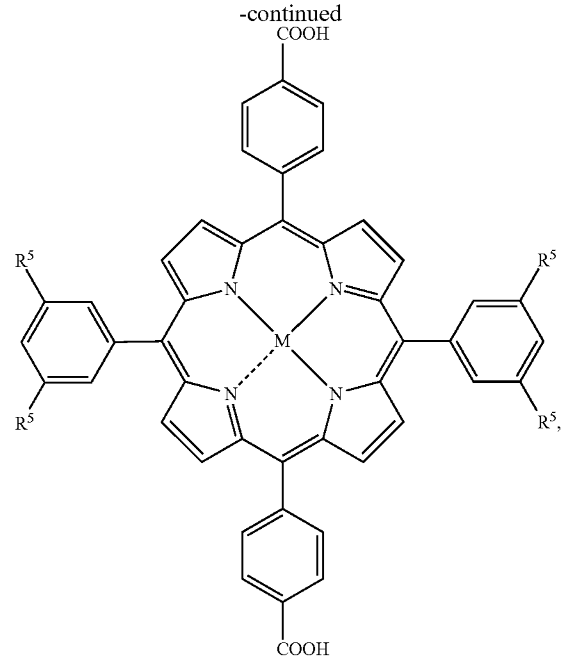
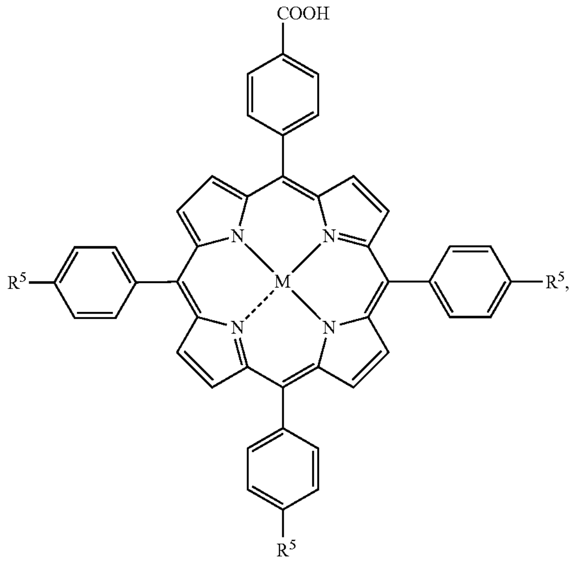
-continued
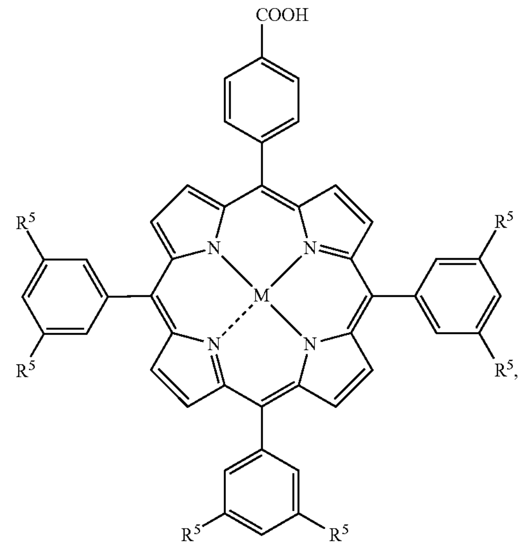
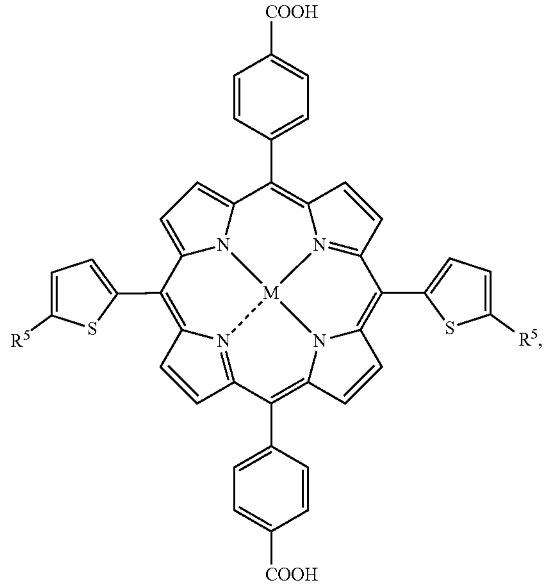
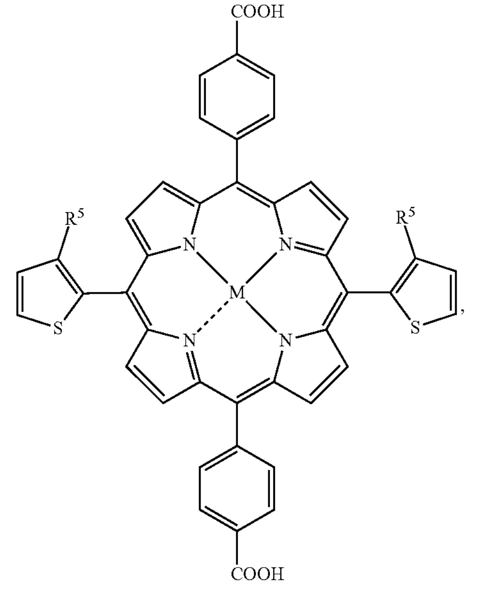

-continued
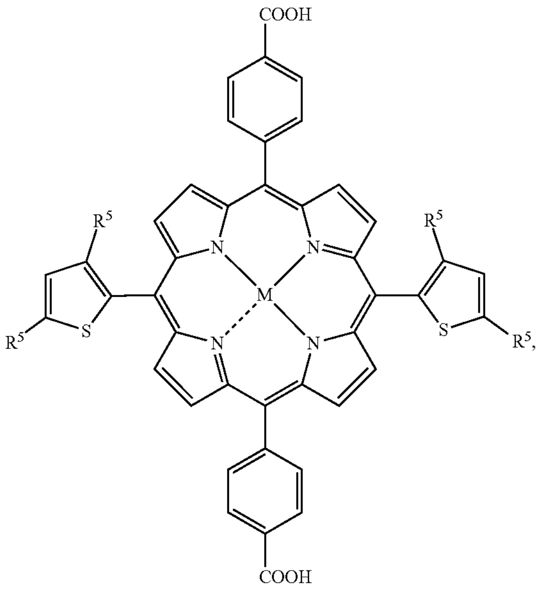
-continued
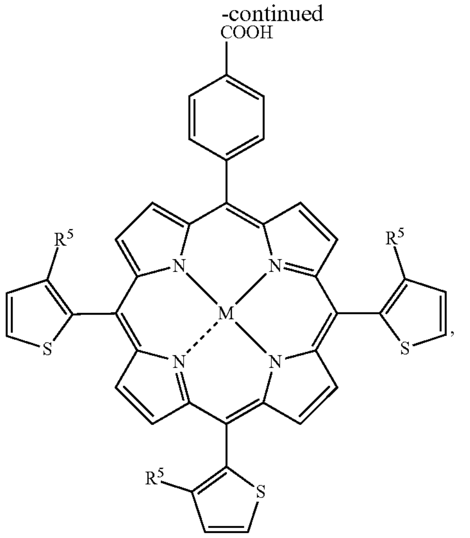
and
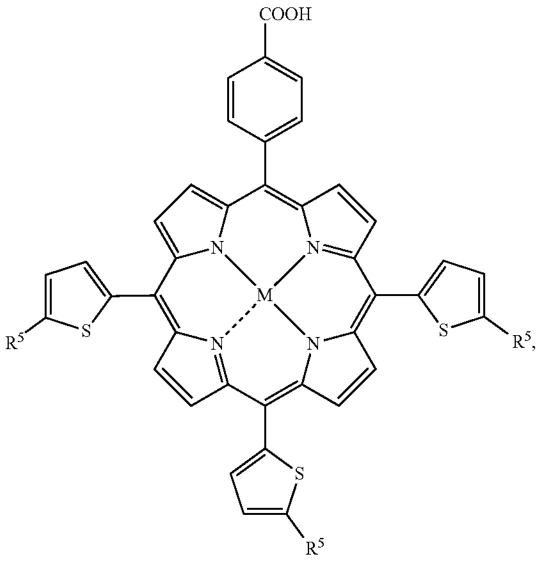
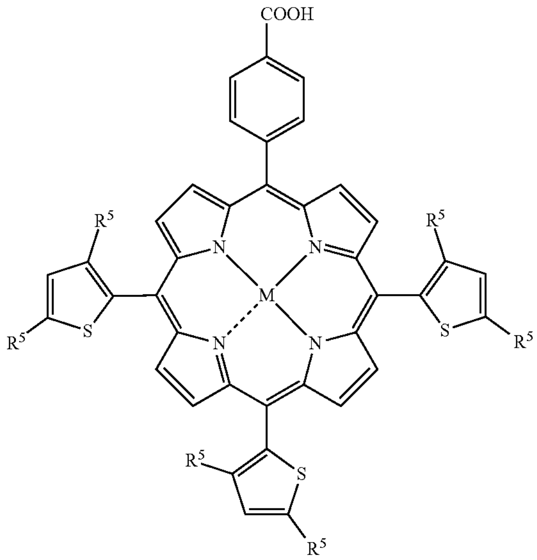
or a conjugate salt thereof.
In certain embodiments, t is 0 and $R^6$ is alkyl.
In certain embodiments, M is Zn(II).

In certain embodiments, the porphyrin has the structure:

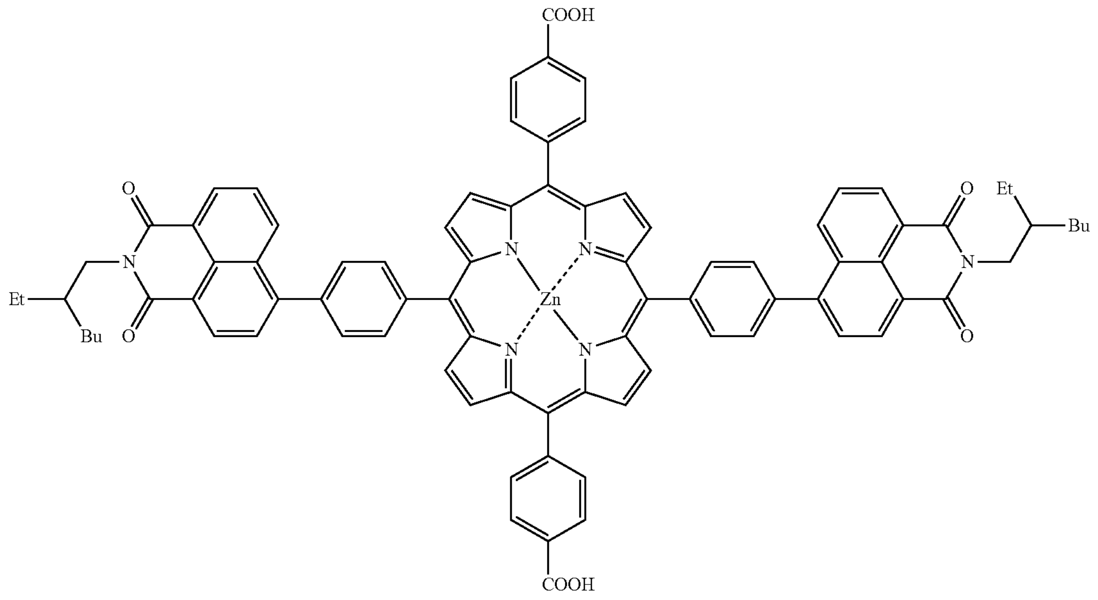

or a conjugate salt thereof.

In a second aspect, provided herein is a composition comprising a porphyrin of the first aspect and a water reduction catalyst.

In certain embodiments, the water reduction catalyst is a cobalt complex.

In certain embodiments, the cobalt complex is selected from the group consisting of a cobaloxime, a cobalt bipyridine, or a cobalt polypyridine.

In certain embodiments, the cobalt complex is chloro (pyridine)cobaloxime.

In certain embodiments, the composition further comprises water and a sacrificial electron donor.

In certain embodiments, the sacrificial electron donor is ascorbic acid, triethanolamine, triethylamine, ethylenediaminetetraacetic acid (EDTA), or a combination thereof.

In a third aspect, provided herein is a method of producing hydrogen gas comprising irradiating the composition, water, and a sacrificial electron donor with light.

In certain embodiments, the porphyrin has the structure:

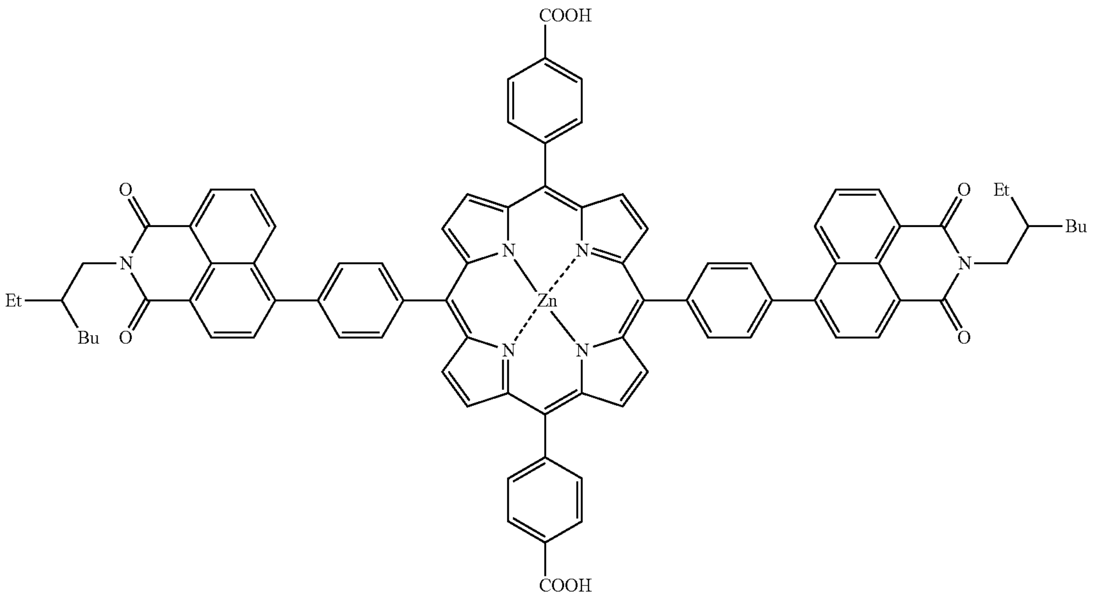

or a conjugate salt thereof.

In certain embodiments, the water reduction catalyst is chloro(pyridine)cobaloxime.

Other aspects and advantages of the present disclosure will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which:

FIG. 1A shows the structures of the porphyrins and chloro(pyridine)cobaloxime, (ZnDC(p-NI)PP; ZnTCPP; ZnDCPP and CoPyCl)

FIG. 1B shows the additional structure of porphyrins; ZnDC(p-TNI)PP ($C_{126}H_{112}N_8O_{12}Zn$), ZnDC(p-TNI)TP ($C_{122}H_{108}N_8O_{12}S_2Zn$), ZnDC(p-NI)TP ($C_{82}H_{66}N_6O_8S_2Zn$), ZnMC(p-HNI)PP ($C_{165}H_{154}N_{10}O_{14}Zn$), ZnMC(p-TriNI)PP ($C_{106}H_{93}N_7O_9Zn$), ZnMC(p-HNI)TP ($C_{159}H_{148}N_{10}O_{14}S_3Zn$) and ZnMC(p-TriNI)TP ($C_{99}H_{85}N_7O_8S_3Zn$).

FIG. 30 shows the MALDI—TOF spectrum of ZnDC(p-NI)PP

DETAILED DESCRIPTION

Figure 2A:
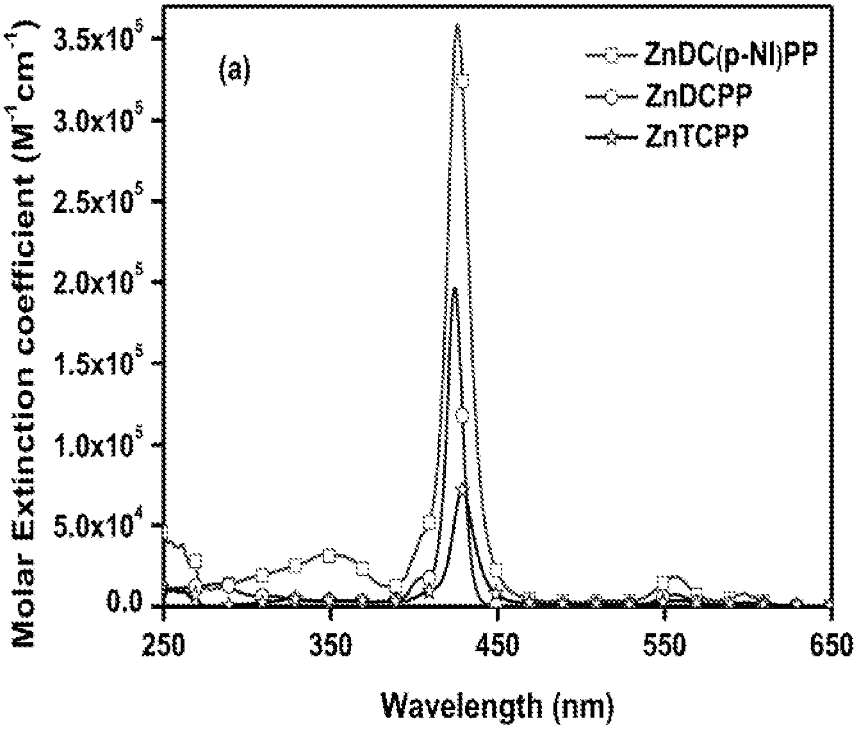
FIG. 2A shows the absorption spectra of the porphyrins (ZnDC(p-NI)PP; ZnTCPP and ZnDCPP) recorded in phosphate buffer/THF (9:1 v/v, 10 μM) solution

PHE is a promising strategy to produce environmentally friendly clean energy with the use of solar power and water. For this, development of an efficient and nobel metal free PSs comprising of high light-harvesting and photostable photosensitizers is an important and challenging task. Herein, a new A-π-D-π-A based porphyrin, ZnDC(p-NI)PP containing 5,15-di(naphthalimide) substituted porphyrin donor moiety, phenylene π-linker and carboxylic acid acceptor group is developed for PHE. The homogeneous PS of ZnDC(p-NI)PP produced a very high hydrogen evolution rate ($\eta H_2$) of 35.70 mmol $g^{-1}$ $h^{-1}$ and turnover number (TON) of 5,958 which are over 8- and 4-folds higher than the PS of ZnDCPP, which lacks the NI moieties ($\eta H_2$ of 4.64 mmol $g^{-1}$ $h^{-1}$, TON of 1397) with the use of chloropyridinecobaloxime (CoPyCl) water reduction catalyst in phosphate buffer/THF solution. Under the same conditions, the PS of typical ZnTCPP porphyrin possessing four COOH groups show very poor PHE results ($\eta H_2$ of 2.43 mmol $g^{-1}$ $h^{-1}$, TON of 562). The apparently higher PHE results of ZnDC(p-NI)PP than the ZnDCPP and ZnTCPP are attributed to the efficient intramolecular energy transfer from the NI moiety to the porphyrin ring that would promote the long-lived photoexcitation which further accepts electrons efficiently from sacrificial donor followed by transferring to CoPyCl through carboxylic acid groups and consequently water reduction. More interestingly, the PHE results of ZnDC(p-NI)PP PS are also superior to the PSs containing porphyrin photosensitizers and coabaloxime photocatalysts reported so far. The results of this work pave a new direction for developing efficient porphyrin-based materials for PHE through suitable molecular design approach.

Definitions

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heterocycloalkyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like.

The term "nitro" is art-recognized and refers to $NO_2$; the term "halogen" is art-recognized and refers to —F, —$C_1$, —Br or —I; the term "sulfhydryl" is art-recognized and refers to —SH; the term "hydroxyl" means —OH; and the term "sulfonyl" is art-recognized and refers to —$SO_2$—. "Halide" designates the corresponding anion of the halogens, and "pseudohalide" has the definition set forth on 560 of "Advanced Inorganic Chemistry" by Cotton and Wilkinson.

Other definitions for selected terms used herein may be found within the detailed description of the invention and apply throughout. Unless otherwise defined, all other technical terms used herein have the same meaning as commonly understood to one of ordinary skill in the art to which the invention belongs.

The present disclosure provides a porphyrin having the Formula 1:

1

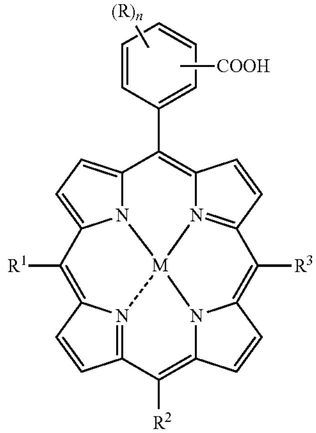

or a conjugate salt thereof, wherein

M is 2H, Zn, Fe, Ni, Co, V, Mn, Mg, Cu, Pt, Pd, or Sn;

n for each instance is a whole number selected from 0-3;

p for each instance is a whole number selected from 0-3;

q for each instance is 1 or 2;

r for each instance is a whole number selected from 0-2;

t for each instance is a whole number selected from 0-2;

R for each instance is alkyl, OH, cycloalkyl, aryl, heteroaryl, heterocycloalkyl, or COOH;

$R^1$ and $R^3$ are independently selected from the group consisting of:

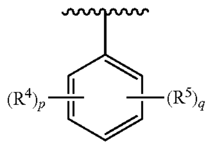

and

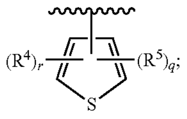

$R^2$ is selected from the group consisting of:

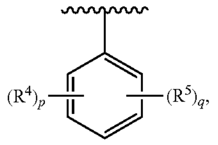

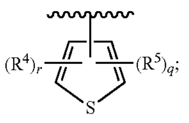

and

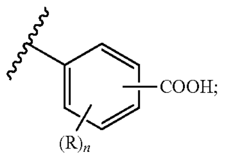

$R^4$ for each instance is independently selected from the group consisting of halide, nitro, nitrile, alkyl, perhaloalkyl, aryl, and heteroaryl;

$R^5$ is a moiety having the structure:

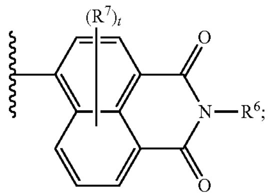

$R^6$ is alkyl, cycloalkyl, aryl or heteroaryl; and $R^7$ for each instance is independently selected from the group consisting of halide, nitro, nitrile, alkyl, perhaloalkyl, aryl, and heteroaryl.

In instances in which M is a metal, M can exist in a +1, +2. +3, +4 oxidation state. In certain embodiments, M is Zn(II), Fe(II), Fe(III), Ni(II), Ni(III), Co(II), Co(III), Pt(II), Pd(II), Mn(II), Mn(III), Mg(II), V(IV), Sn(II), or Cu(II).

When M is 2H, the compound of Formula 1 can be represented by a compound of Formula 2:

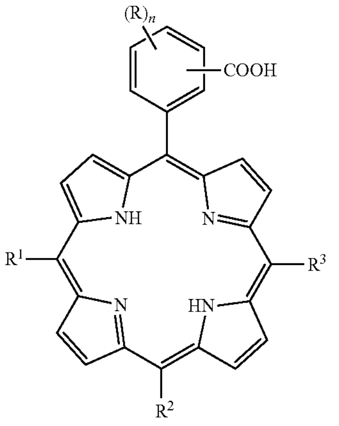

2 wherein n, p, q, r, t, R, $R^1$, $R^2$, $R^3$, $R^4$, $R^5$, $R^6$, and $R^7$ are as defined herein.

In cases where the oxidation state of M is +3 or greater, the porphyrin can further comprise one or more anions. The anion can be any anion, such as, but not limited to, halide, nitrate, cyanide, phosphate, sulfate, carbonate, bicarbonate, tetrafluoroborate, hexafluoroantimonate, thiocyanate, mesylate, phenylsulfonate, toluenesulfonate, trifluoroacetate, acetate, formate, oxalate, silicate, and the like.

In certain embodiments, the porphyrin is selected from the group consisting of:

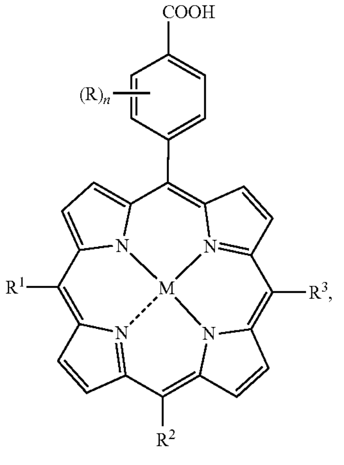

-continued

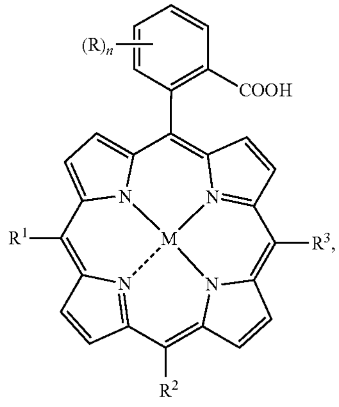

and

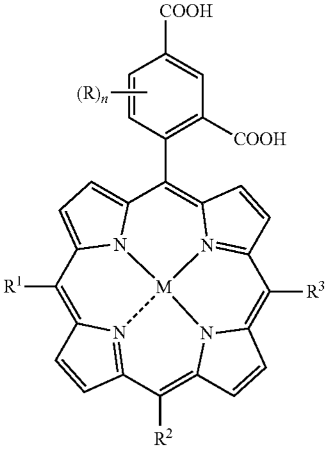

or a conjugate salt thereof, wherein each of n, p, q, r, t, R, $R^1$, $R^2$, $R^3$, $R^4$, $R^5$, $R^6$, and $R^7$ is as defined herein.

R for each instance can independently be selected from the group consisting of $C_1$-$C_6$ alkyl, OH, $C_3$-$C_6$ cycloalkyl, $C_6$-$C_{10}$ aryl, $C_4$-$C_9$ heteroaryl, $C_3$-$C_5$ heterocycloalkyl, and COOH. In certain embodiments, 1 or 2 R is COOH.

In certain embodiments, $R^1$ and $R^3$ are independently selected from the group consisting

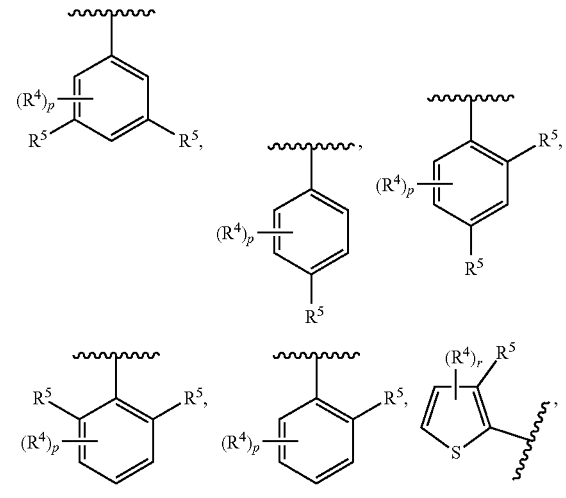

-continued

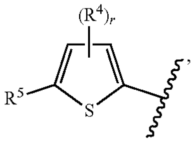,
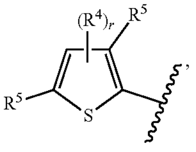, and

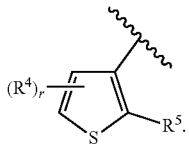

In certain embodiments, $R^2$ is selected from the group consisting of:

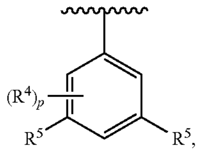
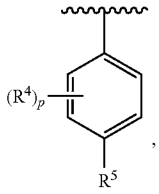,
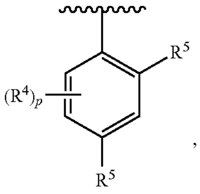,

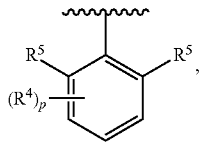
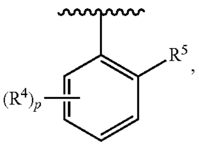
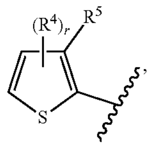

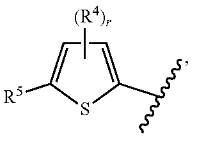
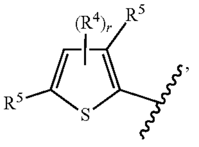

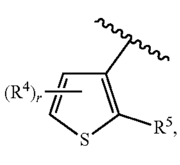
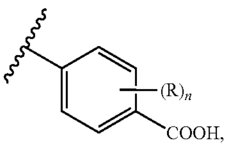

-continued

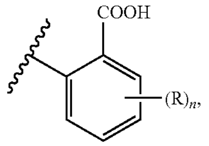
and
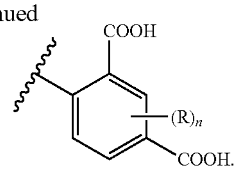

$R^4$ for each instance can independently be selected from the group consisting of fluoride, chloride, bromide, iodide, nitro, nitrile, $C_1$-$C_6$ alkyl, $C_1$-$C_6$ perhaloalkyl, $C_1$-$C_2$ perhaloalkyl, $C_6$-$C_{10}$ aryl, and $C_4$-$C_9$ heteroaryl.

$R^6$ for each instance can independently be selected from the group consisting of $C_1$-$C_{42}$ alkyl, $C_1$-$C_{30}$ alkyl, $C_1$-$C_{20}$ alkyl, $C_1$-$C_{15}$ alkyl, $C_3$-$C_{10}$ cycloalkyl, $C_6$-$C_{10}$ aryl, and $C_4$-$C_9$ heteroaryl. In certain embodiments, $R^6$ is —$CH_2CH(R^8)(R^9)$, wherein each of $R^8$ and $R^9$ is independently selected from the group consisting of $C_1$-$C_{20}$ alkyl, $C_1$-$C_{18}$ alkyl, $C_1$-$C_{16}$ alkyl, $C_1$-$C_{14}$ alkyl, $C_1$-$C_{12}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_2$-$C_{20}$ alkyl, $C_2$-$C_{18}$ alkyl, $C_2$-$C_{16}$ alkyl, $C_2$-$C_{14}$ alkyl, $C_2$-$C_{12}$ alkyl, $C_2$-$C_{10}$ alkyl, $C_2$-$C_8$ alkyl, $C_2$-$C_6$ alkyl, and $C_2$-$C_4$ alkyl.

$R^7$ for each instance is independently selected from the group consisting of fluoride, chloride, bromide, iodide, nitro, nitrile, $C_1$-$C_6$ alkyl, $C_1$-$C_6$ perhaloalkyl, $C_1$-$C_2$ perhaloalkyl, $C_6$-$C_{10}$ aryl, and $C_4$-$C_9$ heteroaryl.

As set out herein, certain embodiments of the porphyrins described herein may contain a basic functional group and are thus capable of forming salts with acids. These salts can be prepared by reacting a porphyrin described herein in its free base form with a suitable organic or inorganic acid, and isolating the salt thus formed during subsequent purification. Representative salts include fluoride, bromide, chloride, iodide, nitrate, cyanide, phosphate, sulfate, hydrogensulfate, carbonate, bicarbonate, tetrafluoroborate, hexafluoroantimonate, thiocyanate, mesylate, phenylsulfonate, toluenesulfonate, trifluoroacetate, acetate, formate, oxalate, silicate, valerate, oleate, palmitate, stearate, laurate, benzoate, lactate, tosylate, citrate, maleate, fumarate, succinate, tartrate, napthylate, glucoheptonate, lactobionate, and laurylsulphonate salts and the like.

In other cases, the porphyrins described herein may contain one or more acidic functional groups and are thus capable of forming salts with bases. These salts can likewise be prepared in by reacting the porphyrin in its free acid form with a suitable base, such as the hydroxide, carbonate or bicarbonate of a metal cation, with ammonia, or with an organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The porphyrins described herein can be readily prepared from commercially available starting materials using well known synthetic methods. It is within the skill of a person of ordinary skill in the art to select the appropriate starting materials and synthetic mythologies based on common general knowledge and the methods described herein.

An exemplary synthetic protocol for the preparation of ZnDC(p-NI)PP is shown in Scheme 1. The di-bromozinc derivative, DiBrZnD(p-NI)PP was synthesized by bromination of D(p-NI)$PPH_2$ with NBS reagent followed by reaction with $Zn(OAC)_2.2H_2O$. Subsequently, reaction of DiBrZnD (p-NI)PP with 4-carboxyphenyl boronic acid under Suzuki-miyaura coupling reaction yielded target ZnDC(p-NI)PP porphyrin.

Scheme 1. Synthetic route for the preparation of ZnDC(p-NI))PP porphyrin.

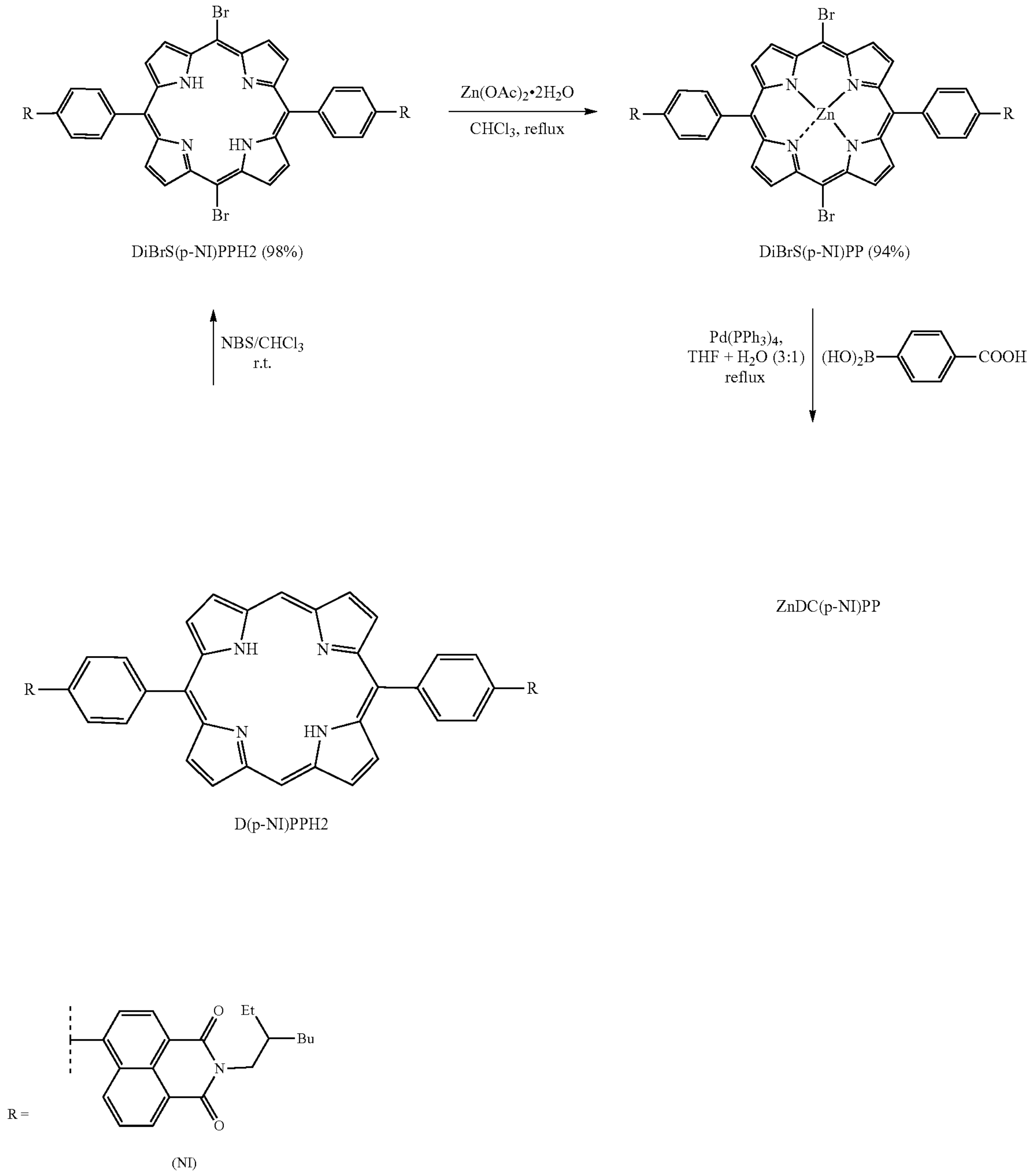

The controlled porphyrin ZnDCPP was synthesized in two steps (Scheme 2). Firstly, the acid catalyzed condensation of phenyl dipyyrolomethane with 4-formylmethylbenzoate produced the DMMPPH2 porphyrin and zinc metalation of this gave ZnDMCPP. In the second step, demethylation of ZnDMCPP under basic conditions resulted in ZnDCPP porphyrin.

Scheme 2. Synthetic route for the preparation of ZnDCPP porphyrin.
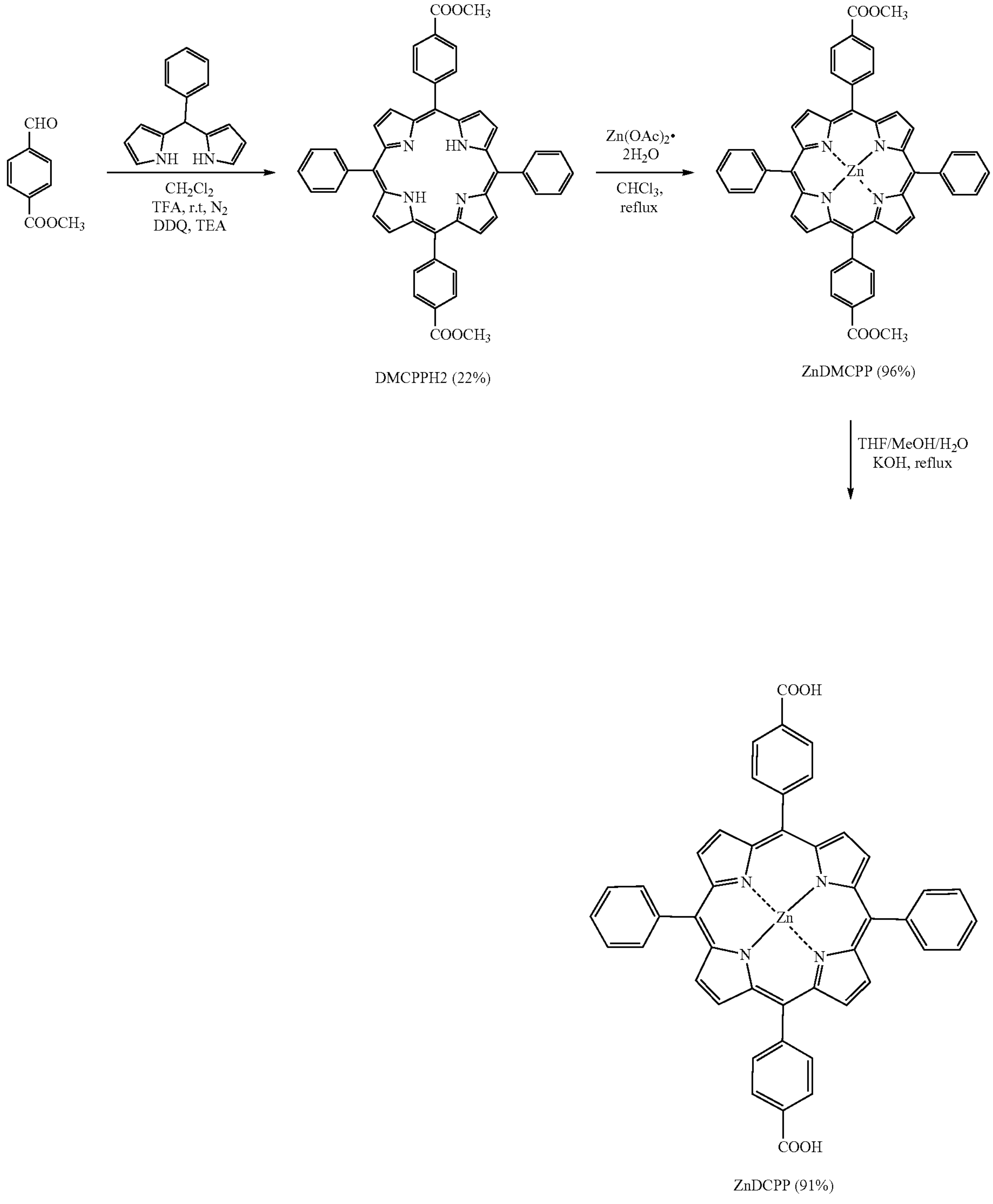
Zinc(II)-tetracarboxyphenylporphyrin (ZnTCPP) was synthesized for comparison (Scheme 3). Both porphyrins were thoroughly characterized by NMR and MALDI-TOF techniques (FIG. 18-33).

Scheme 3. Synthetic route for the preparation of ZnTCPP porphyrin.
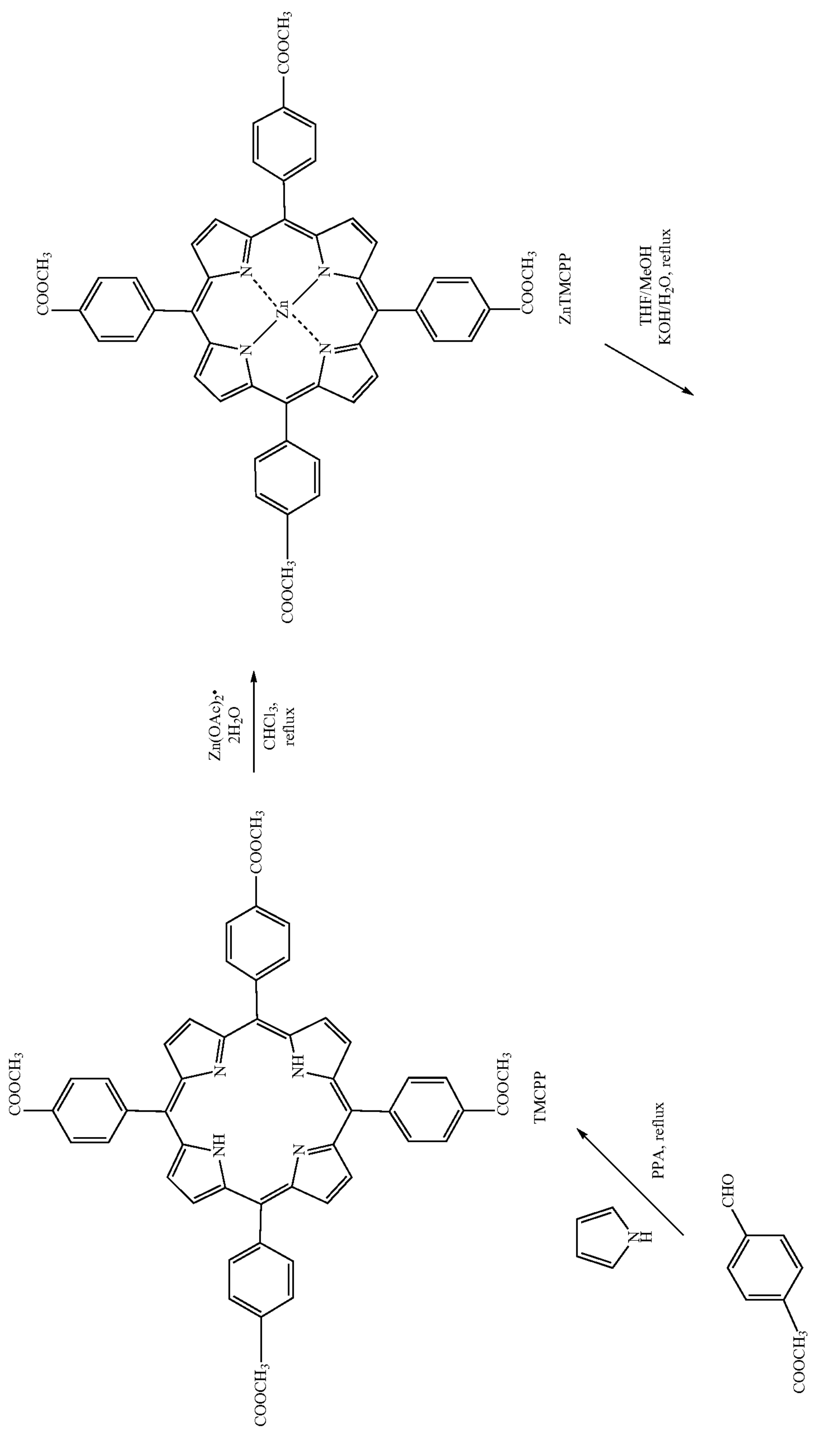

-continued
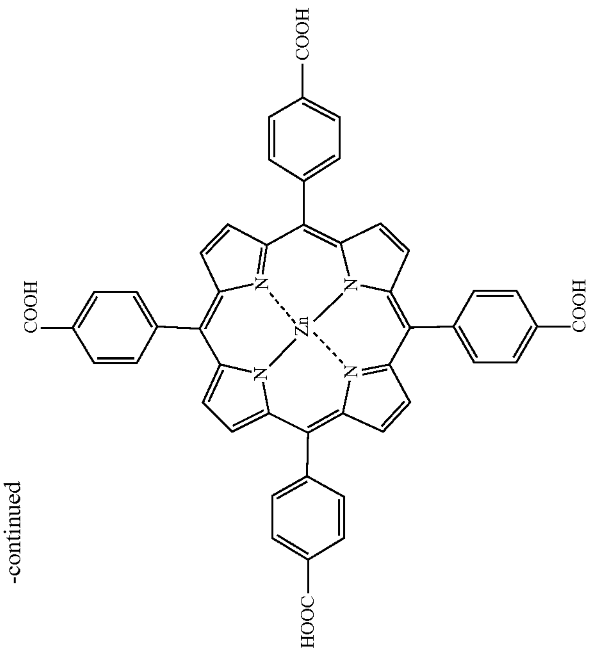
ZnTCPP

The present disclosure also provides a composition comprising the porphyrin described herein and a water reduction catalyst. In certain embodiments, the water reduction catalyst is a homogeneous photocatalyst or a heterogenous photocatalyst, such as platinum (Pt), rhodium (Rh), gold (Au), silver (Ag), nickel (Ni), metal oxides, phosphides, sulphides, carbides, selenides.

In certain embodiments, the water reduction catalyst is a cobalt complex selected from the group consisting of a cobaloxime, a cobalt bipyridine, and a cobalt polypyridine. The cobalt complex can be chloro(pyridine)cobaloxime (Co $(dmgH)_2Cl(py)$), $Co(Py)_4(BF_4)_2$, and Co(diphenylglyoximate)$_2$Cl(py), or $[Co(bpy)_3]^{2+}$.

In certain embodiments, the composition further comprises water and a sacrificial electron donor. The sacrificial electron donor is not particularly limited. Examples of sacrificial electron donors include, but are not limited to, ascorbic acid, triethanolamine, triethylamine, an alcohol, an amine, ethylenediaminetetraacetic acid (EDTA), or combinations thereof. The water can optionally comprise a buffer, such as a phosphate buffer.

The present disclosure also provides a method of producing hydrogen gas, the method comprising irradiating a composition comprising the phosphine described herein, a water reduction catalyst, a sacrificial electron donor, and optionally buffered water with light.

The light can be monochromatic or polychromatic light. In certain embodiments, the light comprises one or more wavelengths between 200-800 nm. In certain embodiments, the light comprises one or more wavelengths between 200-600 nm, 300-600 nm, 300-450 nm, or 400-600 nm.

Linear substitution of di-naphthalimide (NI) moieties at meso-position of porphyrin core can greatly improve light absorption, stability of photoexcited states, photoinduced charge separation and photostability of porphyrin photosensitizers and thus PHE. Without wishing to be bound by thereof, it is believed this could be attributed to the efficient intramolecular energy transfer from the NI energy donor to the porphyrin ring energy acceptor. Heterogeneous conditions were used to evaluate the PHE of di-NI conjugated porphyrin, ZnD(p-NI)PP with the use of Pt WRC. Though the PS of ZnD(p-NI)PP delivered efficient PHE results, it is not a cost-effective approach and the intrinsic photocatalytic cyclic mechanism was also not much fully addressed due to the usage of Pt and heterogeneous photocatalytic conditions, respectively. In order to prepare a cost-effective, efficient and homogeneous PSs, an A-π-D-π-A-based porphyrin photosensitizer, ZnDC(p-NI)PP bearing di-NI moieties and di-COOH groups (FIG. 1A) was developed and its PHE properties were tested using chloropyridinecobaloxime (CoPyCl) WRC under homogeneous phosphate buffer/THF conditions. Without wishing to be bound by thereof, it is believed that upon light irradiation on ZnDC(p-NI)PP porphyrin produces long-lived photoexcited states due to occurrence of energy transfer between NI moiety and porphyrin macrocycle resulting from overlapped absorption and emission spectral profiles of NI moiety and porphyrin macrocycle. As a result, the ZnDC(p-NI)P efficiently accepts electrons from sacrificial donor and quickly transfers to CoPyCl where proton reduction takes place. Thus, the PS of ZnDC(p-NI)PP porphyrin produced hydrogen evolution rate ($\eta H_2$) of 35.70 mmol $g^{-1}$ $h^{-1}$, which is 15-fold higher than the control porphyrin ZnDCPP which lacks the NI groups (4.64 mmol $g^{-1}$ $h^{-1}$) and even 15-fold higher than typical porphyrins, ZnTCPP (2.43 mmol $g^{-1}$ $h^{-1}$). As discussed herein, the $H_2$ evolution of the catalyst can be further improved by the design of NI—conjugated porphyrins by varying the numbers of COOH groups and n-linkers (FIG. 1B).

EXAMPLES

Materials and Methods

All the chemicals were purchased from commercial sources and used as received. Solvents were dried by distilling over suitable dehydrating agents according to standard procedures. Purification of the compounds was performed by column chromatography with 100-200 mesh silica. $^1H$ and $^{13}C$ NMR spectra were recorded in an NMR spectrometer operating at 400.00 and 100.00 MHz, respectively. The chemical shifts were calibrated from the residual peaks observed for the deuterated solvents chloroform ($CDCl_3$) at δ 7.26 ppm for $^1H$ and δ 77.0 ppm for $^{13}C$, respectively. High-resolution matrix-assisted laser desorption/ionization time-of-flight (MALDI-TOF) mass spectra were obtained with a Bruker Autoflex MALDI-TOF mass spectrometer. The optical absorption and emission spectra of the porphyrins were measured for the freshly prepared air equilibrated solutions at room temperature by using UV-Vis spectrophotometer and spectrofluorimeter, respectively. Cyclic voltammetry (CV) was recorded on an electrochemical workstation in THF solution by using 0.1 M tetrabutylammonium hexafluorophosphate ($TBAPF_6$) as supporting electrolyte. The experiments were performed at room temperature with a conventional three-electrode cell assembly consisting of a platinum wire as auxiliary electrode, a non-aqueous $Ag/AgNO_3$ reference electrode, ferrocene as internal standard and a glassy carbon working electrode.

Example 1—Preparation of D(p-NI)PPH2

In a 100 mL two-neck round-bottom flask, NI-Ph-CHO (0.5 g, 1.20 mmol), dipyrrolomethane (0.18 g, 1.2 mmol) and dichloromethane (100 mL) were taken and purged with nitrogen for 20 min. After TFA (200 μL) was added and the reaction mixture was stirred for 12 h at room temperature under nitrogen and dark. After 2,3-dichloro-5,6-dicyanobenzoquinone (DDQ) (0.55 g, 2.0 mmol) was added, and the reaction mixture was stirred for 30 min. The reaction was quenched by the addition of triethylamine (5 mL). After completion of reaction, the solvent was removed and the resulting crude product was purified by column chromatography with silica using chloroform/hexane (1:1, v/v) as eluent. Purple solid: yield 1.5 g, 20.0%. $^1H$ NMR ($CDCl_3$, 400.00 MHz) δ-3.03 (s, 2H), 0.923-0.96 (t, J=7.2 Hz, 6H), 0.99-1.03 (t, J=7.6 Hz, 6H), 1.36-1.49 (m, 16H), 2.02-2.08 (m, 2H), 4.18-4.27 (m, 4H), 7.89-7.97 (m, 6H), 8.08 (d, J=7.6 Hz, 2H), 8.48 (d, J=8.0 Hz, 4H), 8.71-8.76 (m, 4H), 8.83 (d, J=7.6 Hz, 2H), 9.25 (d, J=4.8 Hz, 4H), 9.50 (d, J=4.8 Hz, 4H), 10.41 (s, 2H). $^{13}C$ NMR ($CDCl_3$, 100.00 MHz) δ 10.80, 14.23, 23.20, 24.19, 28.83, 30.88, 38.08, 44.33, 105.67, 118.36, 122.15, 127.20, 128.32, 128.64, 131.07, 131.47, 132.03, 135.18, 145.40, 147.17, 164.79.

Example 2—Preparation of DiBrD(p-NI)PPH2

In a 250 mL two-neck round-bottom flask, D(p-NI)PPH2 (0.50 g, 0.46 mmol) and chloroform (200 mL) were taken and purged with nitrogen for 10 min. After NBS (0.18 g, 1.01 mmol) was added portion wise and the reaction mixture was stirred for 30 min at room temperature under nitrogen and dark. The reaction status was monitored by thin layer chromatography (TLC). After completion of reaction, the solvent was removed and the resulting crude product was purified by column chromatography with silica using chloroform/hexane (1:1, v/v) as eluent. Light green solid: yield 0.52 g, 92.0%. $^1$H NMR ($CDCl_3$, 400.00 MHz) δ-2.70 (s, 2H), 0.91-1.01 (m, 12H), 1.37-1.47 (m, 12H), 2.01-2.04 (m, 2H), 4.15-4.23 (m, 4H), 7.88-7.90 (m, 6H), 8.04 (d, J=7.6 Hz, 2H), 8.33 (d, J=8.0 Hz, 4H), 8.66 (d, J=8.8 Hz, 2H), 8.71 (d, J=7.2 Hz, 2H), 8.79 (d, J=7.2 Hz, 2H), 8.97 (d, J=4.0 Hz, 4H), 9.69 (d, J=4.8 Hz, 4H).

Example 3—Preparation of DiBrZnD(p-NI)PP

A mixture of DiBrD(p-NI)PPH2 (0.5 g, 0.40 mmol), $Zn(OAc)_2.2H_2O$ (0.74 g, 4.0 mmol) and $CHCl_3$ (200 mL) was refluxed overnight. After completion of the reaction, solvent was removed and the resulting crude product was purified by column chromatography with silica using chloroform as eluant. Green solid: yield 0.51 g, 98.0%. $^1$H NMR ($CDCl_3$, 400.00 MHz) δ 0.91-1.01 (m, 12H), 1.35-1.47 (m, 12H), 2.00-2.05 (m, 2H), 4.14-4.25 (m, 4H), 7.82-7.84 (m, 6H), 8.01 (d, J=7.6 Hz, 2H), 8.31 (d, J=8.0 Hz, 4H), 8.63-8.69 (m, 4H), 8.76 (d, J=7.6 Hz, 2H), 9.00 (d, J=4.4 Hz, 4H), 9.73 (d, J=4.8 Hz, 4H). $^{13}$C NMR ($CDCl_3$, 100.00 MHz) δ 10.75, 14.18, 23.16, 24.15, 28.80, 30.85, 38.03, 44.25, 105.15, 121.02, 121.97, 123.03, 127.05, 128.04, 128.21, 128.83, 130.08, 130.96, 131.33, 132.55, 133.24, 134.88, 137.99, 142.97, 146.43, 150.27, 150.65, 164.52, 164.68.

Example 4—Preparation of ZnDC(p-NI)PP

In a 100 mL two-neck round-bottom flask, DiBrZnD(p-NI)PP (0.20 g, 0.16 mmol), 4-carboxyphenylboronic acid (0.08 g, 0.46 mmol), potassium carbonate (0.14 g, 0.96 mmol) and 15 mL THF/$H_2O$ (3:1, v/v) were taken and purged with nitrogen. After addition of $Pd(PPh_3)_4$ (50 mg, 2 mol %) the reaction mixture was refluxed for 12 h. After completion of reaction, it was diluted with chloroform and water. The organic layer was separated, dried over $Na_2SO_4$ and solvent removed under reduced pressure. The resulting crude reaction mixture containing product was purified by column chromatography with silica using chloroform/hexane (2:1, v/v) as eluent. Dark-red solid: yield 0.16 g, 74.0%; $^1$H NMR ($CDCl_3$, 400.00 MHz) δ 0.87-0.94 (m, 12H), 1.30-1.36 (m, 16H), 1.91-1.95 (m, 2H), 4.04-4.06 (m, 4H), 7.81-7.87 (m, 5H), 8.04-8.10 (m, 5H), 8.31-8.38 (m, 10H), 8.62-8.70 (m, 5H), 8.81 (d, J=4.4 Hz, 4H), 8.95 (s, 4H), 12.68 (broad s, 2H). (MALDI-TOF, m/z) calculated for $C_{86}H_{70}N_6O_8Zn$: 1380.455281 found 1380.442.

Example 5—Preparation of DMCPPH2

In a 100 mL two-neck round-bottom flask, Methyl 4-formylbenzoate (0.5 g, 3.04 mmol), dipyrrolomethane (0.74 g, 3.34 mmol) and dichloromethane (100 mL) were taken and purged with nitrogen for 20 min. After TFA (500 μL) was added and the reaction mixture was stirred for 12 h at room temperature under nitrogen and dark. After 2,3-dichloro-5,6-dicyanobenzoquinone (DDQ) (1.38 g, 6.08 mmol) was added, and the reaction mixture was stirred for 30 min. The reaction was quenched by the addition of triethylamine (5 mL). After completion of reaction, the solvent was removed and the resulted crude product was purified by column chromatography with silica using dichloromethane/hexane (1:1, v/v) as eluent. Purple solid: yield 0.22 g, 10.0%. $^1$H NMR ($CDCl_3$, 400.00 MHz) δ-2.79 (s, 2H), 4.11 (s, 6H), 7.73-7.79 (m, 6H), 8.21 (dd, J=8.0, 1.6 Hz, 4H), 8.30 (d, J=8.0 Hz, 4H), 8.44 (d, J=8.4 Hz, 4H), 8.79 (d, J=4.8 Hz, 4H), 8.87 (d, J=4.4 Hz, 4H). $^{13}$C NMR ($CDCl_3$, 100.00 MHz) δ 52.5, 118.84, 119.03, 126.82, 127.92, 128.00, 131.30, 132.25, 132.46, 134.59, 134.63, 141.97, 141.99, 146.98, 147.00, 167.38.

Example 6—Preparation of ZnDMCPP

A mixture of DMCPPH2 (0.2 g, 0.27 mmol), $Zn(OAc)_22H_2O$ (0.50 g, 2.73 mmol) and $CHCl_3$ (100 mL) was refluxed overnight. After completion of the reaction, solvent was removed and the resulting crude product was purified by column chromatography with silica using chloroform as eluant. Purple solid: yield 0.20 g, 95.0%. $^1$H NMR ($CDCl_3$, 400.00 MHz) δ 4.10 (s, 1H), 7.74-7.81 (m, 6H), 8.22 (d, J=6.4 Hz, 4H), 8.31 (d, J=8.0 Hz, 4H), 8.42 (d, J=8.0 Hz, 4H), 8.90 (d, J=4.8 Hz, 4H), 8.97 (d, J=4.8 Hz, 4H). $^{13}$C NMR ($CDCl_3$, 100.00 MHz) δ 52.39, 119.72, 119.89, 121.53, 121.71, 126.61, 127.62, 127.76, 129.31, 131.61, 131.67, 131.83, 132.27, 132.42, 132.48, 134.42, 134.43, 142.62, 147.69, 149.57, 149.64, 149.71, 150.28, 150.35, 150.43, 167.36.

Example 7—Preparation of ZnDCPP

A mixture of ZnDMCPP (0.10 g, 0.13 mmol) and KOH (0.7 g, 13.00 mmol) in $H_2O$ (10 mL), MeOH (10 mL) and THF (10 mL) was refluxed for 18 h under $N_2$. After completion, the solvents MeOH and THF were removed by flushing with air. The resulting reaction mixture was acidified to pH-5 by adding 1 M HCl. The resulted precipitate was collected by filtration and dried in vacuum for 1 h. Dark-red solid: yield 0.09 g, 91.0%. $^1$H NMR (DMSO-$d_6$, 400.00 MHz) δ 7.80-7.81 (m, 6H), 8.18-8.20 (m, 4H), 8.30-8.38 (m, 4H), 8.78-8.81 (m, 8H) 13.25 (broad s, 2H). (MALDI-TOF, m/z) calculated for $C_{46}H_{28}N_4O_4Zn$: 764.139649 found 764.1386.

Example 8—Preparation of TMCPP

In a 250 mL round bottom flask, methyl 4-formylbenzoate (3.50 g, 21.31 mmol) was dissolved in 50 mL propionic acid. To this mixture, pyrrole (1.62 mL, 23.45 mmol) was added dropwise and the solution was refluxed at 140° C. for 12 h. Then after the reaction mixture was cooled down to room temperature and the resulting purple color precipitate was collected by filtration and washed with methanol and water. Purple solid: yield 2.10 g, 1.2%. $^1$H NMR ($CDCl_3$, 400.00 MHz) δ-2.80 (s, 2H), 4.12 (s, 12H), 8.30 (d, J=8.4 Hz, 8H), 8.46 (d, J=8.0 Hz, 8H), 8.83 (s, 8H).

Example 9—Preparation of ZnTMCPP

A mixture of TMCPP (1.0 g, 1.18 mmol), $Zn(OAc)_2.2H_2O$ (2.59 g, 11.80 mmol) and $CHCl_3$ (100 mL) was refluxed overnight. After completion of the reaction, solvent was removed and the resulting crude product was purified by column chromatography with silica using chloroform as eluant. Purple solid: yield 1.23 g, 92.0%. $^1$H NMR ($CDCl_3$, 400.00 MHz) δ 4.08 (s, 12H), 8.25 (d, J=8.4 Hz, 8H), 8.39 (d, J=8.4 Hz, 8H), 8.81 (s, 8H).

Example 10—Preparation of ZnTCPP

A mixture of ZnTMCPP (0.3 g, 0.33 mmol), KOH (2.63 g, 515.58 mmol) in $H_2O$ (25 mL), MeOH (25 mL) and THF (25 mL) was refluxed for 18 h under $N_2$. Then the clear water solution was acidified to pH=5 by adding 1 M HCl. The resulting precipitate was collected by filtration and dried in vacuum for 1 h. Purple solid: yield 0.25 g, 91.0%. $^1H$ NMR ($CDCl_3$, 400.00 MHz) δ 8.28-8.37 (m, 16H), 8.78 (s, 8H).

Example 11—Preparation of Photocatalytic Systems

A multichannel photochemical reaction system fixed with LED white light (PCX50B, 148.5 mW/$cm^2$) was used as the light source. The PHE evolution experiments were performed in a quartz vial reactor (20 mL) sealed with a rubber septum, gas-closed system, at ambient temperature and pressure. Initially, the prepared sample (10 μM) was dissolved in a mixture of phosphate buffer/THF (9:1 v/v at pH 7.4) and ascorbic acid (AA) (0.4 M) under constant stirring. Then, chloro(pyridine)cobaloxime (CoPyCl) (2.0 mM) cocatalyst was added. The pH was determined by pH meter and adjusted to the required pH using conc. HCl or NaOH. The suspension was purged with argon gas for 15 min to ensure anaerobic conditions and then it was placed in a multichannel photochemical reaction system. After 1 h of irradiation, the released gas (400 μL) was collected by syringe from the headspace of the reactor and was analyzed by gas chromatography (Shimadzu, GC-2014, Japan, with ultrapure Ar as a carrier gas) equipped with a TDX-01(5 Å molecular sieve column) and a thermal conductivity detector (TCD). Eventually, the total content of PHE was calculated according to the standard curve. Continuous stirring was applied to the whole process to keep the photocatalyst particles in suspension state and to achieve uniform irradiation.

The apparent quantum efficiency (AQE) was measured under the similar photocatalytic reaction conditions except using 420 nm OLED light. The focused intensity and illuminated area LED light were ca. 68.0 mW/$cm^2$ and 9.04 $cm^2$, respectively. AQE was calculated via the following equation:

$$AQE = \left(\frac{2 \times \text{number of hydrogen molecules}}{\text{number of incident photons}}\right) \times 100\%$$

The turnover number ($TON$) was calculated by using the following formula;

$$TON = \frac{\text{Number of moles of hydrogen produced in photocatalytic system}}{\text{Number of moles of photocatalyst}}$$

Example 12— Photoelectrochemical Measurement

Photoelectrochemical tests were performed on a three-electrode system using an electrochemical workstation (CHI660C Instruments, China) with Pt wire (counter electrode) and saturated calomel electrode (SCE, reference electrode). The working electrode was fluorine-doped tin oxide (FTO) glass coated with a sample film on the conductive surface. Typically, 2 mg of sample was dissolved in 1 mL of dichloromethane (DCM), and then applied on the conductive surface of FTO glass using drop dispense method. The light source was an LED monochromatic point lamp (3 W, 365 nm). The light spot effective area on the working electrode was set as 28.26 $mm^2$. 8 mL volume of 0.5 M $Na_2SO_4$ aqueous solution acted as the electrolyte. The open-circuit voltages were set as the initial bias voltages in the transient photocurrent response tests.

Example 13— Fluorescence Quantum Yields (t)

The $\Phi O_F$ of the porphyrins in degassed THF solution were calculated by comparing with that of 5,10,15,20-tetraphenylporphyrin (TPP). TPP was used as fluorescence standard ($\lambda_{exe}$=552 nm) with $\Phi_F^{ref}$=0.12 in degassed toluene. The absorbance of the sample and reference solutions was measured by keeping at 0.1 and the emission of the sample and reference solutions was recorded at 552 nm excitation wavelength. The $\Phi_F^{sample}$ was calculated according to the following equation.

$$\Phi_F^{sample} = \Phi_F^{ref}\left(\frac{S_{sample}}{S_{ref}}\right)\left(\frac{A_{ref}}{A_{sample}}\right)\left(\frac{n^2_{sample}}{n^2_{ref}}\right)$$

where $A_{ref}$, $S_{ref}$, $n_{ref}$, and $A_{sample}$, $S_{sample}$, $n_{sample}$ represent the absorbance at the excited wavelength, integrated area under the fluorescence curves and the solvent refractive index of the standard and the sample solutions.

Example 14— Optoelectronic Properties

Figure 2B:
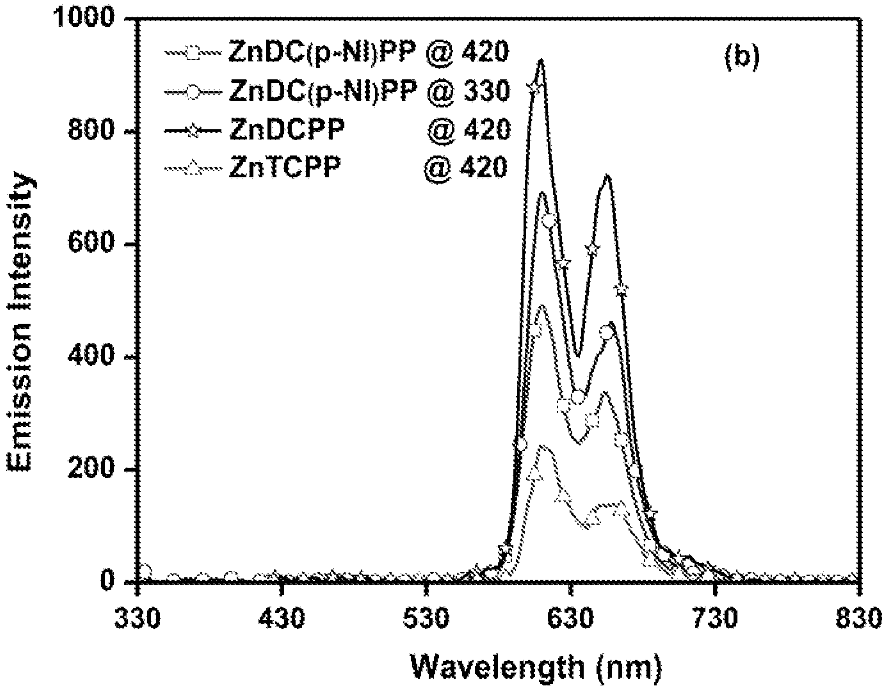
FIG. 2B shows the emission spectra of the porphyrins (ZnDC(p-NI)PP; ZnTCPP and ZnDCPP) recorded in phosphate buffer/THF (9:1 v/v, 10 μM) solution

The absorption and emission spectra of the porphyrins are shown in FIGS. 2A & 2B, respectively and the corresponding data are noted in Table 1. All the porphyrins mainly show two types of peaks. The broad and intensified peaks located at ca. 420-440 nm correspond to the Soret band absorption and the less intensified peaks positioned at ca. 500-650 nm are attributed to the Q-bands absorption. For ZnDC(p-NI)PP porphyrin, the additional peaks at higher energy region (ca. 350 nm) could be ascertained to the NI absorption peaks. Notably, ZnDC(p-NI)PP porphyrin shows apparently higher molar extinction coefficient (s) values for Soret- and Q-bands than the ZnDCPP which lacks the NI groups and ZnTCPP featuring four carboxylic groups. This could be attributed to the conjugation of NI groups to the meso-position of porphyrin donor in A-π-D-π-A architecture which led to elongated it-conjugation and this might have affected the electronic transition probability between the $^1S_0$-$^1Eu$ and $^1S_0$-$^2Eu$ transitions of porphyrin macrocycle. These results clearly speculate that insertion of NI groups on meso-position of porphyrin moiety in A-π-D-π-A molecular design could enhance the light-harvesting ability in the UV-Visible region and consequently expectable good PHE results. Interestingly, ZnDCPP porphyrin with A-π-D-π-A design exhibits higher c values for Soret band than ZnTCPP porphyrin with $(A-\pi)_2$-D-$(\pi-A)_2$ that can also reveal the benefit of the former porphyrin molecular design.

Figure 3:
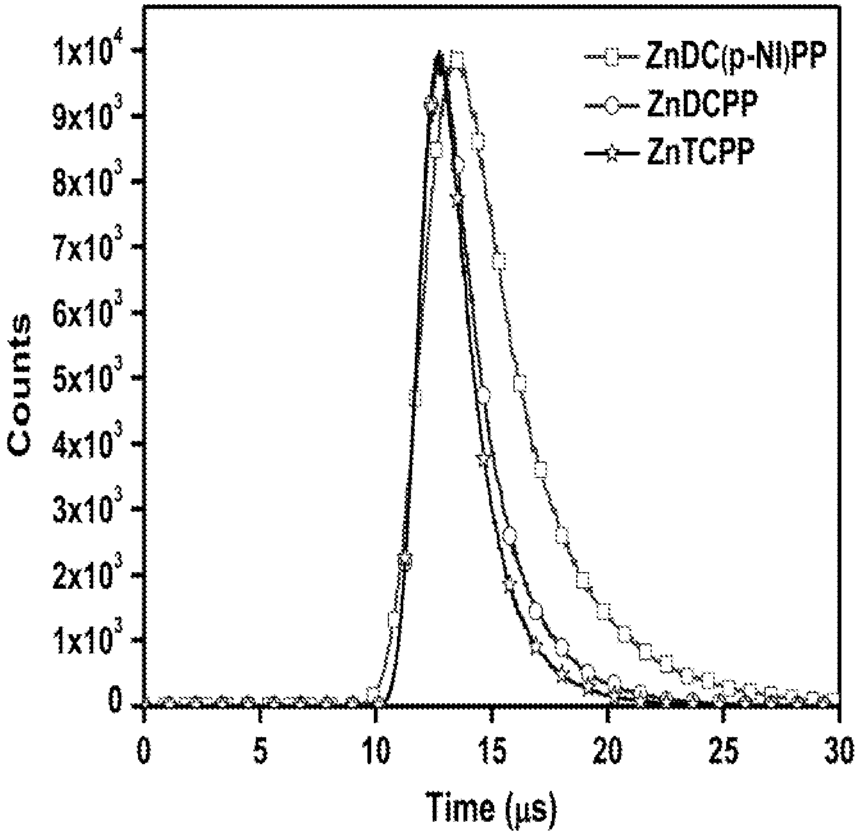
FIG. 3 shows the lifetime decay spectra of the porphyrins (ZnDC(p-NI)PP; ZnTCPP and ZnDCPP) recorded in in phosphate buffer/THF (9:1 v/v, 10 μM) solution at room temperature.

All the porphyrins show two emission peaks (FIG. 2B) in the region of 600-700 nm under excitation of 420 nm which belongs to the Soret band of porphyrin moiety (FIG. 2A). The intensified emission peaks at ca. 610 nm and weak emitting peaks at ca. 660 nm correspond to the Q(0,0) and Q(1,0), respectively of porphyrin macrocycle. Without wishing to be bound by theory it was hypothesized that ZnDC (p-NI)PP porphyrin bearing the NI groups would exhibit IFRET between NI moieties and porphyrin ring. In general, NI derivatives show a very strong emission peak at ca. 450 nm under the excitation of 330 nm which corresponds to NI absorption. So, the relative appearance of NI emission peak intensity in the energy donor-acceptor compounds than NI chromophore emission intensity of free porphyrin gives an insight into how much IFRET occurred between the NI and the porphyrin moieties. In line with this, the appearance of a very weak NI emission peak in the ZnDC(p-NI)PP porphyrin emission spectrum under the excitation of 330 nm corresponds to NI absorption, clearly indicating the efficient IFRET between the NI energy donor and the porphyrin energy acceptor. The calculated IFRET efficiency (ΦET) of ZnDC(p-NI)PP is 99%. Since the fluorescence electron lifetime ($t_F$) of the porphyrins is directly related to the stability of porphyrin excited states, calculation of $t_F$ could give more insight into the porphyrin photoexcited states (FIG. 3). The order of the calculated $t_F$ of the porphyrins is as follows: ZnDC(p-NI)PP (3.8 ns)>ZnDCPP (2.4 ns)>ZnTCPP (1.8 ns). Among the porphyrins, the ZnDC(p-NI)PP porphyrin bearing the NI moieties showed the high $t_F$ which indicates that the ZnDC(p-NI)PP possessing highly stabilized photoexcited states. The highest $t_F$ of ZnDC(p-NI)PP than the ZnDCPP and ZnTCPP could be ascribed to the efficient IFRET between NI and porphyrin moieties. Moreover, the controlled porphyrin, ZnDCPP also shows a higher $t_F$ than the commonly used ZnTCPP. It indicates that the porphyrin with two carboxylic groups possesses longer-lived photoexcited states than the congener porphyrin with four COOH groups. The calculated photoluminescence quantum yield ($\Phi_F$) of the porphyrins is in the order of ZnDC(p-NI)PP (23%)>ZnDCPP (18% ns)>ZnTCPP (16% ns) which is also in line with their $t_F$ trend.

Figure 4:
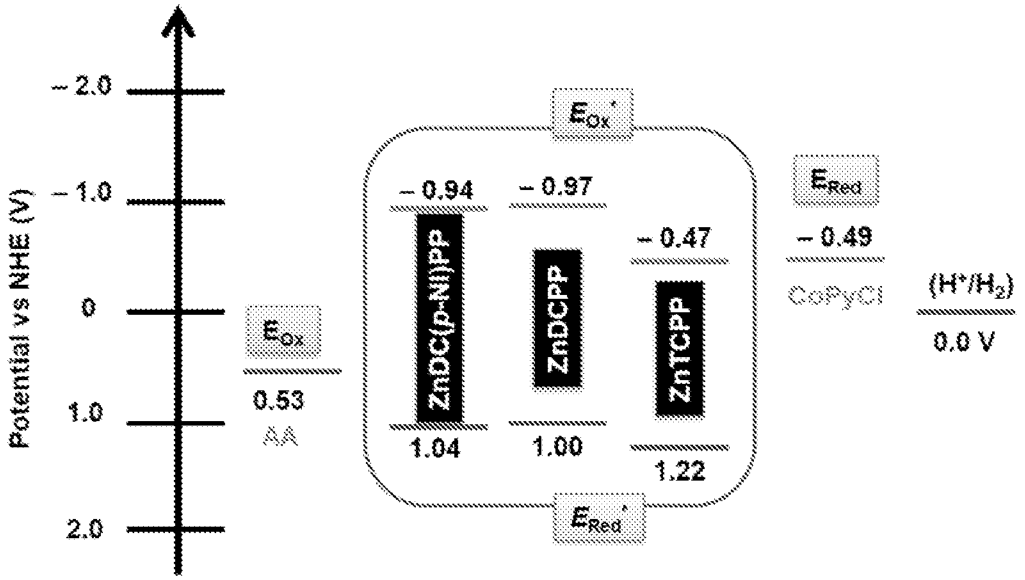
FIG. 4 shows the energy level alignment of the porphyrins (ZnDC(p-NI)PP, ZnTCPP and ZnDCPP), sacrificial donor (AA) and water reduction catalyst (CoPyCl).
Figure 9:
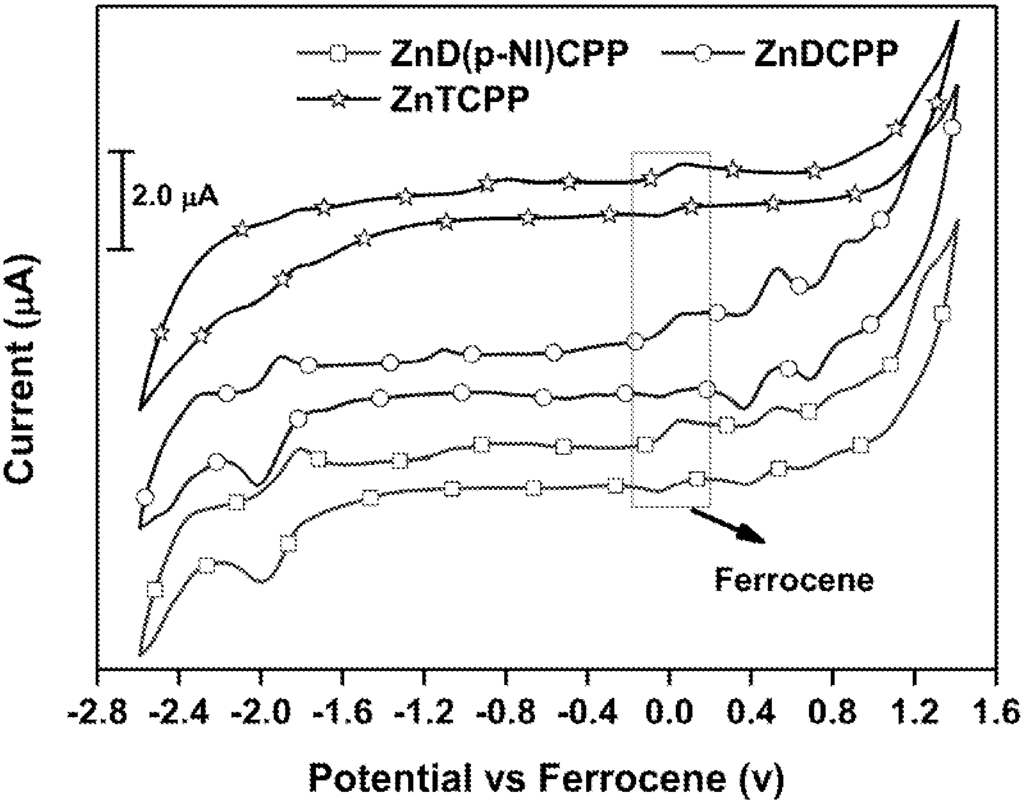
FIG. 9 shows the cyclic voltammograms of the porphyrins (ZnDC(p-NI)PP, ZnTCPP and ZnDCPP) recorded in buffer/THF (9:1 v/v, 100 μM) solution.

The regeneration of oxidized porphyrins by sacrificial electron donor and injection of electrons from photo-excited porphyrins into WRC are two important key steps in the PHE mechanism. These are mainly dependent on the relative energies of the excited state oxidation potentials ($Eo_x$*) and excited state reduction potentials ($E_{Red}$*) of the porphyrins, respectively. Such redox potentials for the porphyrins were evaluated by performing the cyclic voltammetric experiments in buffer/THF solution mixture (FIG. 9). The calculated $Eo_x$* values of ZnDC(p-NI)PP, ZnDCPP and ZnTCPP are— 0.94, — 0.97 and— 0.47, respectively. The values 1.04, 1.00 and 1.22 correspond to the $E_{Red}$* of ZnDC(p-NI)PP, ZnDCPP and ZnTCPP, respectively. As seen in FIG. 4, the $E_{red}$* values of the porphyrins are more positive than the oxidation potential ($Eo_x$) of ascorbic acid (AA) sacrificial electron donor, indicating a favourable thermodynamic driving force for electron transfer from AA to photoexcited porphyrins (PS*). The $Eo_x$* values of porphyrins, ZnDC(p-NI)PP and ZnDCPP are more negative than the reduction potential ($E_{Red}$) of CoPyCl WRC suggesting an effective transfer of electrons from PS* to CoPyCl where proton reception takes place. On the contrary, the $Eo_x$* value of ZnTCPP is similar to the $Eo_x$ of WRC emphasizing an unfavourable transfer of electrons from photoexcited ZnTCPP to WRC. Moreover, the suitable $Eo_x$* and $E_{Red}$* energy levels of ZnDC(p-NI)PP than ZnTCPP may increase the electron injection rate and more sufficient driving force for electron transfer from TEA to PS* and consequently expectable higher PHE efficiency than the ZnTCPP.

TABLE 1

Optical properties of the dyes recorded in THF solution.

| Porphyrin | $\lambda_{abs}$ $(\varepsilon x10^4)^a$ | $\lambda_{em}^b$ | $\Phi_F^c$ | $t_F$ $(ns)^d$ | $E_{Ox}^e(V)$ | $E_{Red}^f(V)$ | $E_{Ox}^{*g}(V)$ | $E_{red}^{*h}(V)$ | $E_{0-0}^i$ |
|---|---|---|---|---|---|---|---|---|---|
| ZnDC(p-NI)PP | 350 (2.18), 426 (35.88), 556 (1.82), 597 (0.78) | 611, 653 | 0.23 | 3.8 | 1.23, 1.53, 1.93 | −1.13 | −0.94 | 1.04 | 2.17 |
| ZnDCPP | 424 (19.66), 556 (0.77), 599 (0.26) | 609, 655 | 0.18 | 2.4 | 1.22, 1.54, 1.91 | −1.19 | −0.97 | 1.00 | 2.19 |
| ZnTCPP | 425 (15.93), 556 (0.72), 599 (0.32) | 610, 660 | 0.16 | 1.8 | 1.68, | −0.93, −1.17 | −0.47 | 1.22 | 2.15 |

[a,b,c,d]Phosphate buffer/THF (9:1 v/v) solution.
[e]$E_{ox}$(vs NHE) = 0.77 + $E_{ox}$ (vs Ferrocene).
[f]$E_{red}$(vs NHE) = 0.77 − $E_{red}$ (vs Ferrocene).
[g]$E_{Ox}^*$ (vs $NHE$) = $E_{Ox} - E_{0-0}$.
[h]$E_{Red}^*$ (vs $NHE$) = $E_{Red} + E_{0-0}$.
[i]Estimated from the intersection of the normalized absorption and emission spectra.

Example 15— PHE Studies

Figure 5A:
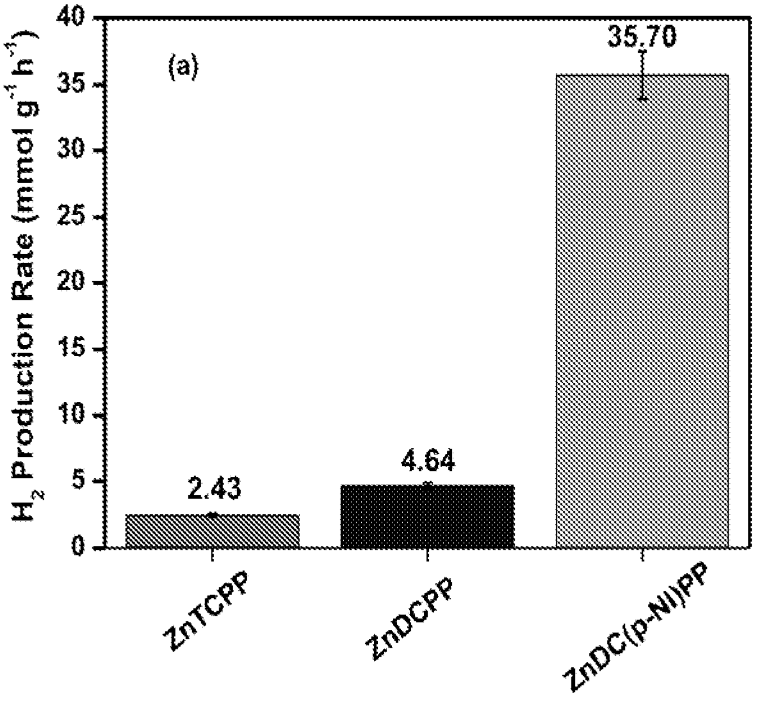
FIG. 5A shows the $H_2$ production rate of photocatalytic systems under the irradiation for 5 h: (Porphyrin; 10 μM (ZnDC(p-NI)PP, ZnTCPP and ZnDCPP)+CoPyCl (2 mM)+AA (0.4 M)+buffer/THF (9:1 v/v) at pH 7.4).
Figure 5B:
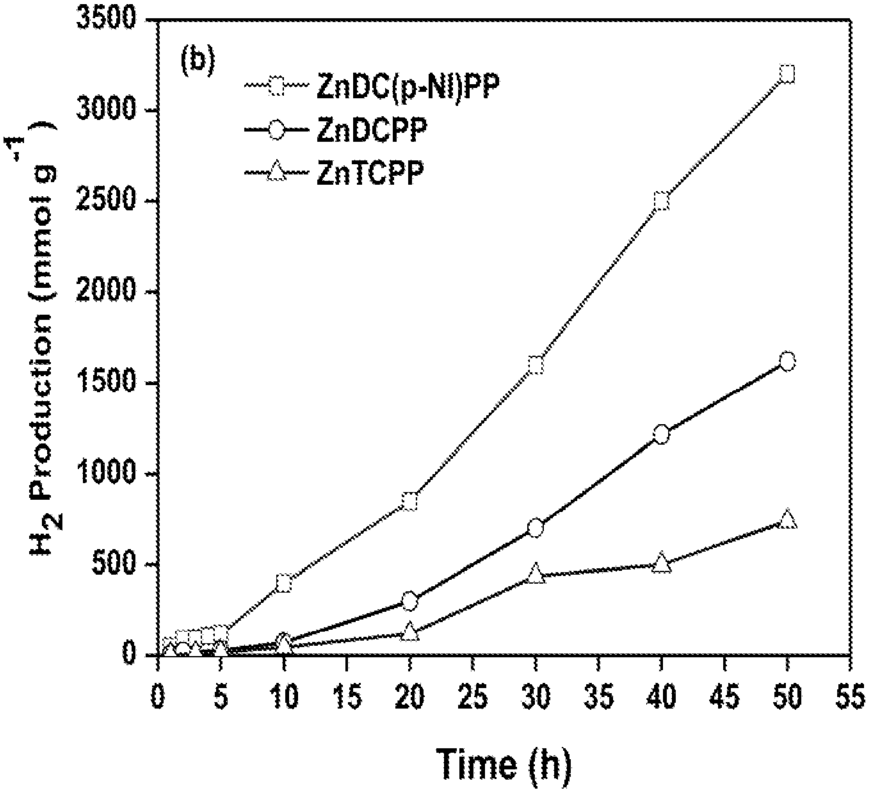
FIG. 5B shows $H_2$ production of photocatalytic systems under the irradiation for 50 h: (Porphyrin; 10 μM (ZnDC(p-NI)PP, ZnTCPP and ZnDCPP)+CoPyCl (2 mM)+AA (0.4 M)+buffer/THF (9:1 v/v) at pH 7.4).

In order to evaluate the PHE properties of porphyrins, a series of homogeneous PSs were prepared in buffer/THF solution by employing porphyrins as photosensitizers, AA as sacrificial electron donor and CoPyCl as WRC. The optimized PHE properties of PSs are shown in FIGS. 5A & 5B and the corresponding data are noted in Table 2. FIG. 5A & 5B shows the hydrogen evolution rate ($\eta H_2$) of the PSs under the illumination of OLED light source for 5 h. From FIG. 5A, it was noticed that A-π-D-π-A based porphyrin, ZnDC(p-NI)PP bearing the NI energy donor moieties on porphyrin donor moiety and COOH groups displayed higher $\eta H_2$ than the ZnDCPP which lacks the NI moieties and well known ZnTCPP porphyrin. The $\eta H_2$ order of PS of the porphyrins is ZnDC(p-NI)PP (35.70 mmol $g^{-1}$ $h^{-1}$) >ZnDCPP (4.64 mmol $g^{-1}$ $h^{-1}$)>ZnTCPP (2.43 mmol $g^{-1}$ $h^{-1}$). The calculated apparent quantum yield (AQE) of ZnDC(p-NI)PP, ZnDCPP and ZnTCPP porphyrins PSs are 10.01, 1.30 and 1.00, respectively. The AQE values of PSs also well match to their $\eta H_2$ order. Furthermore, under the optimized conditions, the photostability of the porphyrins PSs was also evaluated by measuring the PHE up to 50 h of light irradiation. As seen in FIG. 5B, the PHE of three porphyrins PSs was gradually increased with time indicating the good photostability of all components used in PS. The appearance of similar absorption and emission spectra of PSs before and after light irradiation also attests to their good photostability under light (FIG. 15A-16C). The order of turnover number (TON) of porphyrin PSs is as follows:

ZnDC(p-NI)PP (5958), ZnDCPP (1397) and ZnTCPP (562) which is also in line to their $\eta H_2$ and AQE trends. More importantly, the $\eta H_2$ and TON of ZnDC(p-NI)PP PS is superior to the PSs comprising porphyrin photosensitizers and cobaloxime catalysts so far in the literature (Table 3). Particularly, the $\eta H_2$ of ZnDC(p-NI)PP PS is 3.3 times higher than the most efficient PS containing water soluble porphyrin photosensitizer, PorFN (10.9 mmol $g^{-1}$ $h^{-1}$) and Pt WRC reported recently. Moreover, the $\eta H_2$ of ZnDC(p-NI)PP is also much higher than recently reported iridium-conjugated porphyrins and far better than the NI-conjugated porphyrins under heterogeneous conditions with Pt WRC. The superior PHE properties of ZnDC(p-NI)PP possessing the 5,15-di(NI) substituted porphyrin donor moiety than the ZnDCPP which lacks the NI moieties could be explained by the following factors; (i) good light-harvesting properties in the UV—vis region of solar spectrum, (ii) the efficient IET from the NI moieties to the porphyrin ring would stabilize the photoexcited states of porphyrin macrocycle and thus long-lived photoexcited electron lifetimes which further enhances the electron transfer from the photo-excited porphyrin moiety to the CoPyCl WRC through COOH groups, (iii) An efficient acceptance of electrons from AA and subsequent transfer to CoPyCl (vide infra).

Figure 10:
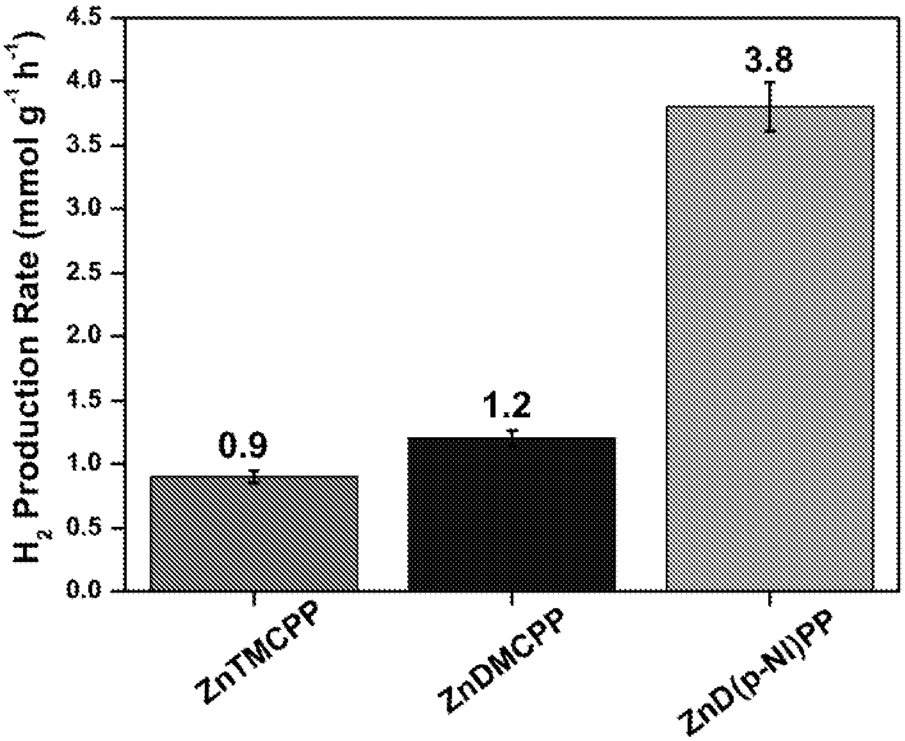
FIG. 10 shows the $H_2$ production rate of photocatalytic systems under the irradiation for 5 h: (Porphyrin; 10 μM (ZnTMCPP, ZnDMCPP and ZnD(p-NI)PP)+CoPyCl (2.0 mM)+AA (0.4 M)+buffer/THF (9:1 v/v) at pH 7.4).

The PS of ZnD(p-NI)PP porphyrin exhibited $\eta H_2$ of 3.8 mmol $g^{-1}$ $h^{-1}$(FIG. 10), which is 10-fold lower than the PS of ZnDC(p-NI)PP. Similarly, the PHE of methylated ZnDCPP and ZnTCPP porphyrins such as ZnDMCPP and ZnTMCPP, respectively were also tested for better comparison. The $\eta H_2$ of ZnDMCPP (1.2 mmol $g^{-1}$ $h^{-1}$) and ZnTMCPP (0.9 mmol $g^{-1}$ $h^{-1}$) is lower than their congener porphyrins, ZnDCPP and ZnTCPP possessing the COOH groups (FIG. 10). This evidence clearly suggests that there would be close contact between COOH of ZnDC(p-NI)PP and CoPyCl in the solution of PS. Thus under light irradiation the photoexcited electrons from ZnDC(p-NI)PP porphyrin to CoPyCl could be transformed easily though COOH groups and consequently higher water reduction.

TABLE 2

Amount of $H_2$ ($\eta H_2$), turnover number (TON) and apparent quantum yield (AQE) for the photocatalytic systems.

| Porphyrin | $\eta H_2^a$ (mmol $g^{-1}$ $h^{-1}$) | TON[b] | AQE[c] |
|---|---|---|---|
| ZnTCPP | 2.43 | 562 | 1.00 |
| ZnDCPP | 4.64 | 1397 | 1.30 |
| ZnDC(p-NIPP | 35.70 | 5958 | 10.01 |

[a,c]Calculated under irradiation for 5 h.

[b]Calculated for 50 h.

TABLE 3

Photocatalytic hydrogen evolution properties of the reported photocatalytic systems comprising porphyrin-based photosensitizer and photocatalyst.

| Photosensitizer | Photocatalyst | $\eta H_2$ (mmol $g^{-1}$ $h^{-1}$) | TON | Irradiating light |
|---|---|---|---|---|
| Zn(PyTBPP)} | {Co(dmgH)$_2$Cl | — | 22 | Xe lamp (300 W) |
| $[ZnTMPyP]^{4+}(Cl^-)_4$, | $[Co^{III}(dmgH)_2(py)Cl]$ | — | 280 | Xe lamp (175 W) |
| $[ZnTMPyP]^{4+}(Cl^-)_4$ | [Co(dmgH)$_2$(N-methyl-imidazole)Cl] | — | 1135 | white LED light (40 W) |
| $[ZnTMPyP]^{4+}(Cl^-)_4$ | Cobalt tetrapyridyl complex (1(BF$_4$)$_2$) | | 18.5 | white LED light |
| PorFN | Pt | 10.90 | — | AM 1.5 G, 100 mW cm$^{-2}$ |
| ZnDC(p-ND)PP | $Co^{III}(dmgH)_2(py)Cl]$ | 35.70 | 5958 | LED white light (148.5 mW/cm$^2$) |

Figure 6:
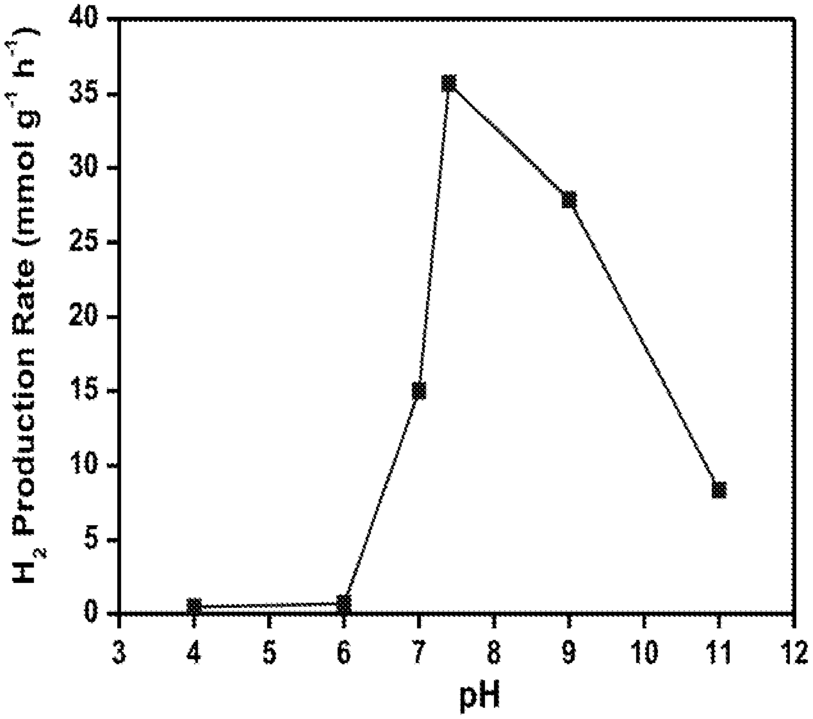
FIG. 6 shows the $H_2$ production rate of photocatalytic systems at different pH under the irradiation for 5 h: (Porphyrin; 10 μM (ZnDC(p-NI)PP)+CoPyCl (2.0 mM)+AA (0.4 M)+buffer/THF (9:1 v/v)).
Figure 11A:
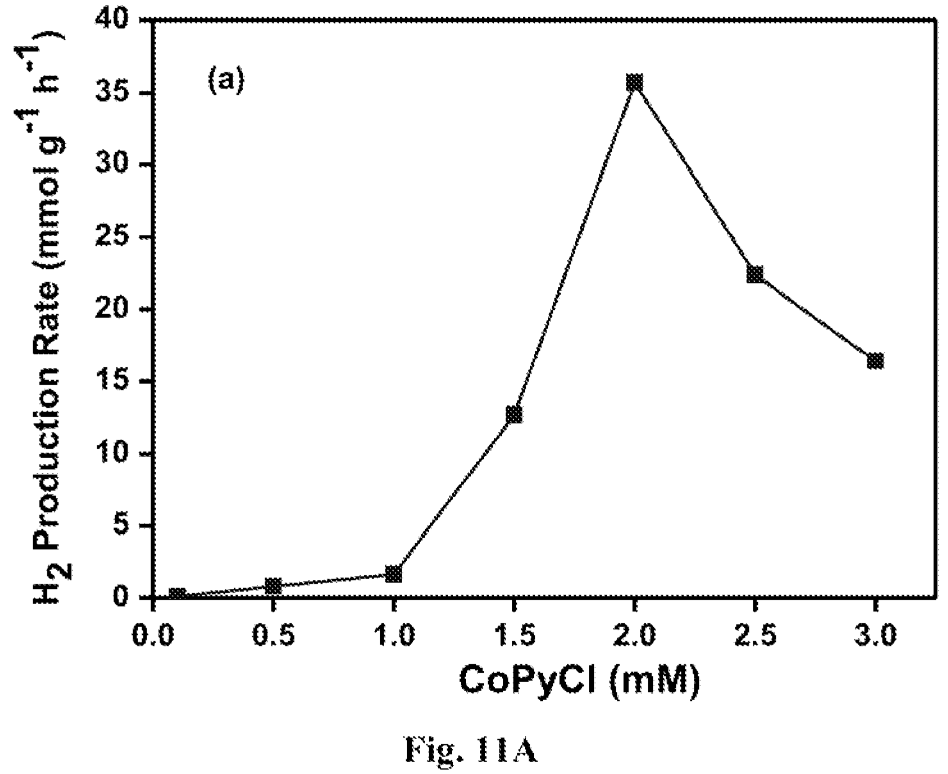
FIG. 11A shows the $H_2$ production rate of photocatalytic systems at different concentration of CoPyCl under the irradiation for 5 h: Porphyrin (ZnDC(p-NI)PP; 10 μM), AA (0.4 M) and buffer/THF (9:1 v/v) at pH 7.4).
Figure 11B:
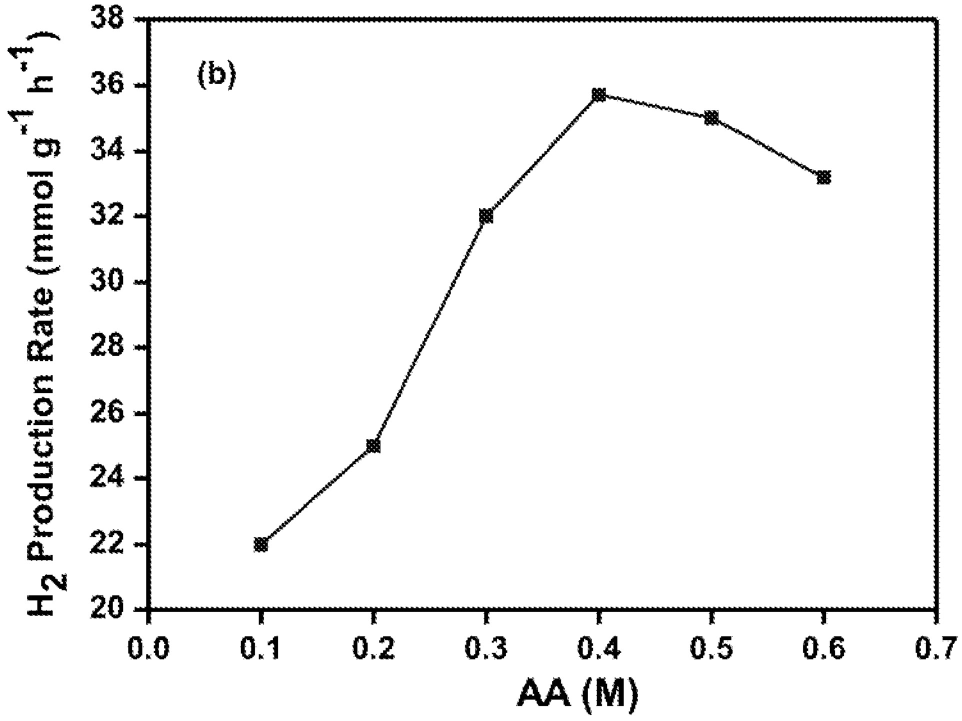
FIG. 11B shows the $H_2$ production rate of photocatalytic systems at different concentration of AA under the irradiation for 5 h: (Porphyrin (ZnDC(p-NI)PP; 10 μM), CoPyCl (0.2 mM) and buffer/THF (9:1 v/v) at pH 7.4).

In order to get more insight into the effect of CoPyCl and AA concentrations on $\eta H_2$, a series of PSs containing ZnDC(p-NI)PP and variable concentrations of CoPyCl and AA were prepared. From FIGS. 11A & 11B, it was observed that the concentration of both CoPyCl and AA has also played an important role to optimize the PSs. For achieving high $\eta H_2$, the PSs must be prepared using 2.0 mM of CoPyCl and 0.4 M of AA. Since PHE of PSs strongly dependent on pH, the PHE of ZnDC(p-NI)PP PS has been evaluated at different pH values. As seen in FIG. 6, the PS of ZnDC(p-NI)PP exhibited the highest $\eta H_2$ of 35.70 mmol $g^{-1}$ $h^{-1}$ at pH=7.4, under likely slightly basic condition. On the contrary, the PSs of ZnDC(p-NI)PP showed a gradual decrease in $\eta H_2$ when pH either increased or decreased with respect to pH=7.4. The declined PHE results of ZnDC(p-NI)PP PS under acidic conditions could be attributed to the degradation of AA which hampers the reducing nature of photoexcited photosensitizer, whereas the rate of formation of active cobalt hydride catalytic intermediate is low under basic conditions and consequently reduces proton reduction.

Figure 7A:
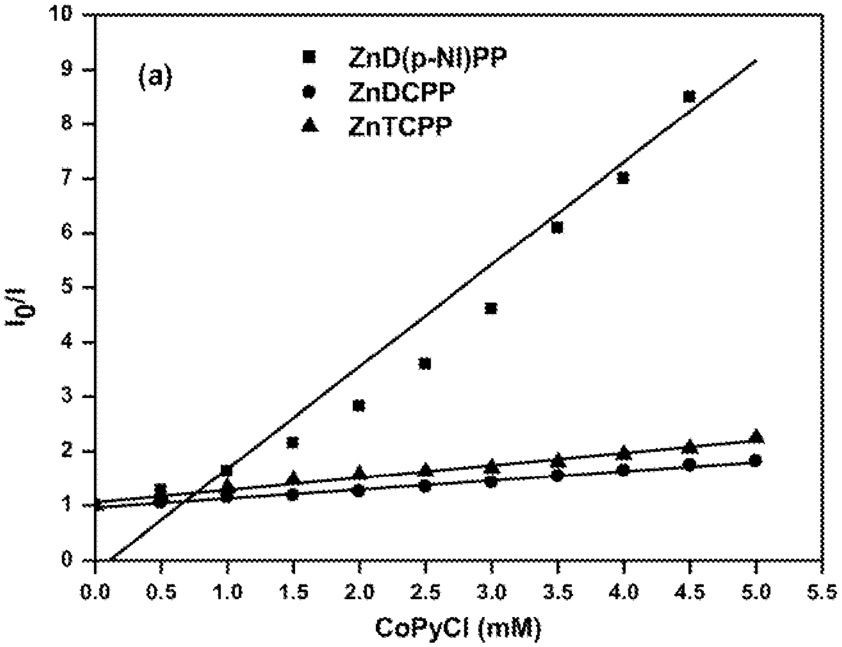
FIG. 7A shows the Stern-Volmer plot of porphyrins; 10 μM (ZnDC(p-NI)PP, ZnTCPP and ZnDCPP) with CoPyCl as quencher in buffer/THF (9:1 v/v) solution.
Figure 7B:
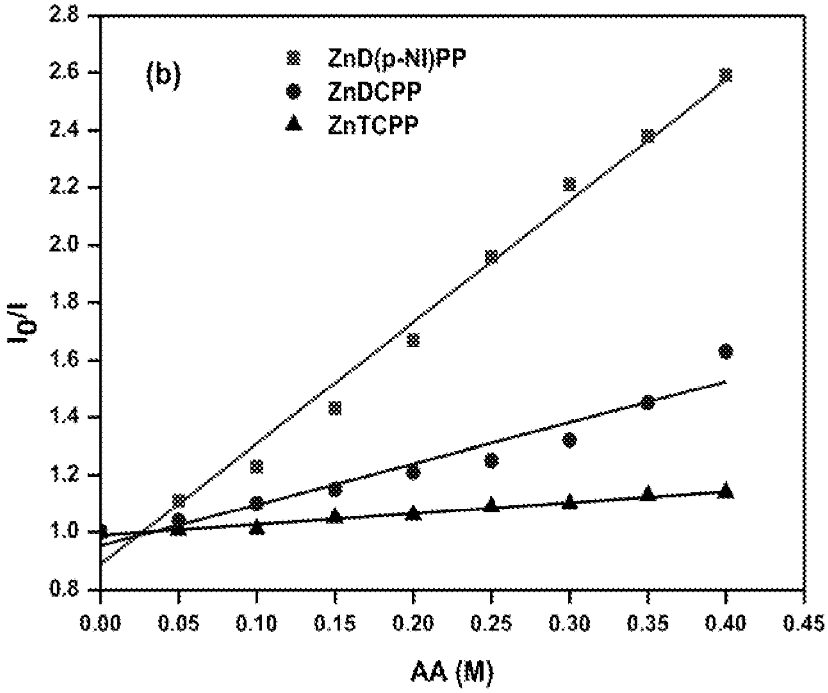
FIG. 7B shows the Stern-Volmer plot of porphyrins; 10 μM (ZnDC(p-NI)PP, ZnTCPP and ZnDCPP) with AA as quencher in buffer/THF (9:1 v/v) solution.
Figure 12A:
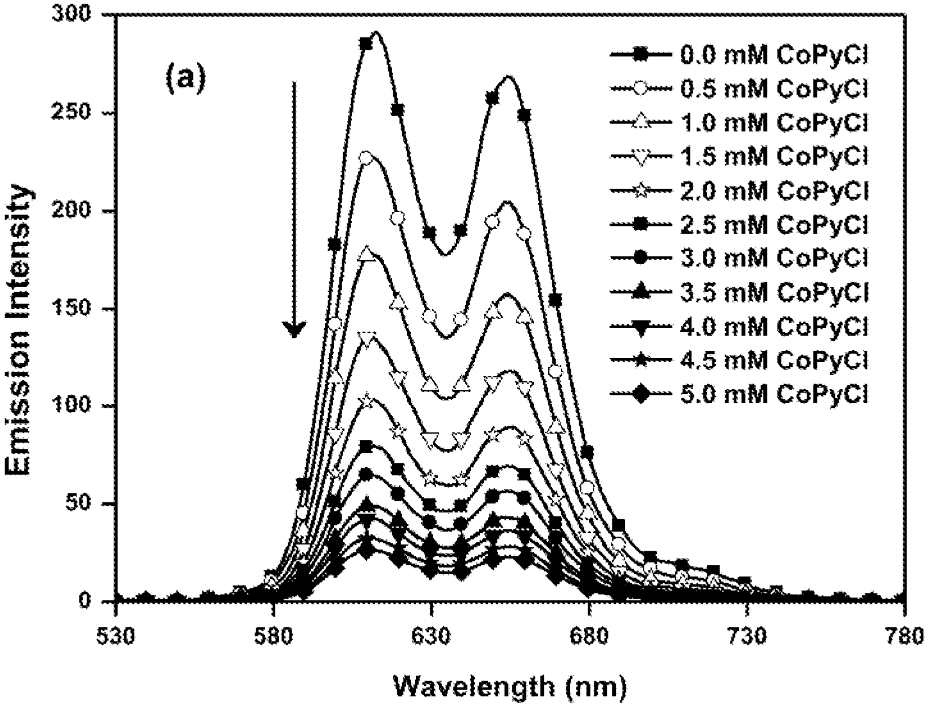
FIG. 12A shows photoluminescence quenching of ZnDC (p-NI)PP (10 μM) with CoPyCl as quencher in phosphate buffer/THF solution
Figure 12B:
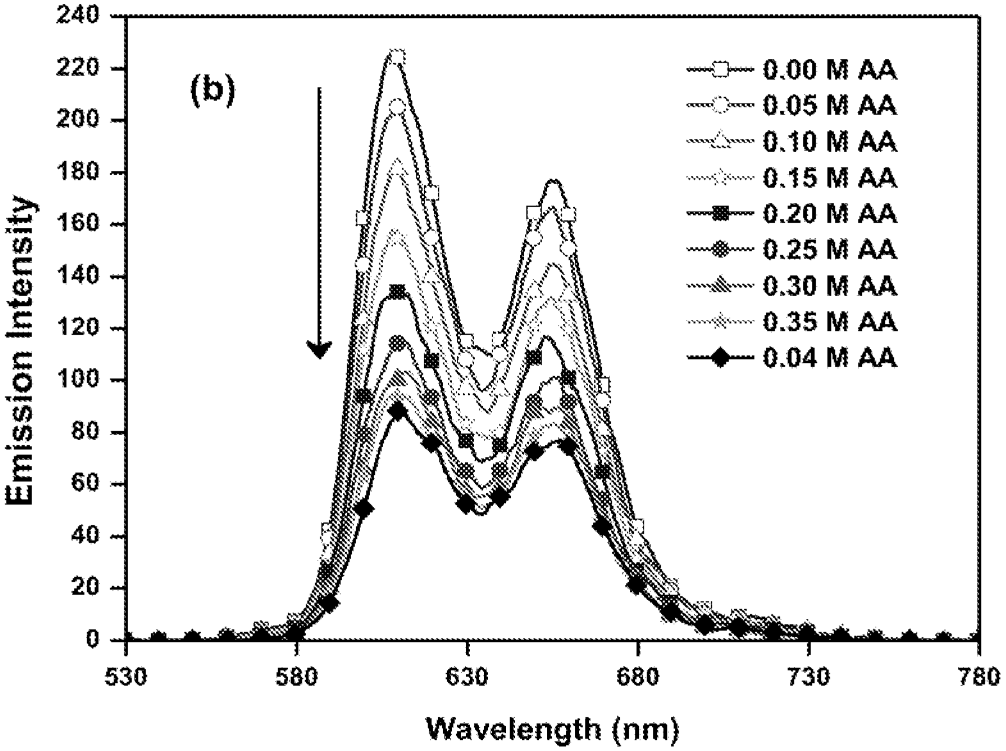
FIG. 12B shows photoluminescence quenching of ZnDC (p-NI)PP (10 μM) with AA as quencher in phosphate buffer/THF solution
Figure 13A:
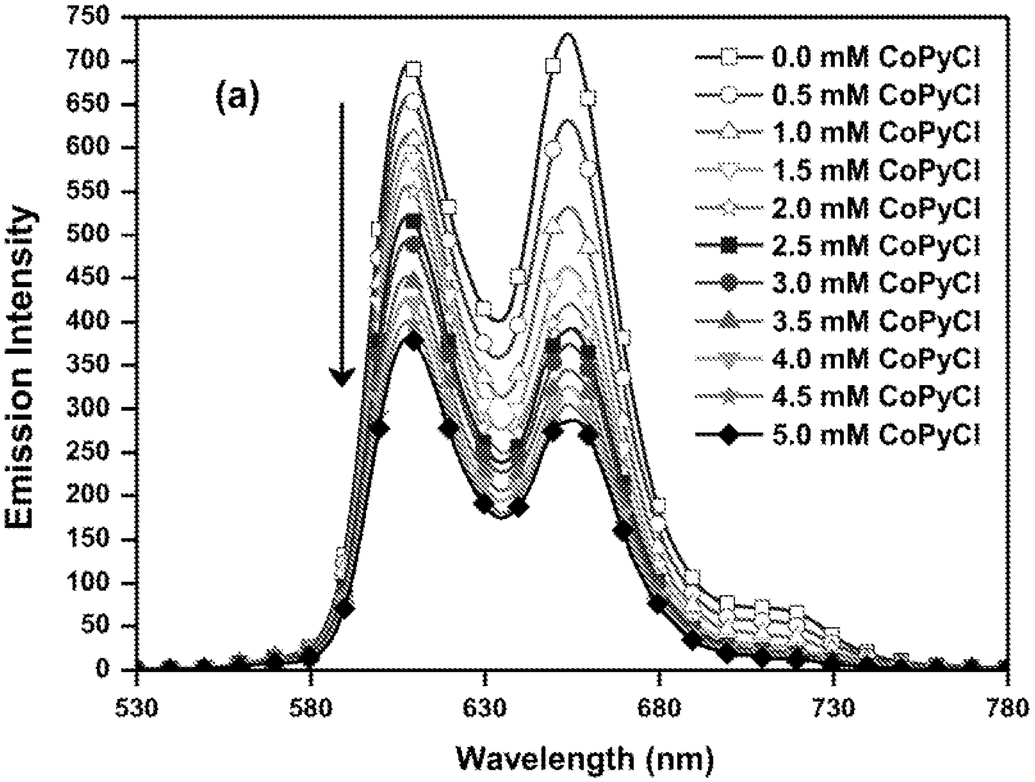
FIG. 13A shows photoluminescence quenching of ZnDCPP (10 μM) with CoPyCl as quencher in phosphate buffer/THF solution
Figure 13B:
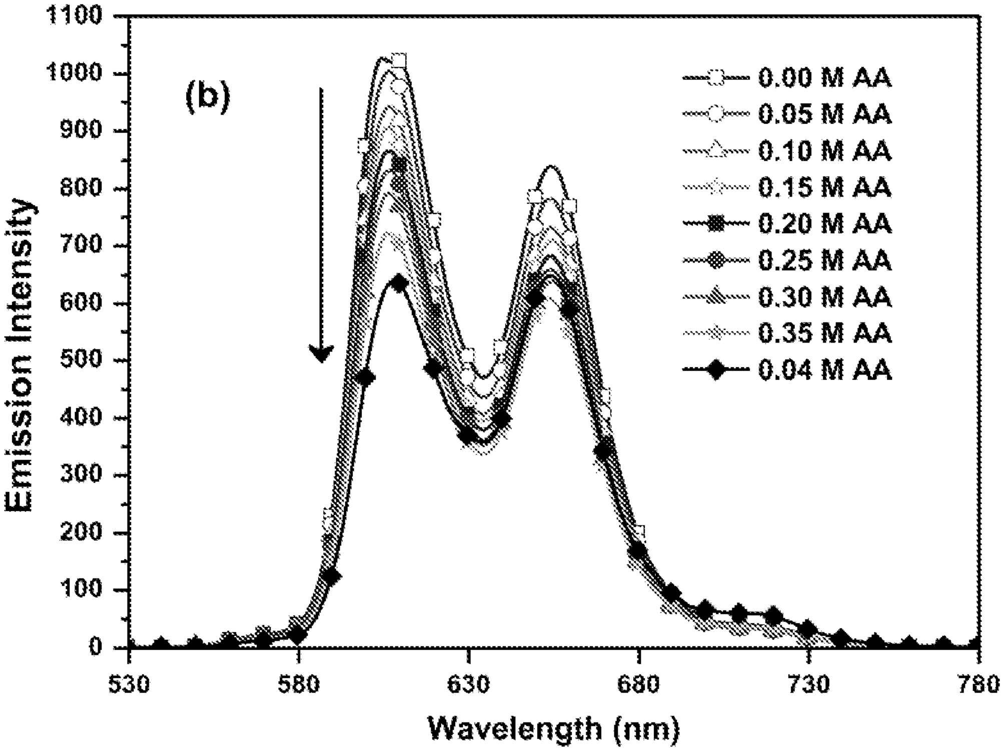
FIG. 13B shows photoluminescence quenching of ZnDCPP (10 μM) with AA as quencher in phosphate buffer/THF solution
Figure 14A:
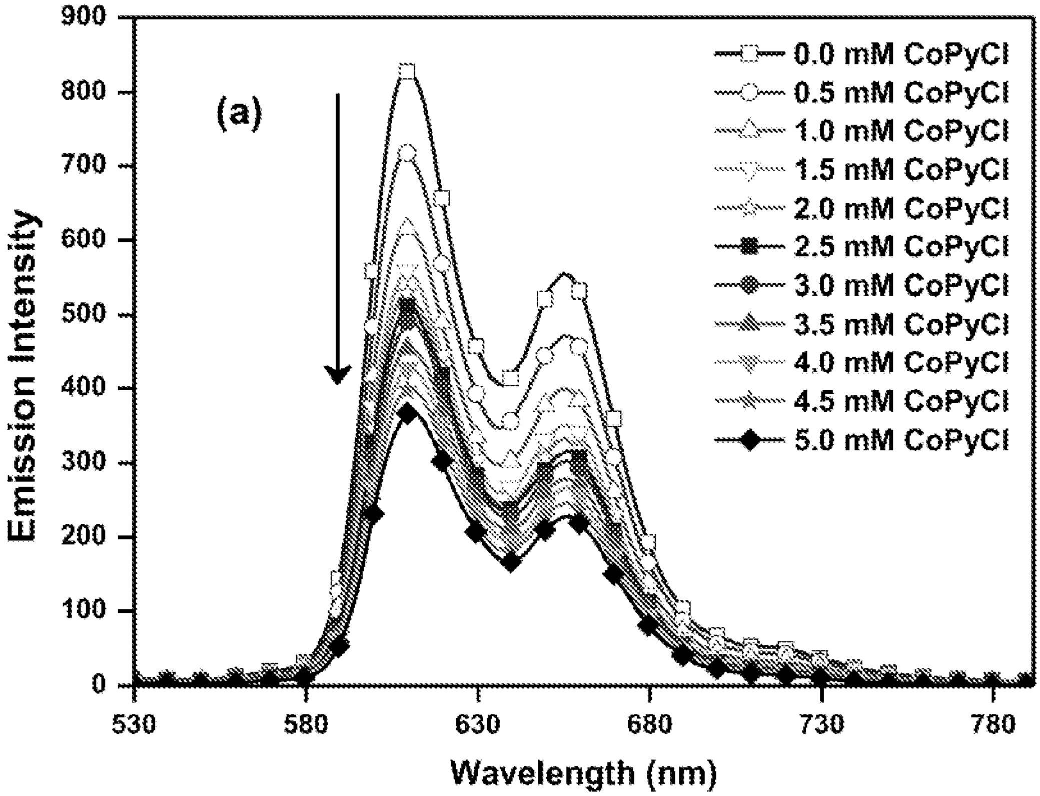
FIG. 14A shows photoluminescence quenching of ZnTCPP (10 μM) with CoPyCl as quencher in phosphate buffer/THF solution.
Figure 14B:
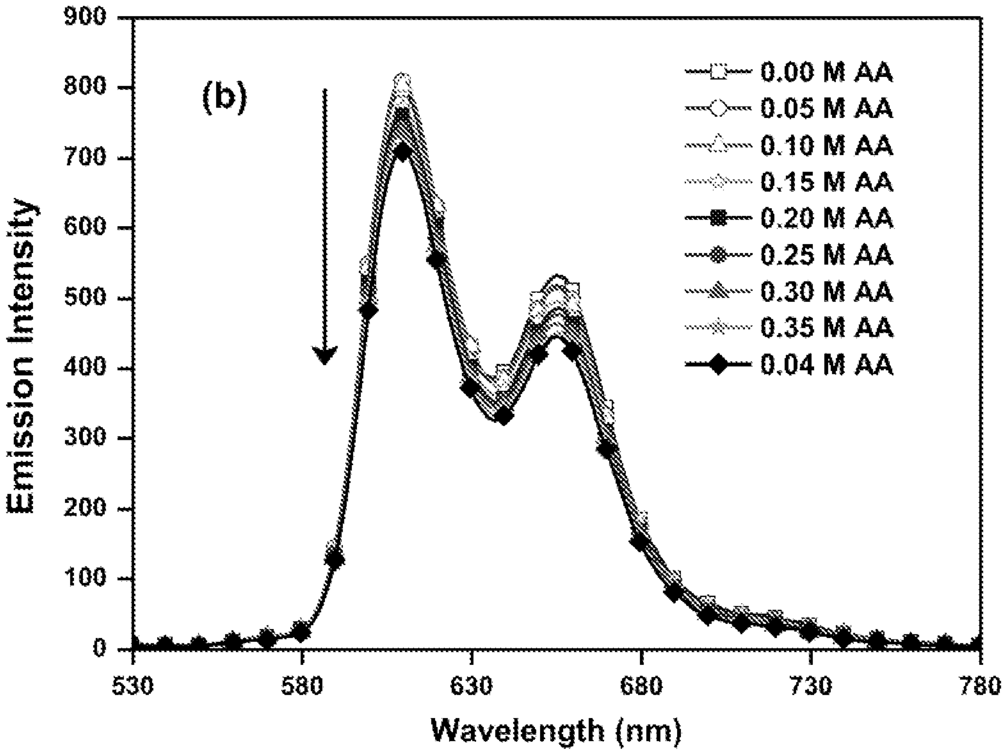
FIG. 14B shows photoluminescence quenching of ZnTCPP (10 μM) with (AA as quencher in phosphate buffer/THF solution
Figure 15A:
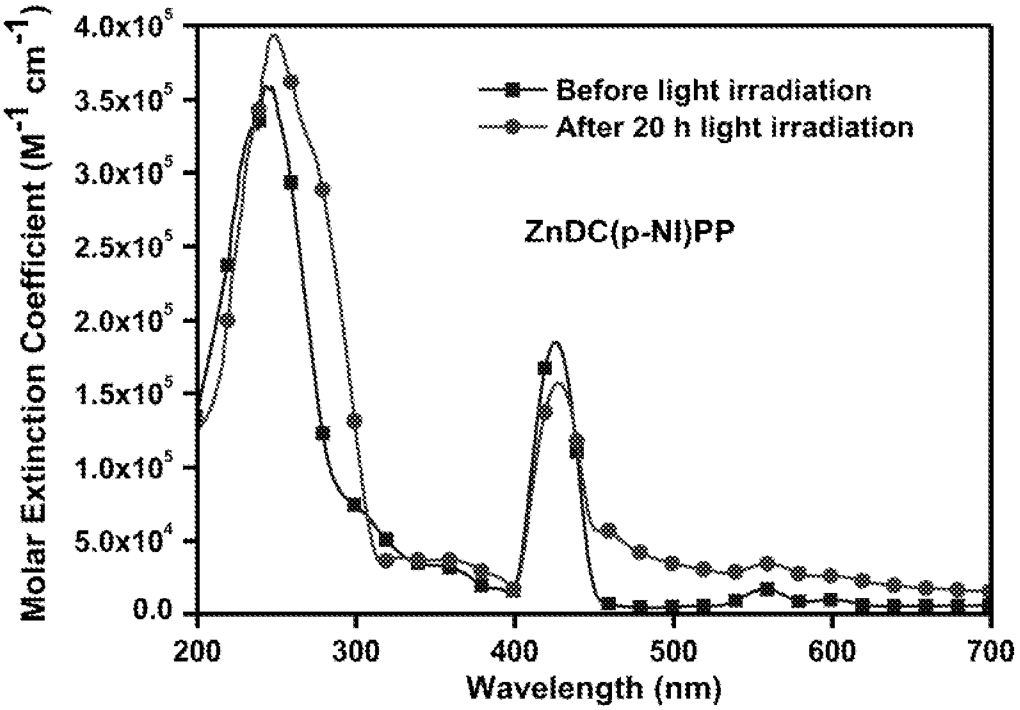
FIG. 15A shows the absorption spectra of photocatalytic systems of ZnDC(p-NI)PP (10 μM) before and after irradiation of light:CoPyCl (2.0 mM), AA (0.4 M) and buffer/THF (9:1 v/v) at pH 7.4.
Figure 15B:
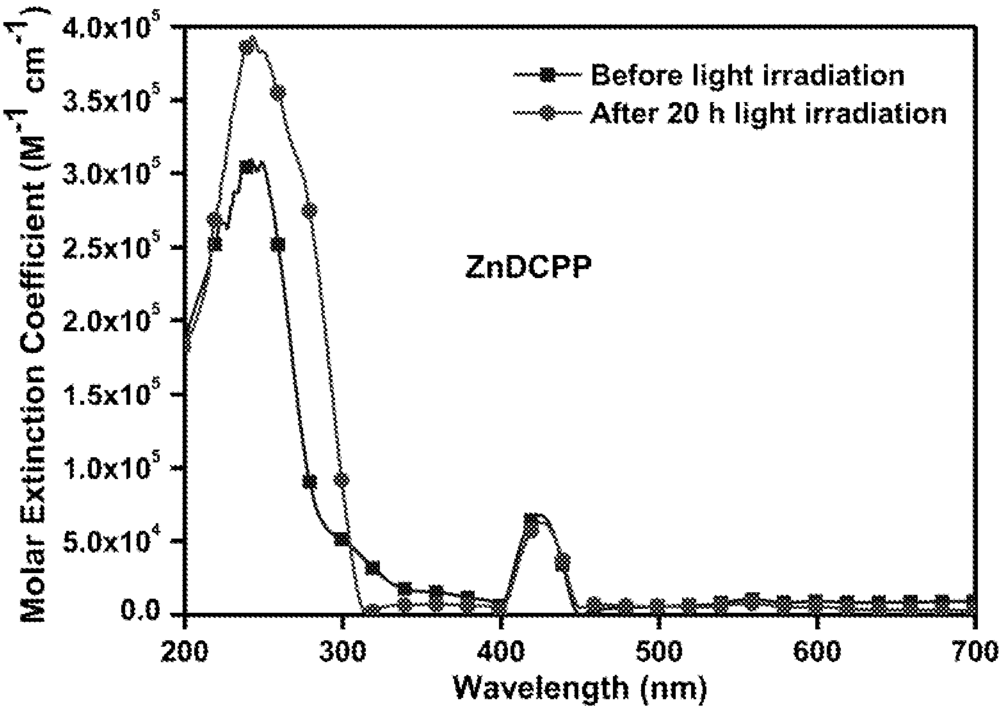
FIG. 15B shows the absorption spectra of photocatalytic systems of ZnDCPP (10 μM) before and after irradiation of light: CoPyCl (2.0 mM), AA (0.4 M) and buffer/THF (9:1 v/v) at pH 7.4.
Figure 15C:
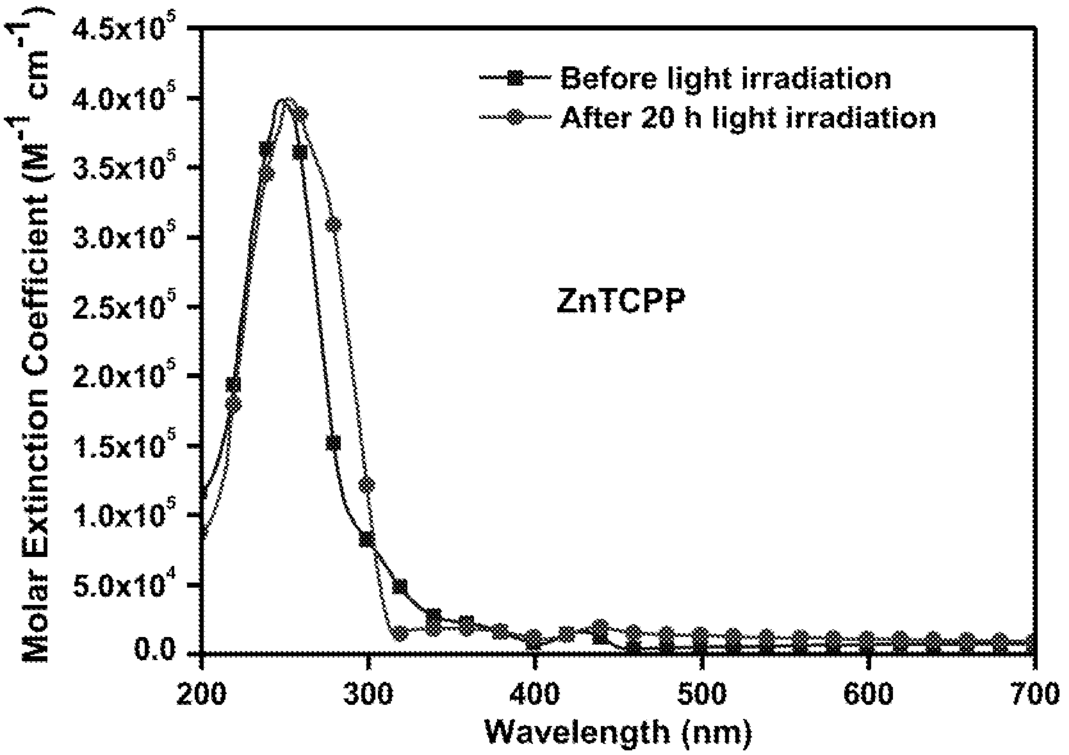
FIG. 15C shows the absorption spectra of photocatalytic systems of ZnTCPP (10 μM) before and after irradiation of light: CoPyCl (2.0 mM), AA (0.4 M) and buffer/THF (9:1 v/v) at pH 7.4.
Figure 16A:
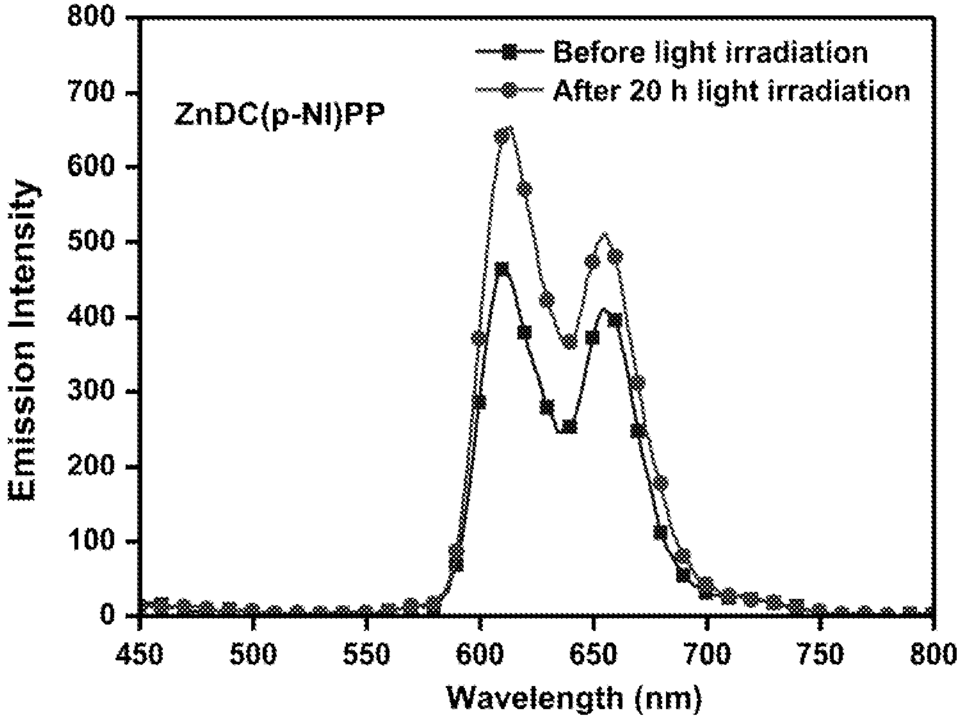
FIG. 16A shows the photoluminescence spectra of photocatalytic systems of ZnDC(p-NI)PP (10 μM) before and after light irradiation: CoPyCl (2.0 mM), AA (0.4 M) and buffer/THF (9:1 v/v) at pH 7.4.
Figure 16B:
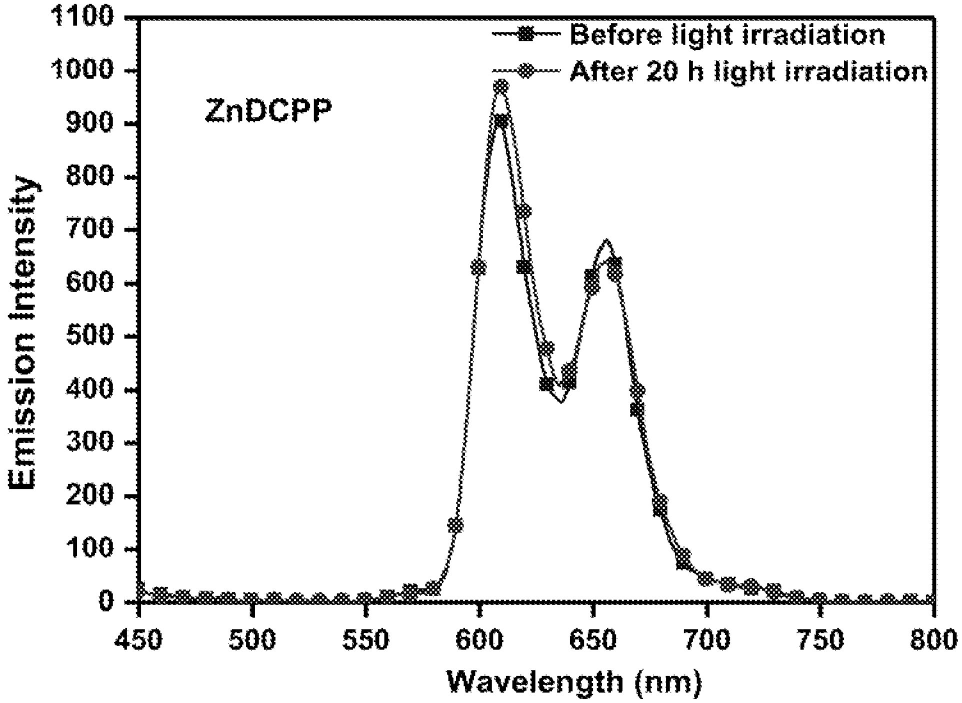
FIG. 16B shows the photoluminescence spectra of photocatalytic systems of ZnDCPP (10 μM) before and after light irradiation: CoPyCl (2.0 mM), AA (0.4 M) and buffer/THF (9:1 v/v) at pH 7.4
Figure 16C:
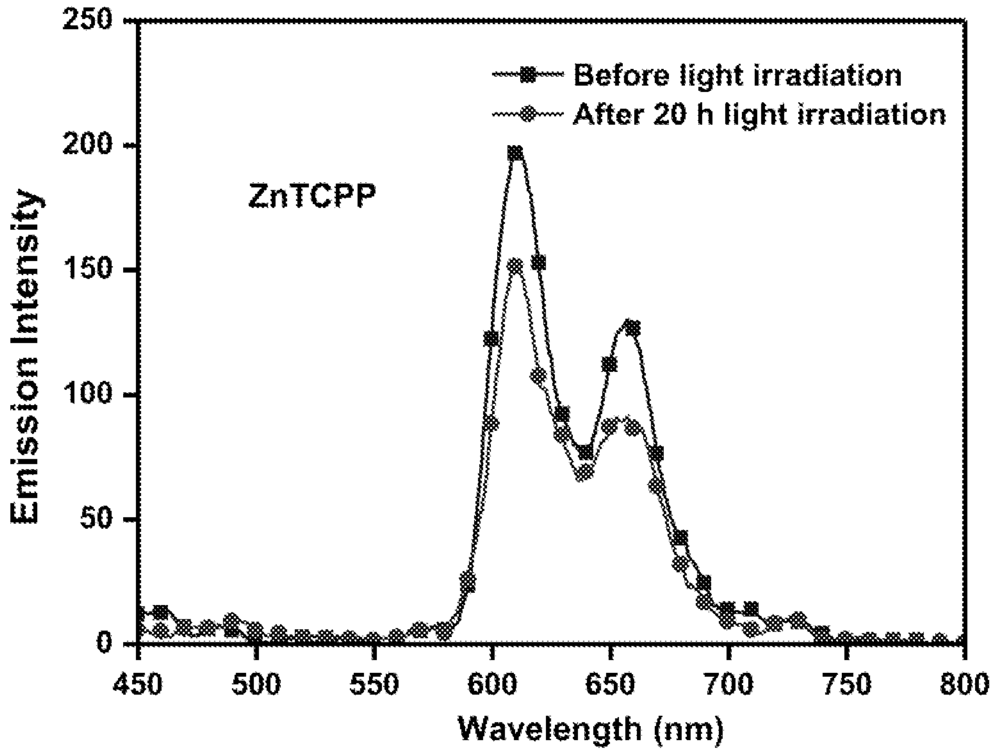
FIG. 16C shows the photoluminescence spectra of photocatalytic systems of ZnTCPP (10 μM) before and after light irradiation: CoPyCl (2.0 mM), AA (0.4 M) and buffer/THF (9:1 v/v) at pH 7.4.

Generally, the electron transfer mechanism involved in homogeneous PHE systems comprising photosensitizer, sacrificial donor and WRC proceeds through either oxidative or reductive quenching pathways. The dominance of quenching type dictates the multistep electron transfer pathway in PSs. The oxidative quenching mechanism involves the transfer of photoexcited electrons of photosensitizer to WRC followed by oxidized photosensitizer reduced back to original ground state by taking electrons from sacrificial donor. In the case of reductive quenching mechanism, the sacrificial donor reduces the excited photosensitizer which further returned to ground state by transferring electrons to WRC where proton reduction takes place. Thus, to understand the type of electron transfer mechanism involved in this PSs, quenching studies using CoPyCl and AA as quenchers (FIG. 12A-14B) were performed. For instance, the fluorescence emission intensity of ZnDC(p-NI)PP is gradually decreased with increasing the concentration of either CoPyCl or AA (FIGS. 12A & 12B). It indicates that the photoexcited ZnDC(p-NI)PP could either efficiently accept an electron from AA or transfer electrons to CoPyCl. The calculated Stern-Volmer quenching constants ($K_q$) of ZnDC(p-NI)PP are $1.9\times10^2$ $M^{-1}s^{-1}$ and 4.2 $M^{-1}s^{-1}$ for quenchers CoPyCl and AA, respectively (FIGS. 7A & 7B). However, given the high concertation of AA (0.4 M) than the CoPyCl (2.0 mM) used in the PSs, the calculated oxidative and reductive quenching rates of ZnDC(p-NI)PP are $38\times10^2$ $s^{-1}$ and $168\times10^2$ $s^{-1}$, respectively. Since the reductive quenching rate is 5 times higher than the oxidative quenching rate, the reductive quenching mechanism was assigned to the current PSs. Accordingly, the calculated oxidative quenching rates of ZnDCPP and ZnTCPP are $1.6\times10^{-2}$ and $4.6\times10^{-2}$ $s^{-1}$, respectively whereas the values $0.57\times10^{-4}$ and $0.15\times10^{-4} s^{-1}$ correspond to quenching rates of ZnDCPP and ZnTCPP porphyrins, respectively. The reductive quenching rate order of porphyrins is ZnDC(p-NI)PP>ZnTCPP>ZnDCPP whereas the order, ZnDC(p-NI)PP>ZnDCPP>ZnTCPP represents the oxidative quenching rates of the porphyrins. These quenching rate orders reveal that the ZnDC(p-NI)PP porphyrin can efficiently accepts electrons from AA, which further quickly donates to CoPyCl than the control porphyrins ZnDCPP and ZnTCPP. This result is also well consistent with higher PHE results for ZnDC(p-NI)PP PS than the PSs of ZnDCPP and ZnTCPP porphyrins.

Figure 8:
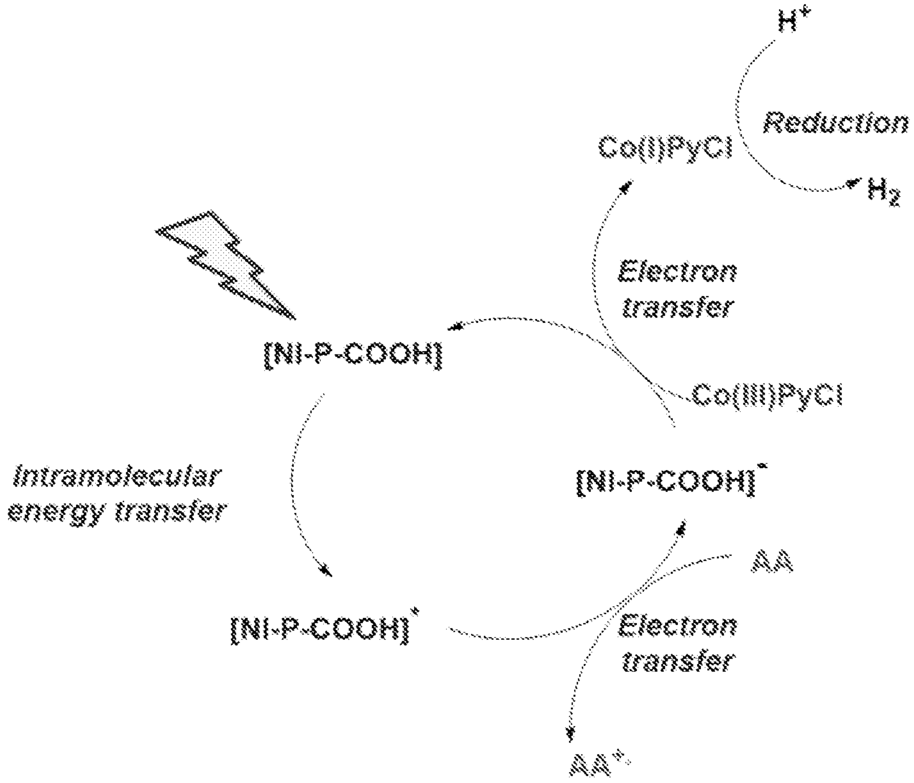
FIG. 8 shows the schematic illustration of photo-redox cycle mechanism for PHE with ZnDC(p-NI)PP, where NI—P—COOH represents ZnDC(p-NI)PP.

Based on the optoelectronic, PHE and Stern-Volmer quenching studies, a schematic illustration of electron transfer mechanism has been proposed for the photo-redox cycle for hydrogen production (FIG. 8). Upon light irradiation on NI containing ZnDC(p-NI)PP porphyrin (denoted NI—P—COOH), the photoexcited NI moiety transfers energy to porphyrin ring through IFRET process, followed by the formation of photoexcited porphyrin complex [NI—P—COOH]*. This complex then accepts an electron from AA resulting in reduced $[NI—P—COOH]^-$ species which further donate two electrons to Co(III)PyCl to give reduced Co(I)PyCl. Finally, the resulting Co(I) species ultimately reduces protons to hydrogen.

Figure 17:
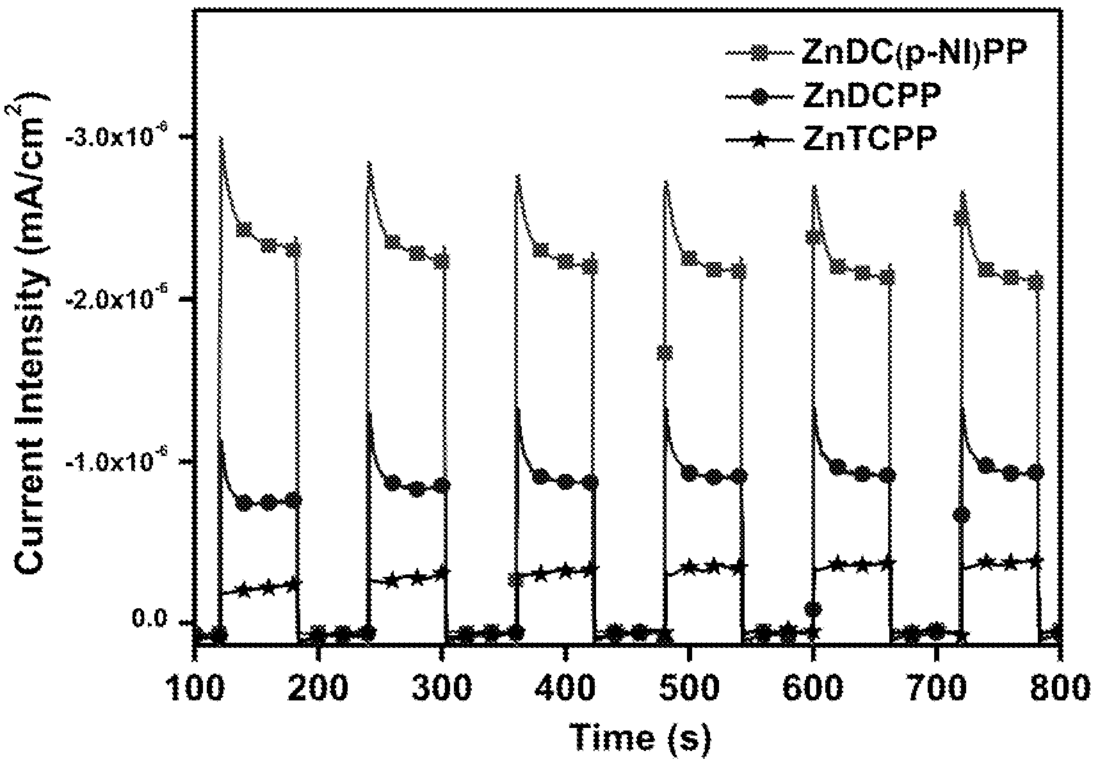
FIG. 17 shows the photocurrent response spectra of the porphyrins of ZnDC(p-NI)PP, ZnDCPP and ZnTCPP.
Figure 18:
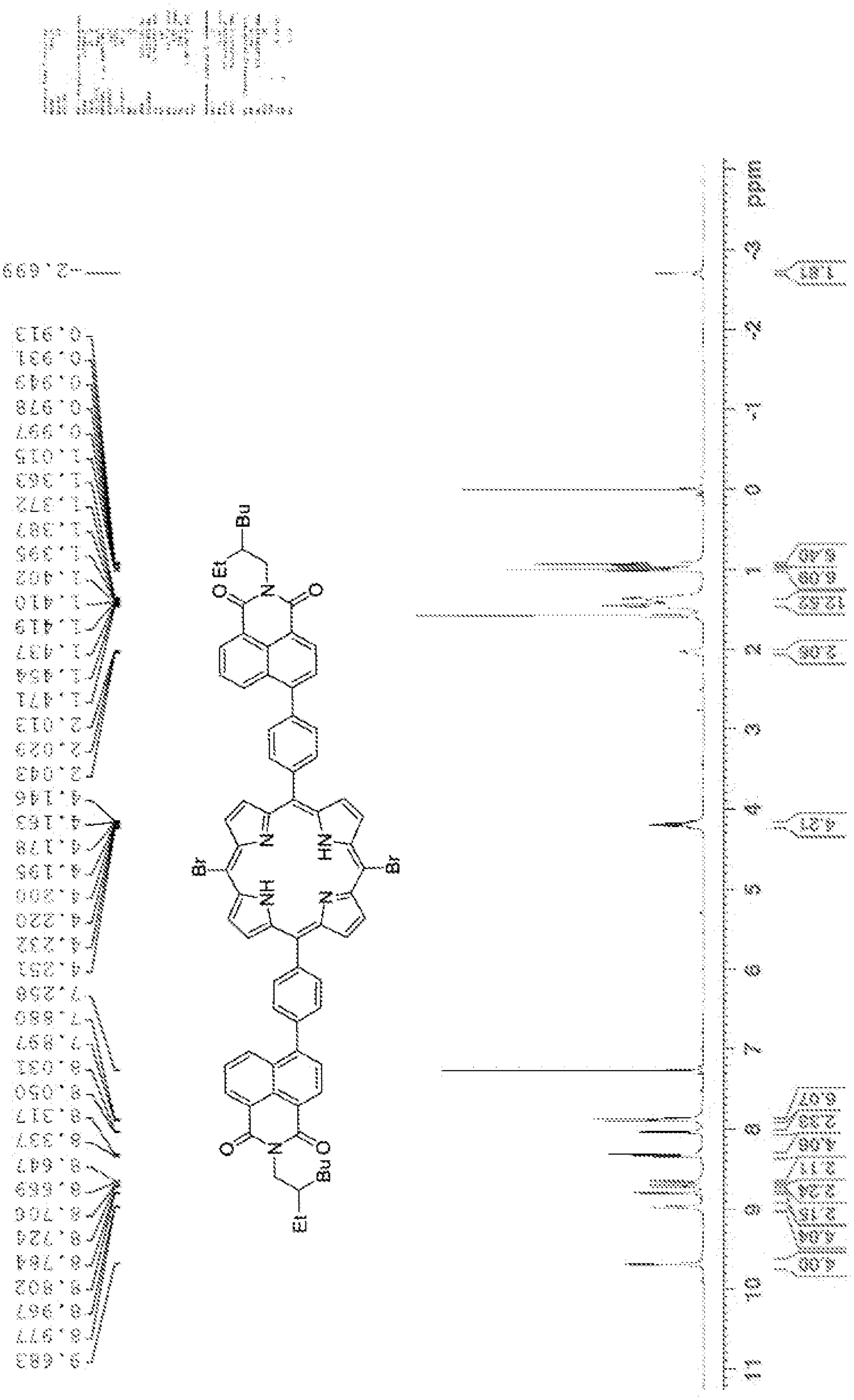
FIG. 18 shows the $^1H$ NMR spectra of DiBrD(p-NI)PPH2 recorded in $CDCl_3$.
Figure 19:
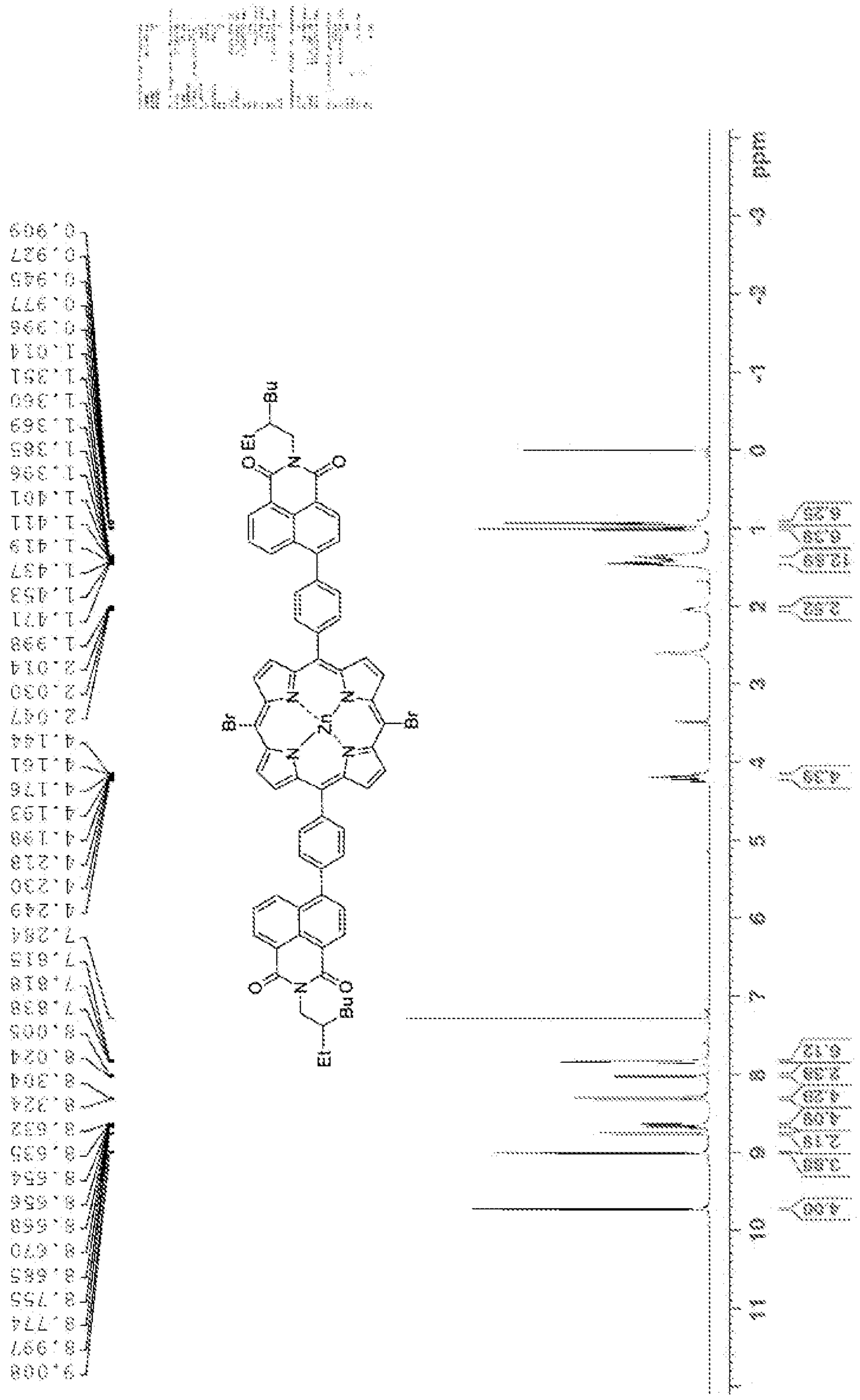
FIG. 19 shows the $^1H$ NMR spectra of DiBrZnD(p-NI) PPH2 recorded in $CDCl_3$.
Figure 20:
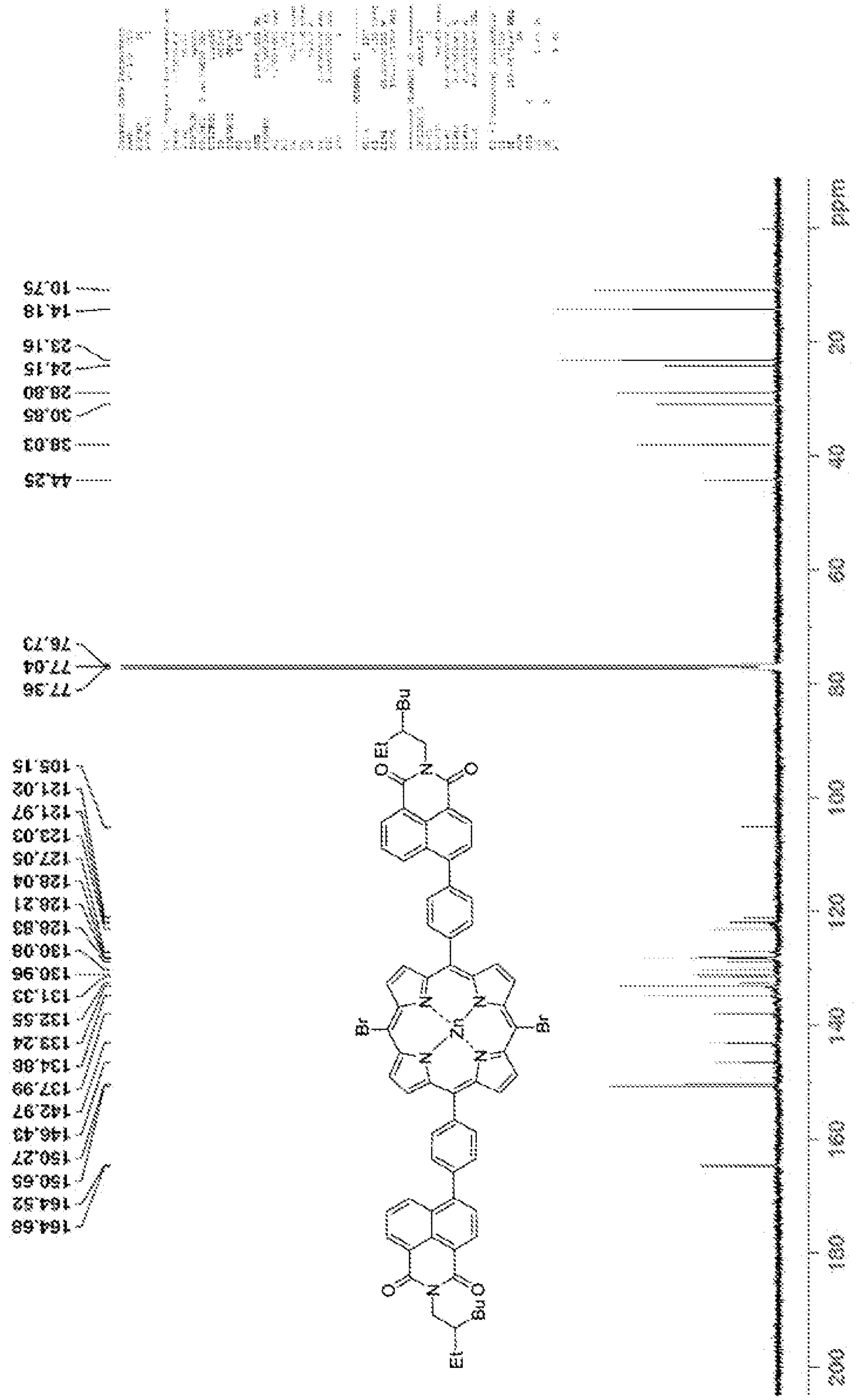
FIG. 20 shows the $^{13}C$ NMR spectra of DiBrZnD(p-NI) PPH2 recorded in $CDCl_3$.
Figure 21:
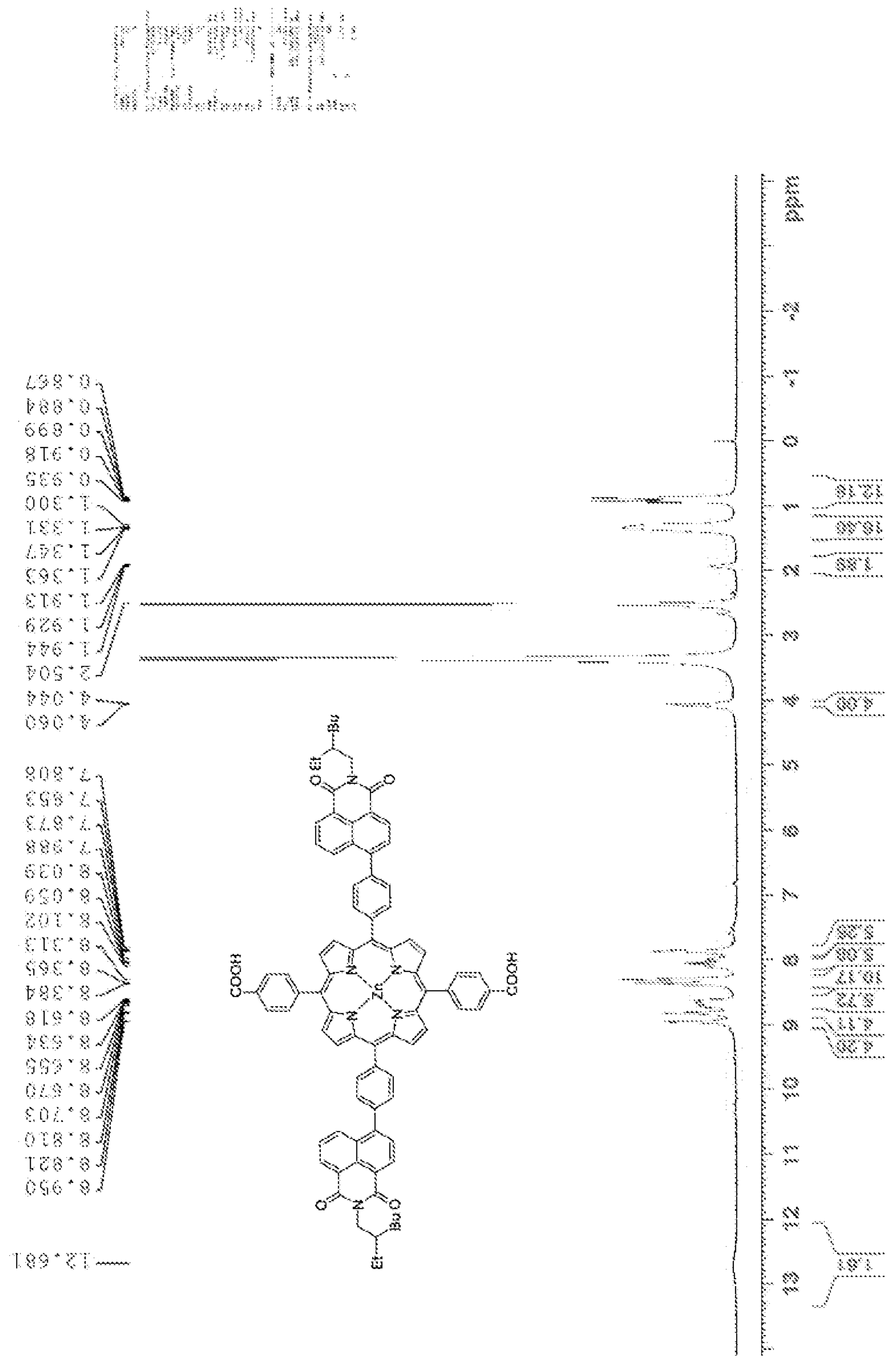
FIG. 21 shows the $^1H$ NMR spectra of ZnDC(p-NI)PP recorded in DMSO-$d_6$.
Figure 22:
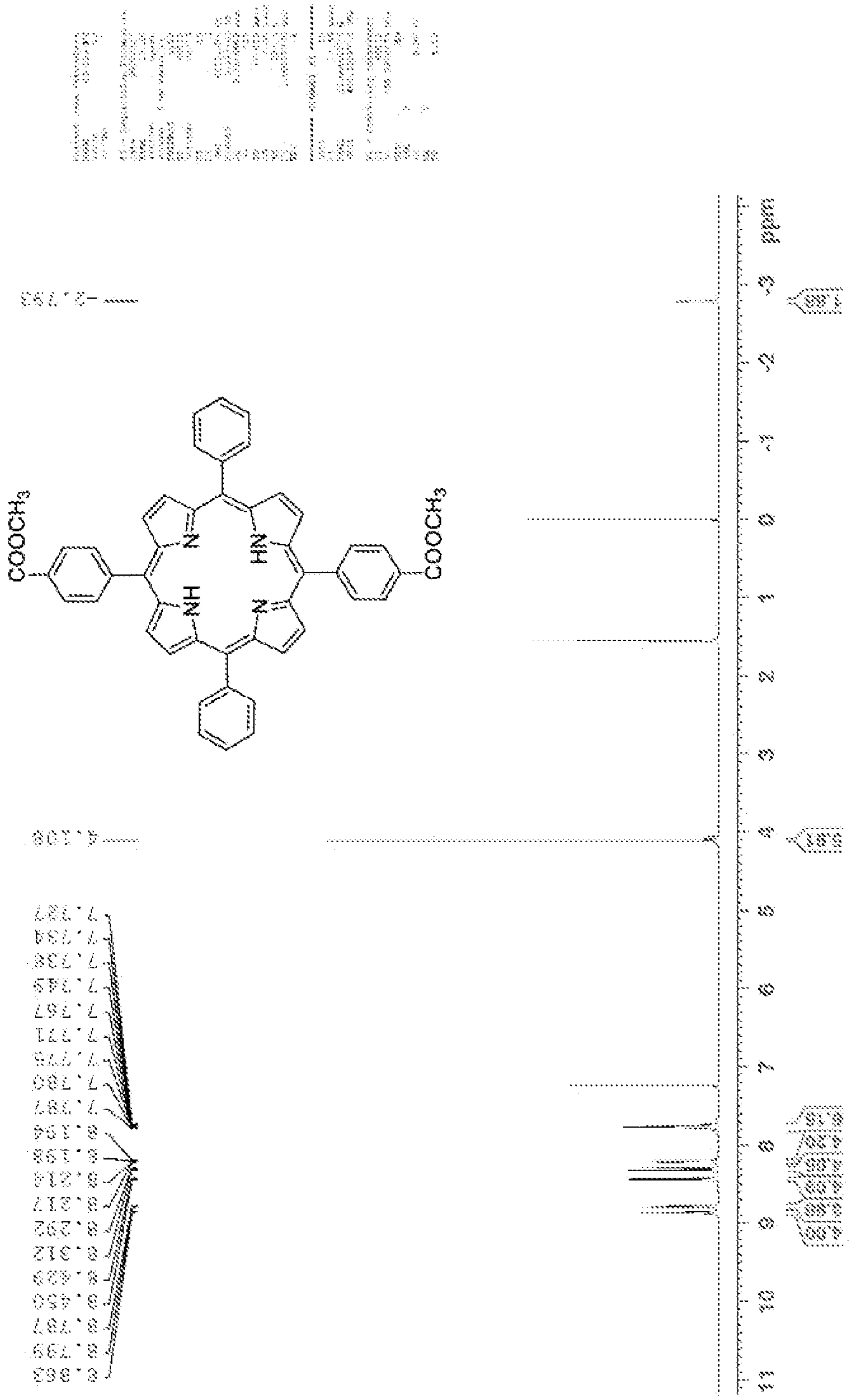
FIG. 22 shows the $^1H$ NMR spectra of DMCPPH2 recorded in $CDCl_3$.
Figure 23:
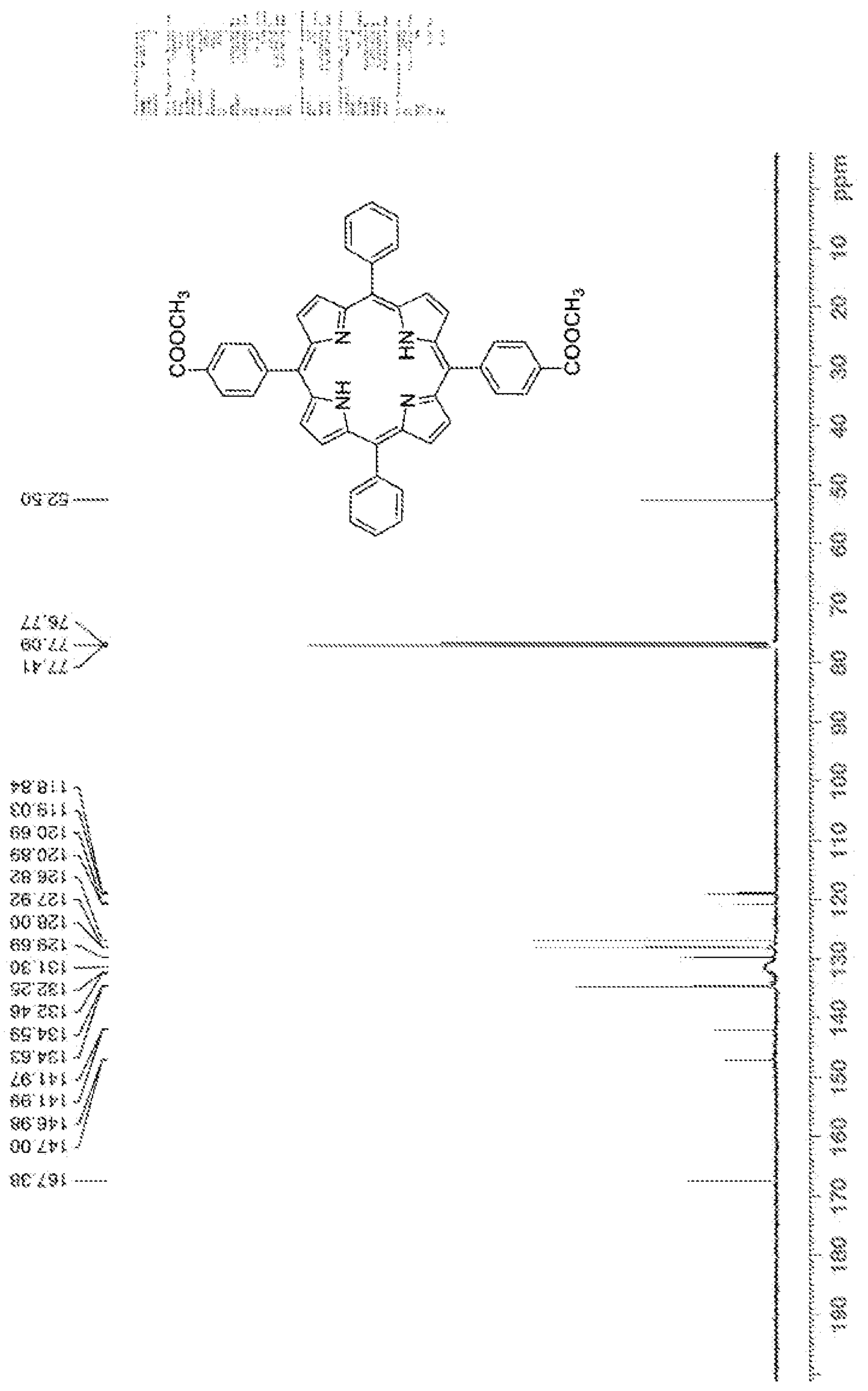
FIG. 23 shows the $^{13}C$ NMR spectra of DMCPPH2 recorded in $CDCl_3$.
Figure 24:
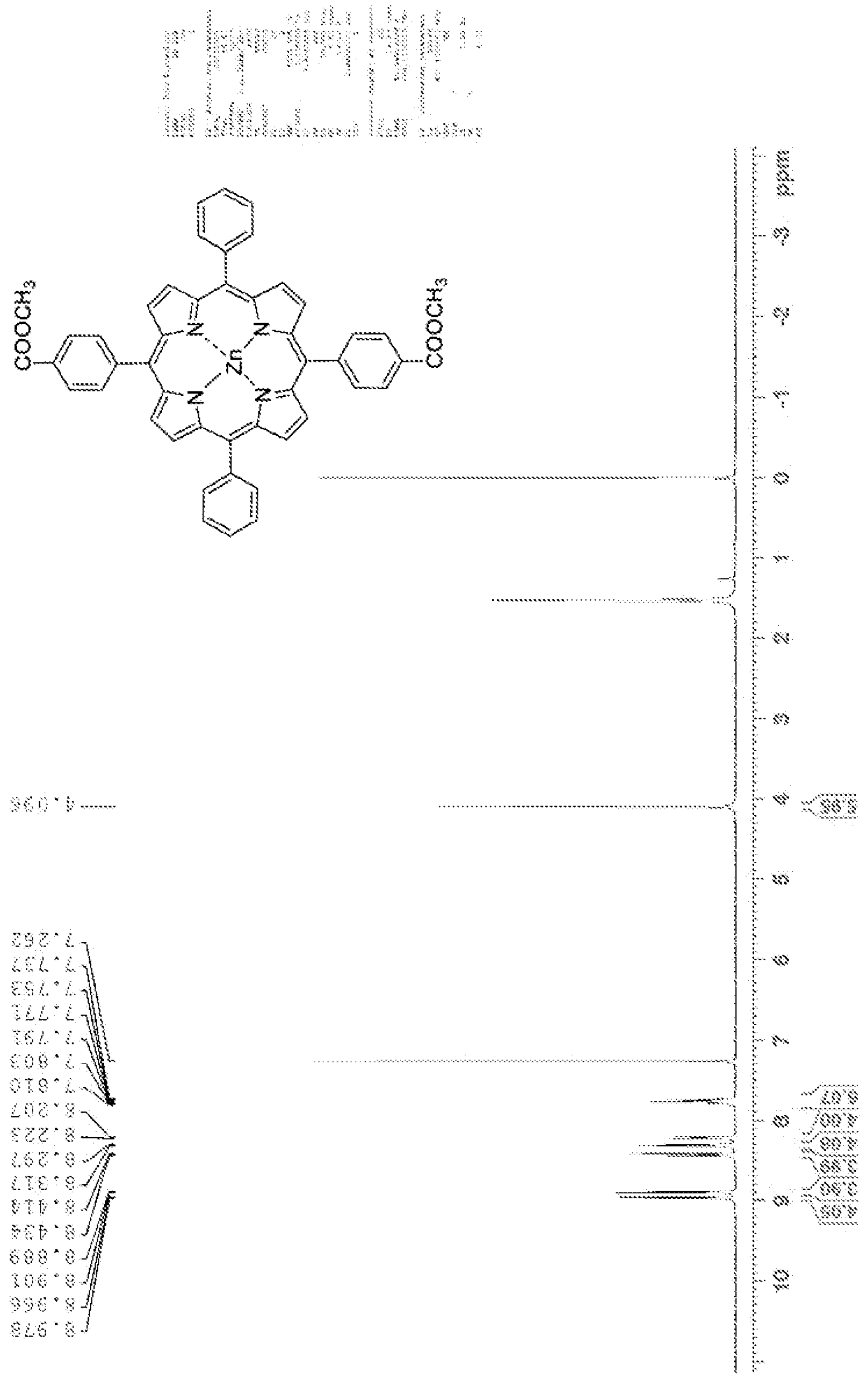
FIG. 24 shows the $^{13}H$ NMR spectra of ZnDMCPP recorded in $CDCl_3$.
Figure 25:
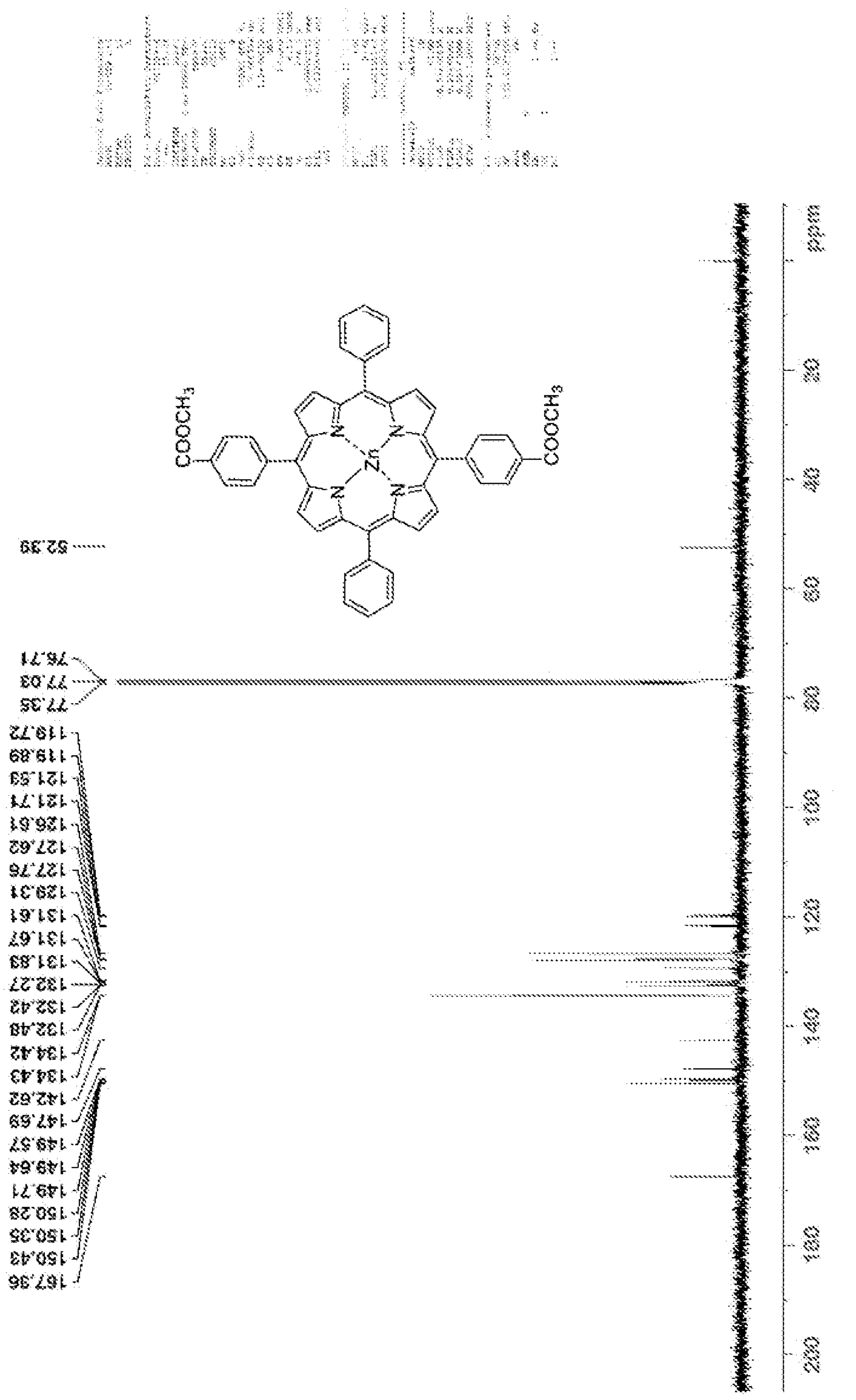
FIG. 25 shows the $^{13}C$ NMR spectra of ZnDMCPP recorded in $CDCl_3$.
Figure 26:
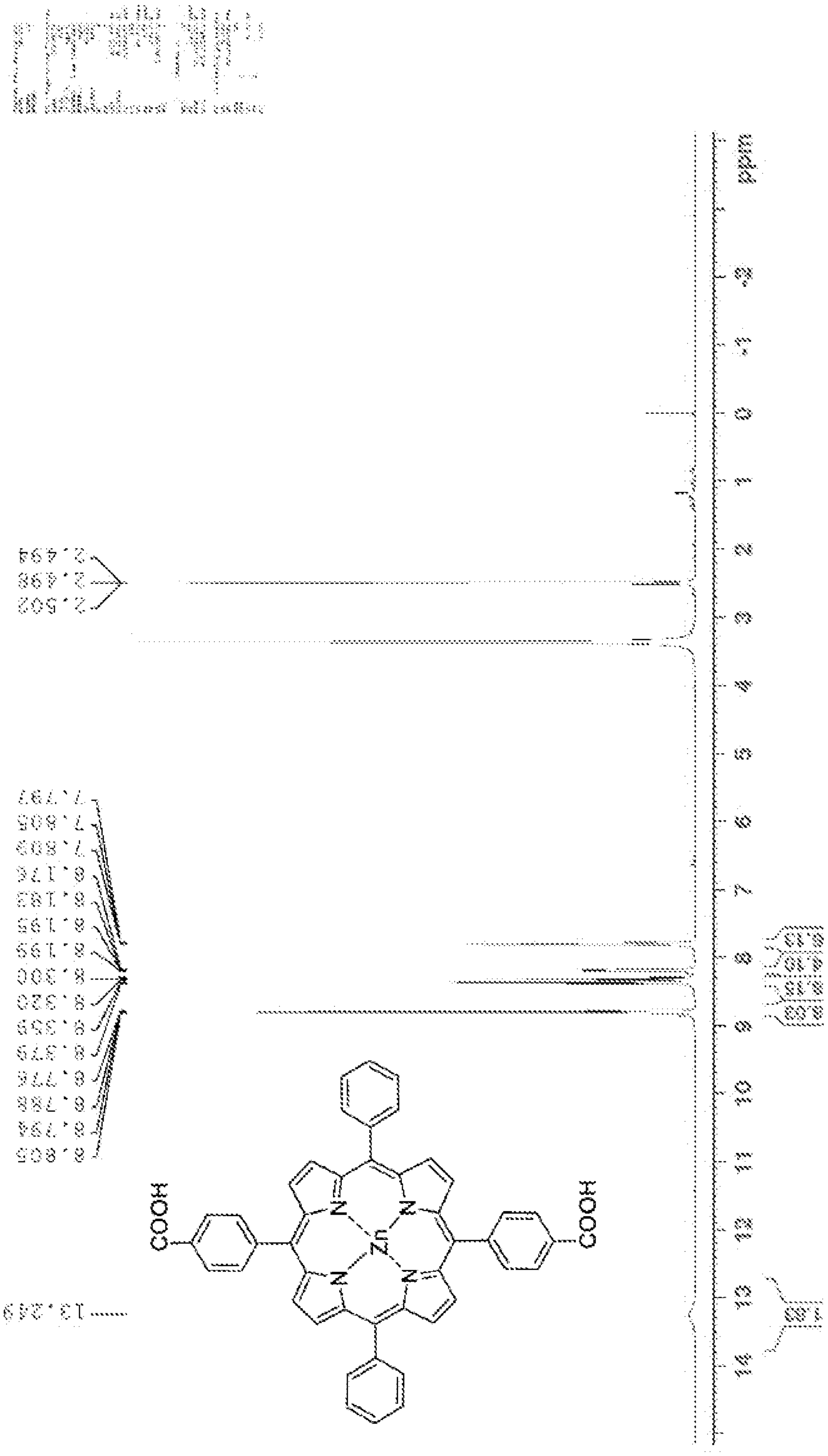
FIG. 26 shows the $^1$H NMR spectra of ZnDCPP recorded in DMSO-$d_6$.
Figure 27:
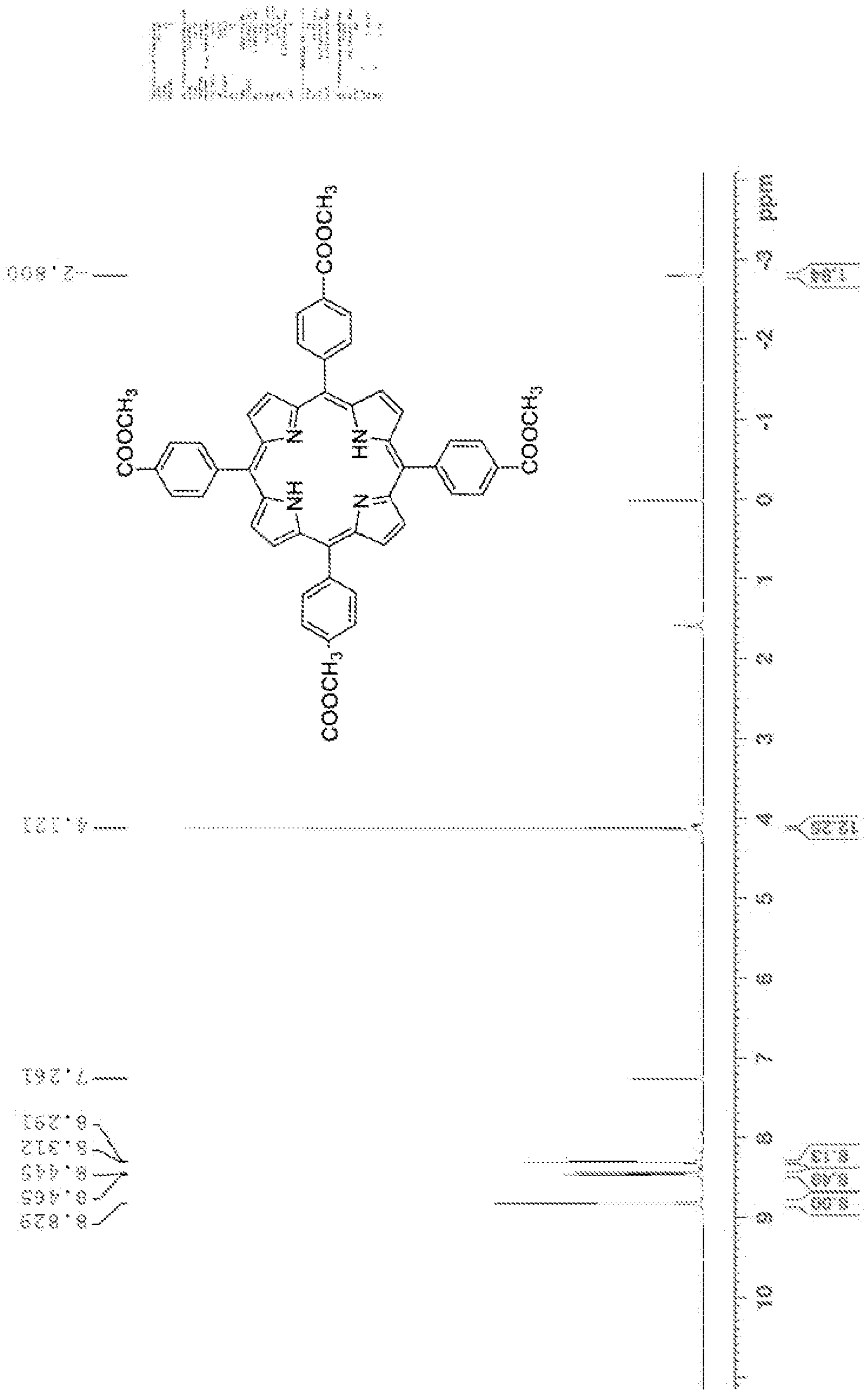
FIG. 27 shows the $^1$H NMR spectra of TMCPP recorded in $CDCl_3$.
Figure 28:
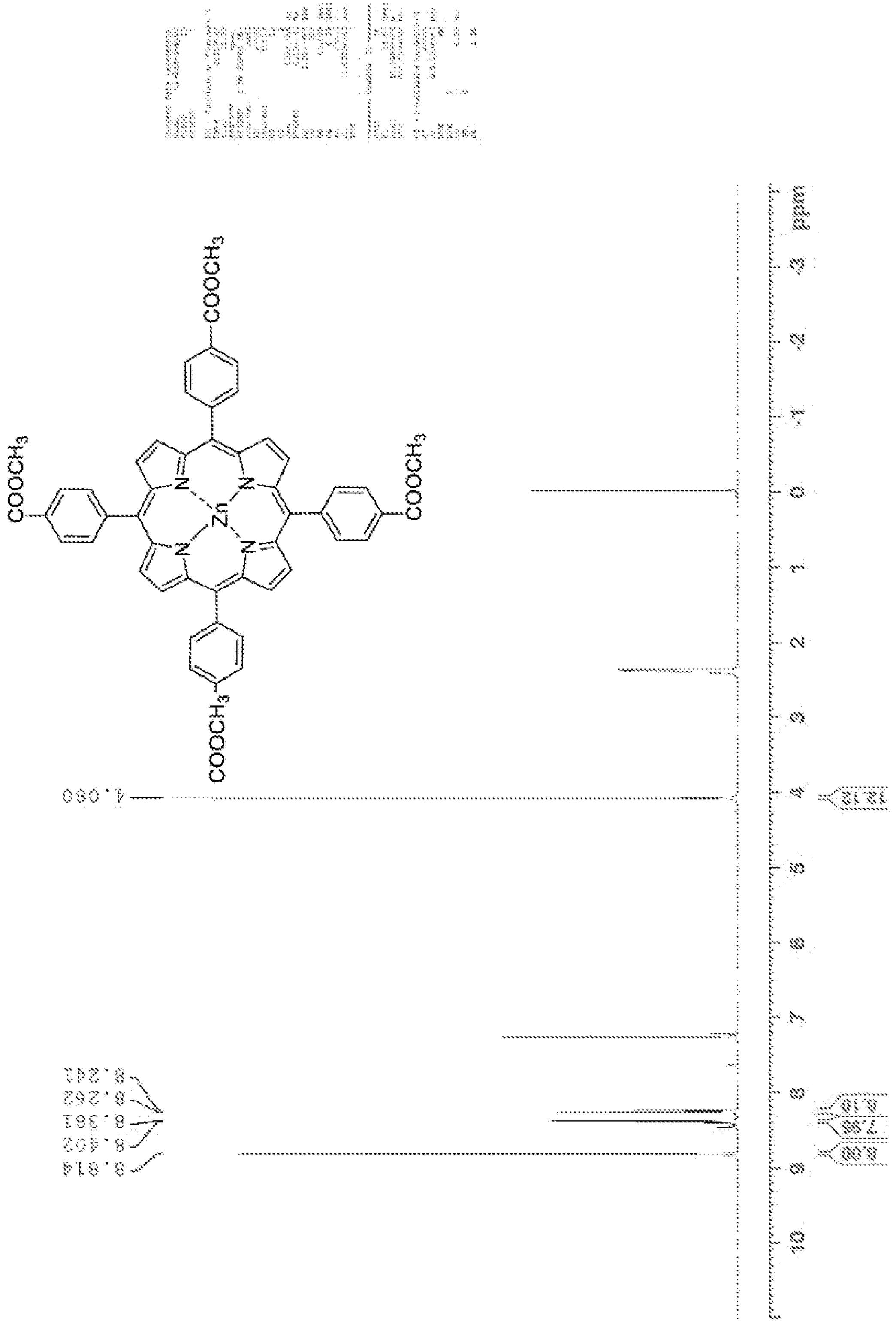
FIG. 28 shows the $^1$H NMR spectra of ZnTMCPP recorded in $CDCl_3$.
Figure 29:
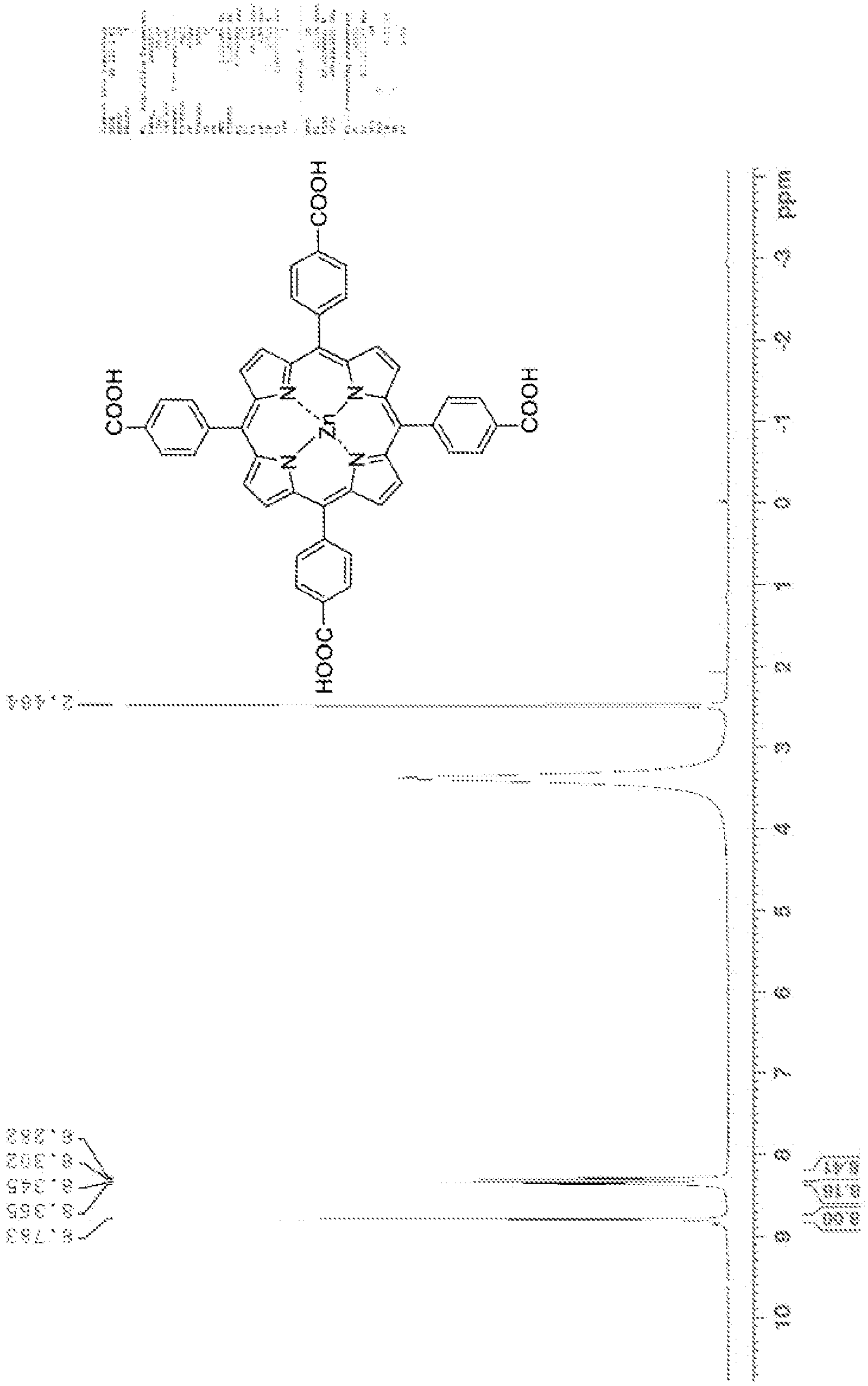
FIG. 29 shows the $^1$H NMR spectra of ZnTCPP recorded in DMSO-$d_6$
Figure 31:
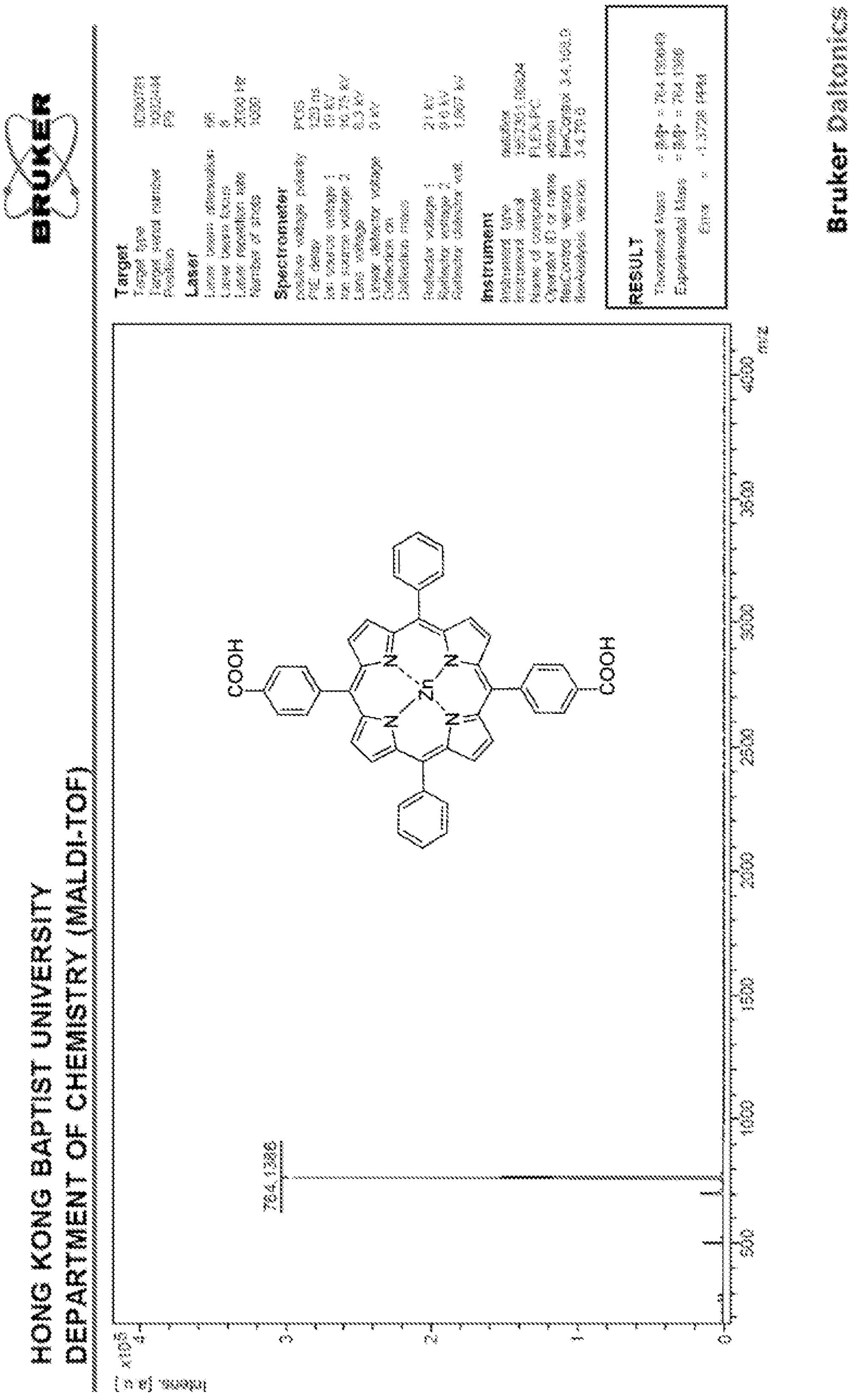
FIG. 31 shows the MALDI—TOF spectrum of ZnDCPP.
Figure 32:
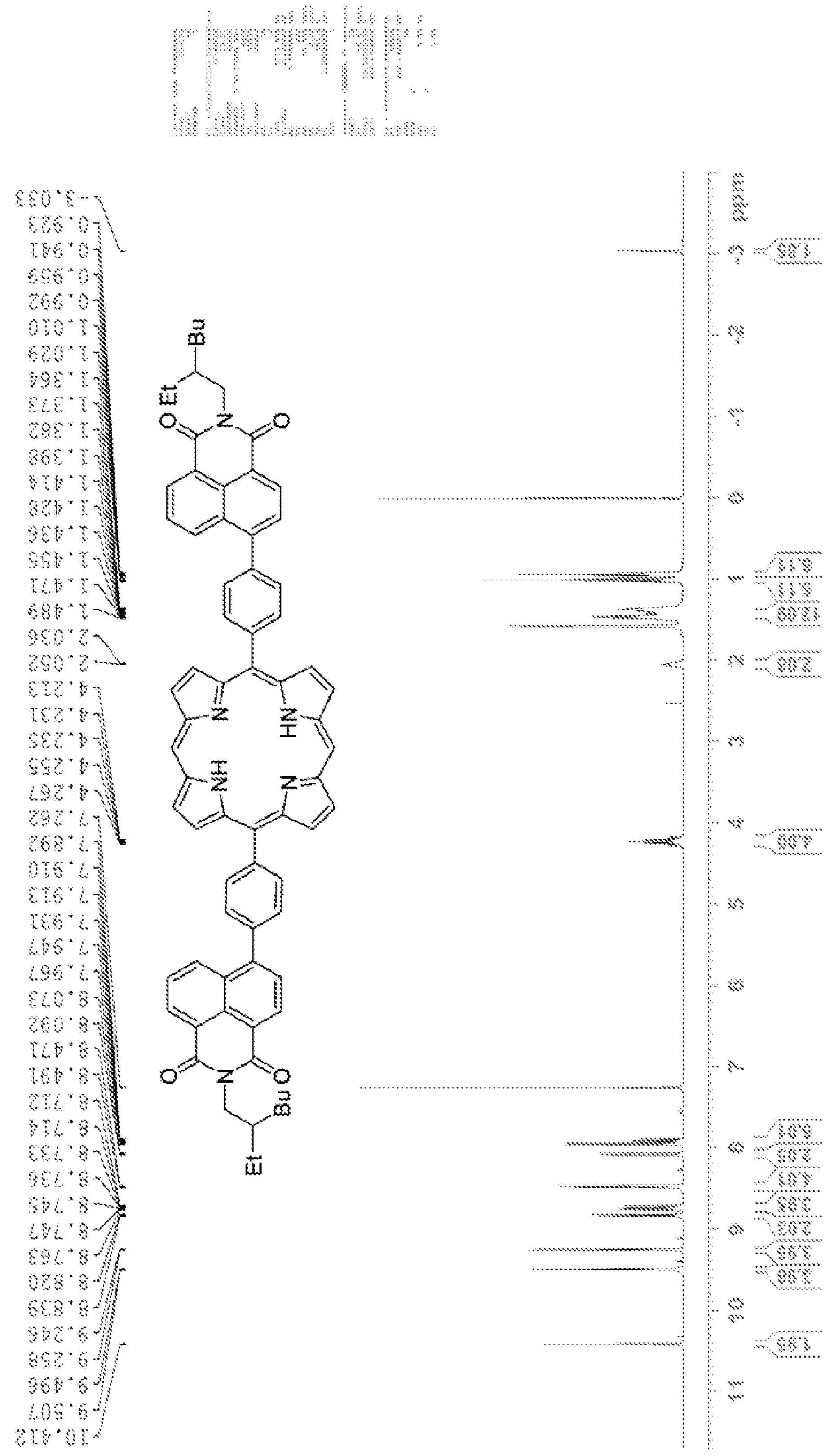
FIG. 32 shows the $^1$H NMR spectra of D(p-NI)PPH2 recorded in $CDCl_3$
Figure 33:
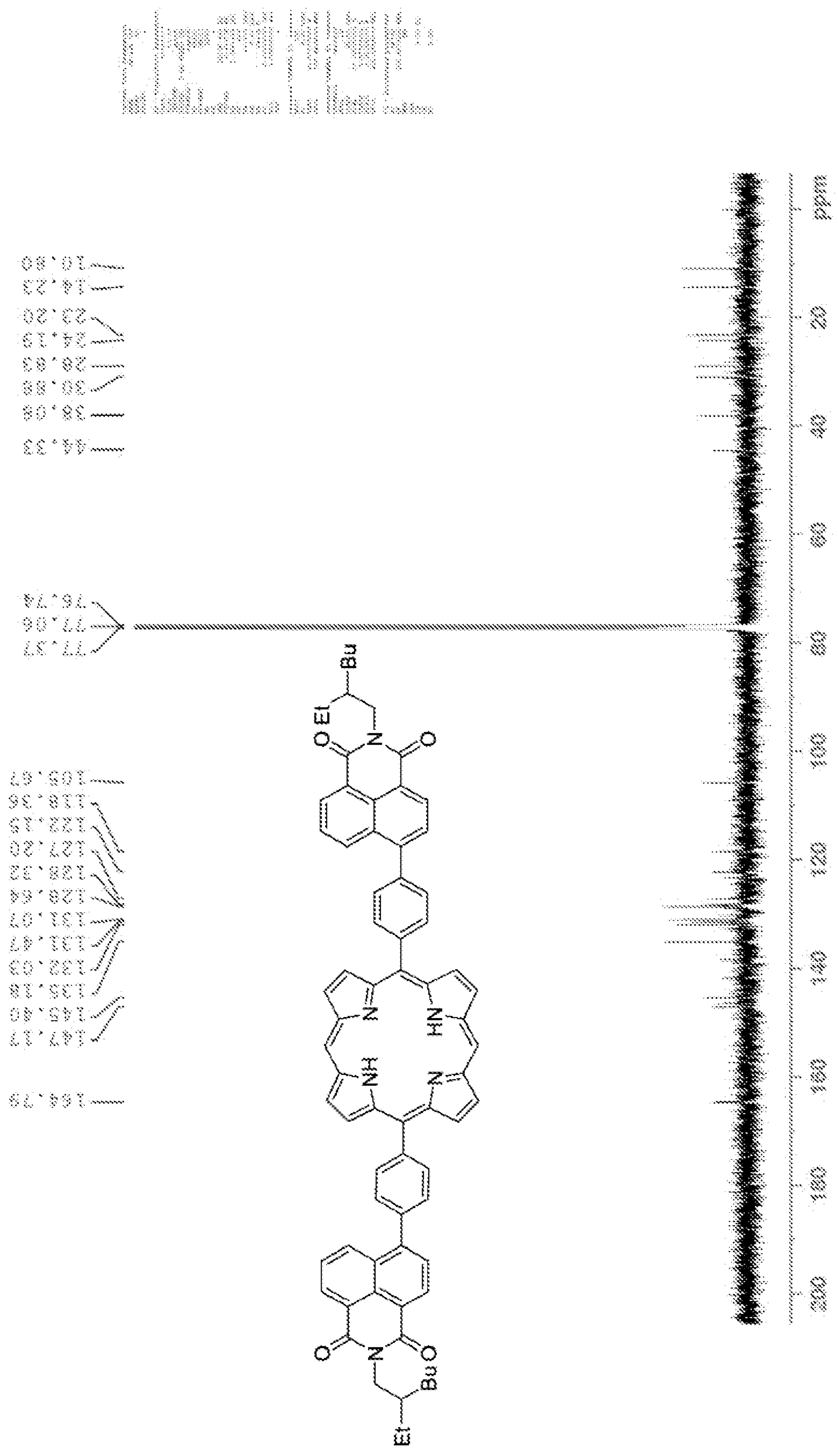
FIG. 33 shows the $^{13}$C NMR spectra of D(p-NI)PPH2 recorded in $CDCl_3$

The photoinduced hole-electron pair generation and separation of porphyrins also has tremendous role to transfer electrons from the excited porphyrins to WRC and thereby evolve $H_2$. Additionally, photocurrent response studies for the porphyrins described herein were also performed. As seen in FIG. 17, the photocurrent response of the porphyrins is in the following order: ZnDC(p-NI)PP>ZnDCPP>ZnTCPP. Among all, ZnDC(p-NI)PP porphyrin displayed higher photocurrent response than the conger porphyrins ZnDCPP and ZnTCPP suggesting the efficient photoinduced hole-electron pair separation and migration of electrons for the former porphyrin. This result is also in line with the higher PHE of ZnDC(p-NI)PP than the ZnDCPP and ZnTCPP.

In summary, new A-π-D-π-A based ZnDC(p-NI)PP porphyrins were designed and synthesized. The optoelectronic and PHE properties of this porphyrin were studied and compared with ZnDCPP porphyrin which lacks the NI moieties on meso-position of porphyrin ring. Absorption and emission spectra explored that the introduction of two NI moieties onto meso position of porphyrin ring in A-π-D-π-A configuration enhanced the light harvesting properties, $t_F$ and $\Phi_F$ values. Stern-Volmer quenching studies suggested that the electron accepting rate from ascorbic acid sacrificial donor and electron donating rate to CoPyCl water reduction catalyst were tremendously enhanced for ZnDC(p-NI)PP. This could be ascribed to the stabilized photoexcited states of ZnDC(p-NI)PP due to efficient energy transfer form NI moieties to porphyrin ring. Photocurrent response studies also revealed that the ZnDC(p-NI)PP higher photoinduced charge carriers generation and separation than the ZnDCPP. As a consequence, the homogeneous PS of ZnDC(p-NI)PP produced higher PHE properties such as $\eta H_2$ of 35.6 mmol $g^{-1}$ $h^{-1}$, TON of 5958 and AQE of 10.01% than those of ZnDCPP PS ($\eta H_2$ of 4.64 mmol $g^{-1}$ $h^{-1}$ TON of 1397 and AQE of 1.3%) and the typical ZnTCPP porphyrin bearing four COOH ($\eta H_2$ of 2.43 mmol $g^{-1}$ $h^{-1}$ TON of 562 and AQE of 1.0%).

What is claimed is:

1. A porphyrin having the Formula 1:

1

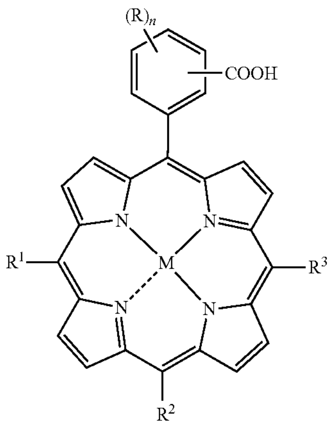

or a conjugate salt thereof, wherein

M is 2H, Zn, Fe, Ni, Co, V, Mn, Mg, Cu, Pt, Pd, or Sn;

n for each instance is a whole number selected from 0-3;

p for each instance is a whole number selected from 0-3;

q for each instance is 1 or 2;

r for each instance is a whole number selected from 0-2;

t for each instance is a whole number selected from 0-2;

R for each instance is alkyl, OH, cycloalkyl, aryl, heteroaryl, heterocycloalkyl, or COOH;

$R^1$ and $R^3$ are independently selected from the group consisting of:

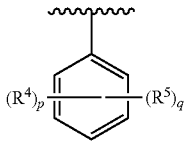

and

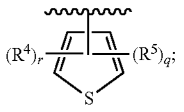

;

$R^2$ is selected from the group consisting of:

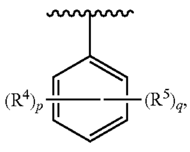

,

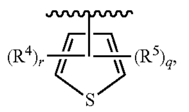

, and

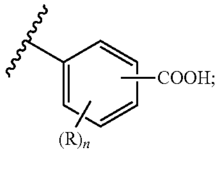

;

$R^4$ for each instance is independently selected from the group consisting of halide, nitro, nitrile, alkyl, perhaloalkyl, aryl, and heteroaryl;

$R^5$ is a moiety having the structure:

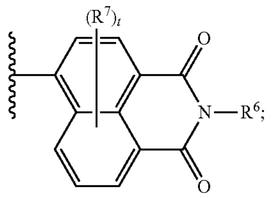

$R^6$ is alkyl, cycloalkyl, aryl or heteroaryl; and $R^7$ for each instance is independently selected from the group consisting of halide, nitro, nitrile, alkyl, perhaloalkyl, aryl, and heteroaryl.

2. The porphyrin of claim 1, wherein each of $R^1$ and $R^3$ is:

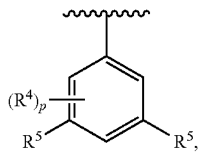

, or

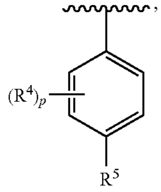

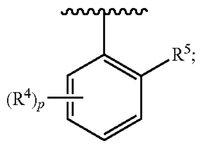

or each of $R^1$ and $R^3$ is:

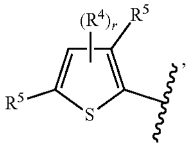

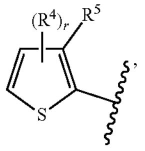

, or

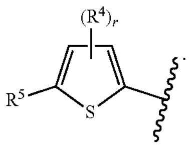

3. The porphyrin of claim 2, wherein $R^2$ is:

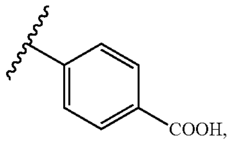

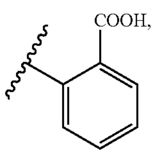

or

-continued

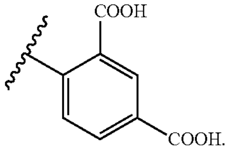

4. The porphyrin of claim 3, wherein p is 0 and r is 0.

5. The porphyrin of claim 1, wherein each of $R^1$, $R^2$, and $R^3$ is:

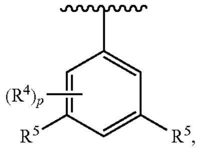

, or

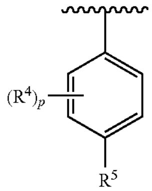

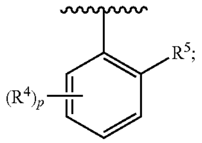

or each of $R^1$, $R^2$, and $R^3$ is:

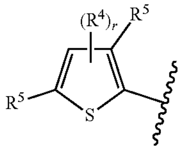

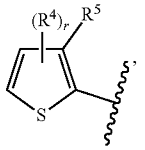

, or

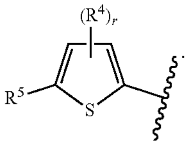

6. The porphyrin of claim 4, wherein p is 0 and r is 0.

7. The porphyrin of claim 1, wherein $R^6$ is alkyl.

8. The porphyrin of claim 1, wherein the porphyrin is selected from the group consisting of:
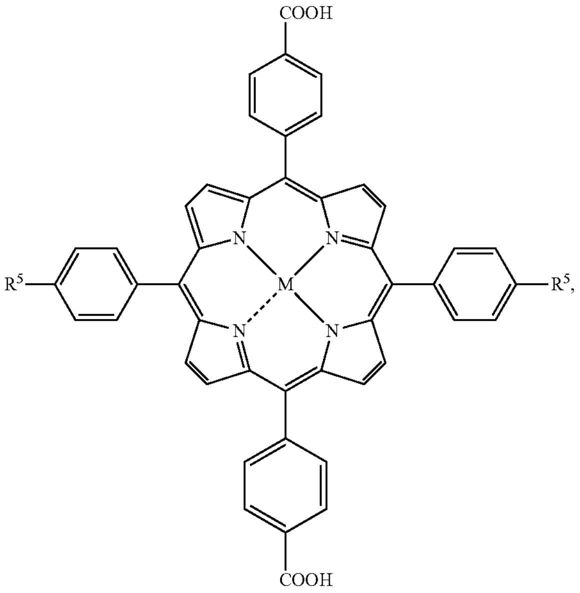
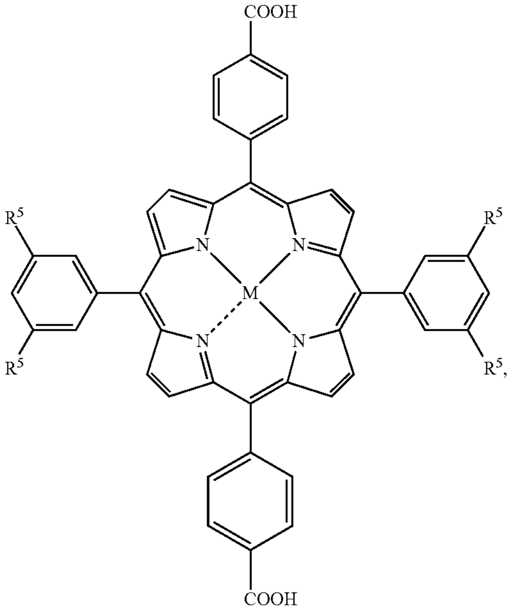
-continued
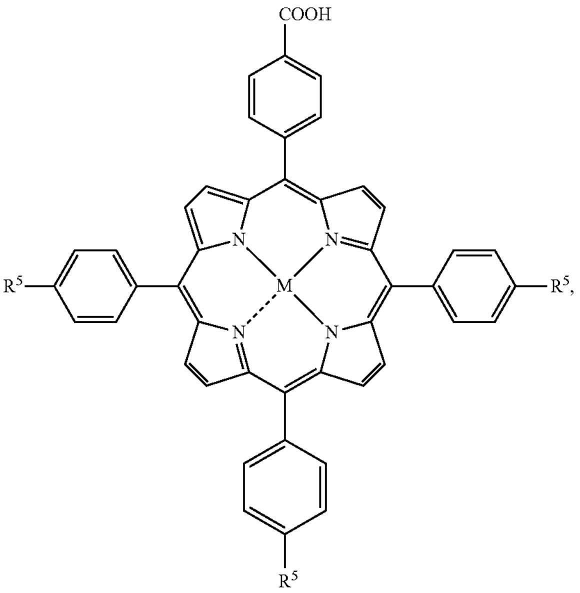
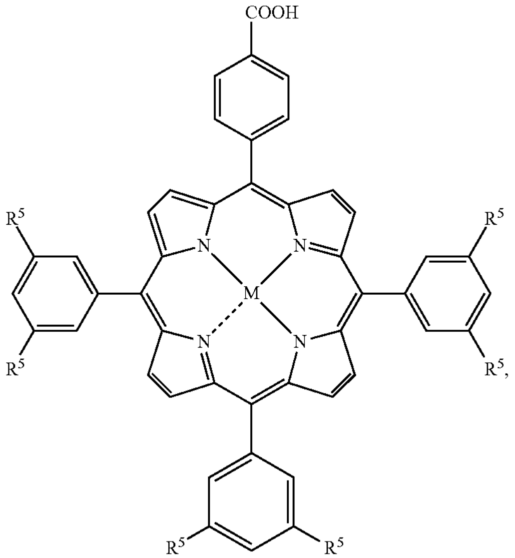

-continued
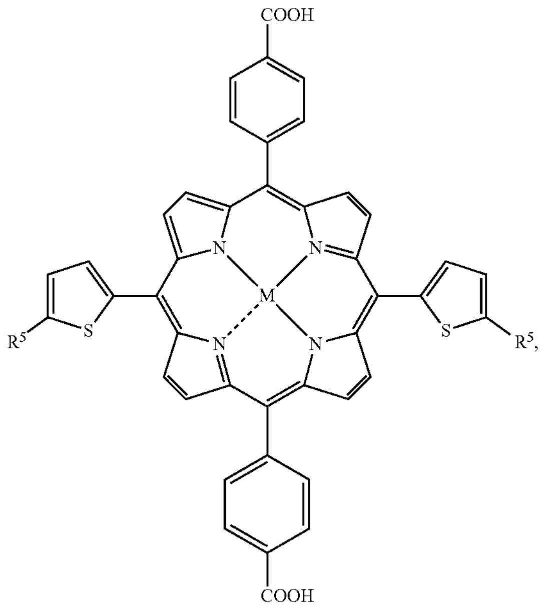
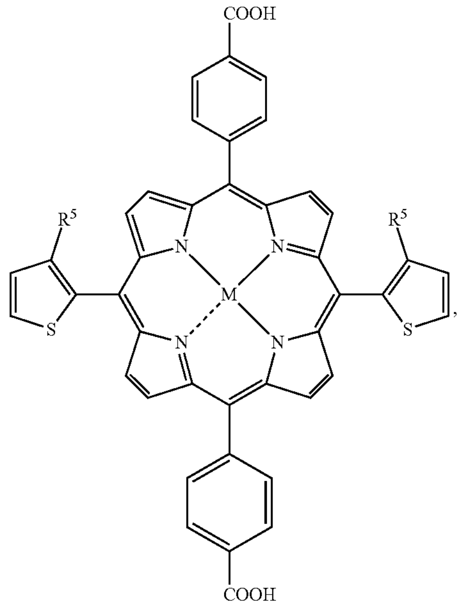
-continued
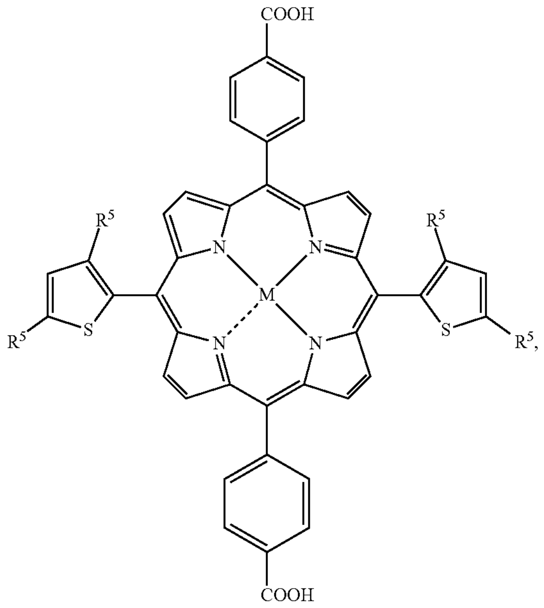
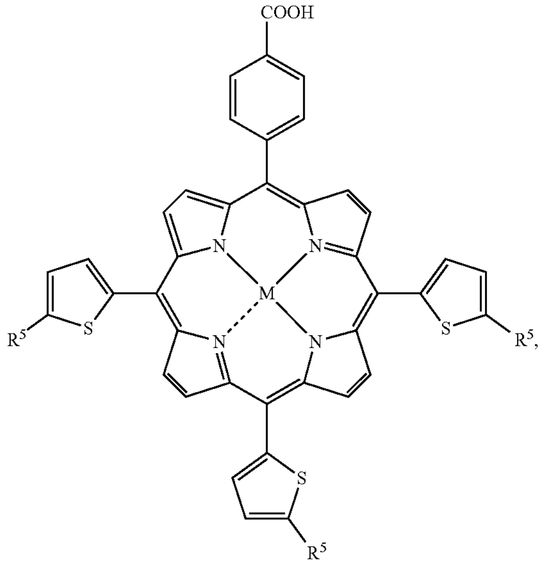
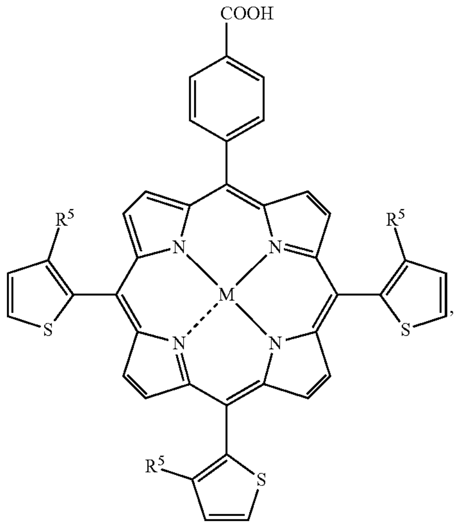
and -continued

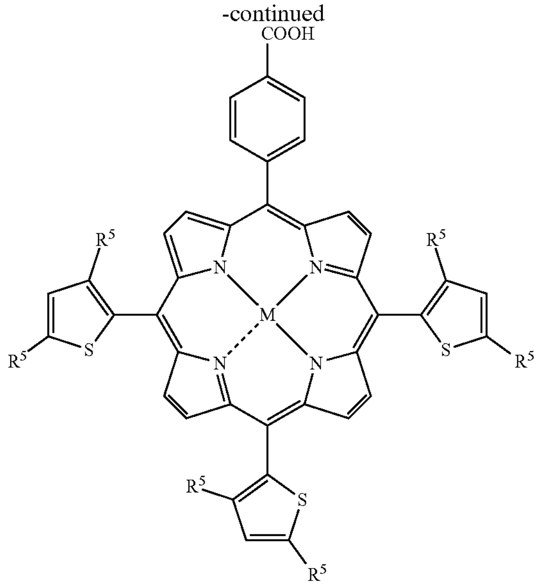

or a conjugate salt thereof.

9. The porphyrin of claim 8, wherein t is 0 and $R^6$ is alkyl.

10. The porphyrin of claim 9, wherein M is Zn(II).

11. The porphyrin of claim 1, wherein the porphyrin has the structure:

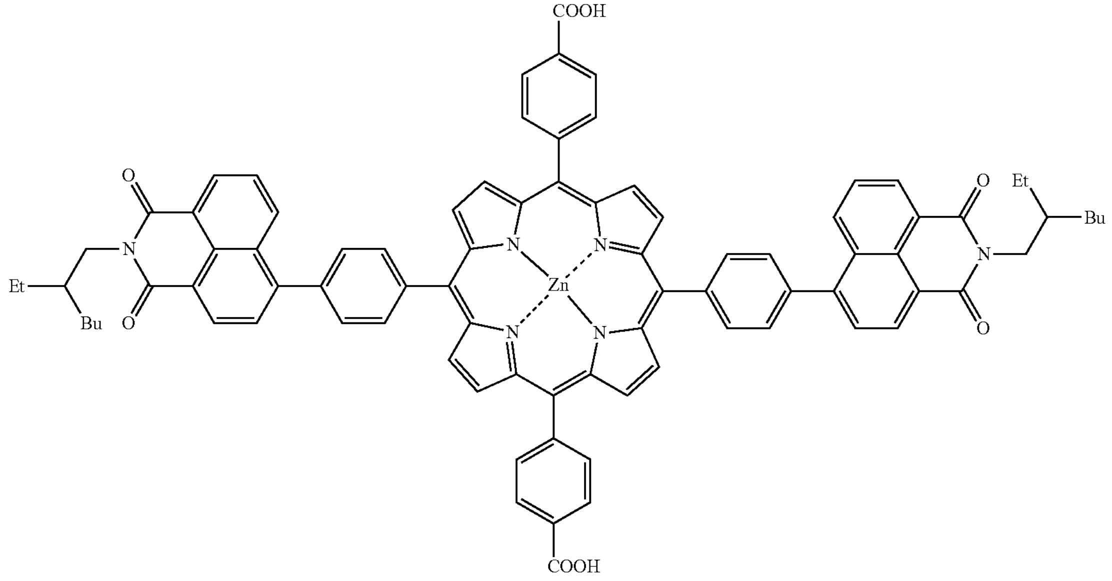

or a conjugate salt thereof.

12. A composition comprising a porphyrin of claim 1 and a water reduction catalyst.

13. The composition of claim 12, wherein the water reduction catalyst is a cobalt complex.

14. The composition of claim 13, wherein the cobalt complex is selected from the group consisting of a cobaloxime, a cobalt bipyridine, and a cobalt polypyridine.

15. The composition of claim 13, wherein the cobalt complex is chloro(pyridine)cobaloxime.

16. The composition of claim 12 further comprising water and a sacrificial electron donor.

17. The composition of claim 16, wherein the sacrificial electron donor is ascorbic acid, triethanolamine, triethylamine, ethylenediaminetetraacetic acid (EDTA), or a combination thereof.

18. A method of producing hydrogen gas comprising irradiating the composition of claim 16 with light.

19. The method of claim 18, wherein the porphyrin has the structure:
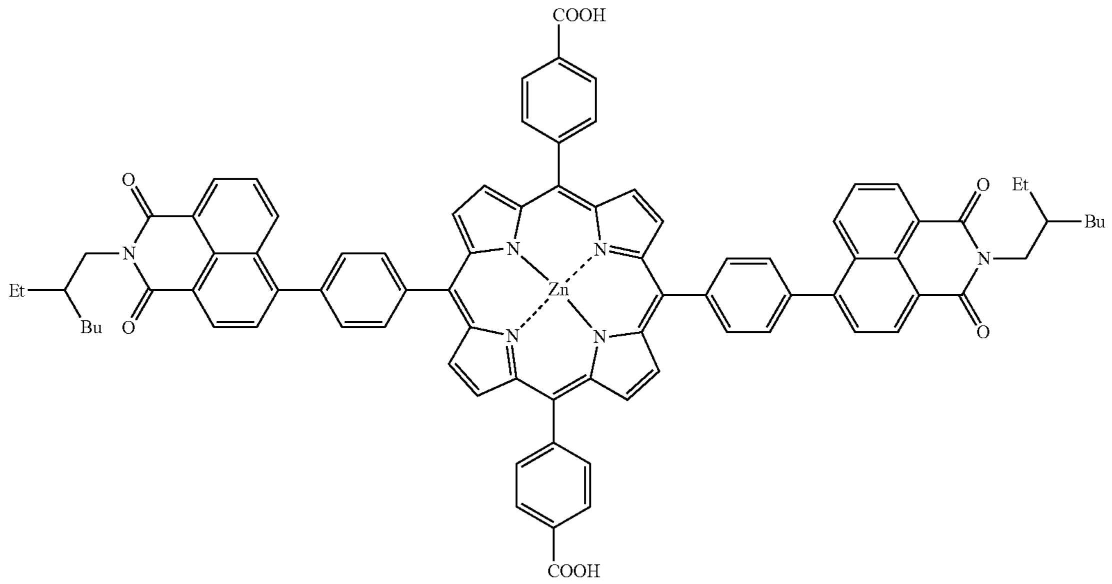
or a conjugate salt thereof.
20. The method of claim 19, wherein the water reduction catalyst is chloro(pyridine)cobaloxime.
* * * * *